(12) United States Patent
Fauber et al.

(10) Patent No.: US 10,280,144 B2
(45) Date of Patent: May 7, 2019

(54) PYRIDAZINE DERIVATIVES AS RORC MODULATORS

(71) Applicant: Genentech, Inc., South San Francisco, CA (US)

(72) Inventors: Benjamin Fauber, Austin, TX (US); James J. Crawford, South San Francisco, CA (US); Sarah M. Bronner, South San Francisco, CA (US); Monique Bodil van Niel, Essex (GB); Andrew Cridland, Essex (GB); Emanuela Gancia, Essex (GB); Christopher Hurley, Essex (GB); Jonathan Killen, Essex (GB); Stuart Ward, Essex (GB)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/801,192

(22) Filed: Nov. 1, 2017

(65) Prior Publication Data

US 2018/0072683 A1 Mar. 15, 2018

Related U.S. Application Data

(63) Continuation of application No. PCT/EP2016/059951, filed on May 4, 2016.

(60) Provisional application No. 62/321,872, filed on Apr. 13, 2016, provisional application No. 62/156,579, filed on May 4, 2015.

(51) Int. Cl.
*C07D 237/26* (2006.01)
*C07D 237/28* (2006.01)

(52) U.S. Cl.
CPC ......... *C07D 237/26* (2013.01); *C07D 237/28* (2013.01)

(58) Field of Classification Search
CPC .............................. C07D 237/26; C07D 237/28
See application file for complete search history.

(56) References Cited

U.S. PATENT DOCUMENTS 9,981,916 B2 * 5/2018 Bodil van Niel .... C07D 237/28

FOREIGN PATENT DOCUMENTS

WO 2015/067575 A1 5/2015

OTHER PUBLICATIONS

Monique B. Van Niel et al., "A reversed sulfonamide series of selective RORc inverse agonists" Bioorganic & Medicinal Chemistry Letters 24(24):5769-5776 (Oct. 25, 2014).
PCT ISR and Written Opinion for PCT/EP2016/059951.

* cited by examiner

*Primary Examiner* — Erich A Leeser
(74) *Attorney, Agent, or Firm* — Robert C. Hall

(57) ABSTRACT

Compounds of formula I:

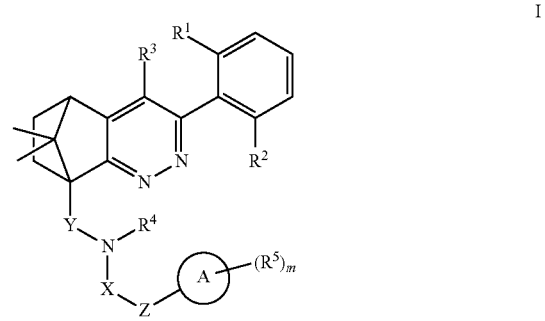

or pharmaceutical salts thereof,
wherein m, A, X, Y, Z, $R^1$, $R^2$, $R^3$, $R^4$ and $R^5$ are as defined herein. Also disclosed are methods of making the compounds and using the compounds for treatment of inflammatory diseases such as arthritis.

14 Claims, No Drawings

PYRIDAZINE DERIVATIVES AS RORC MODULATORS

CROSS REFERENCE TO RELATED APPLICATIONS

This Application is a continuation of International Application No. PCT/EP2016/059951 filed on May 4, 2016, which is entitled to the benefit U.S. Provisional Application No. 62/156,579 filed on May 4, 2015 and U.S. Provisional Application No. 62/321,872 filed on Apr. 13, 2016, the disclosures of which are incorporated herein by reference.

FIELD OF THE INVENTION

The invention pertains to compounds that modulate the function of retinoid-receptor related orphan receptor RORc (RORγ) and use of such compounds for treatment of autoimmune diseases

BACKGROUND OF THE INVENTION

T helper 17 cells (Th17) are interleukin (IL)-17 secreting CD4+ T cells involved in pathogenesis of autoimmune diseases such as rheumatoid arthritis, irritable bowel disease, psoriasis, psoriatic arthritis and spondyloarthridities. The retinoic acid-related orphan receptor γ (RORγ or RORc) is recognized as a transcription factor necessary for Th17 cell differentiation. RORc is an orphan member of the nuclear hormone receptor subfamily that includes RORα (RORa) and RORβ (RORb). RORc controls gene transcription by binding to DNA as a monomer. Selective modulation of RORc has been proposed as a route to discovery and development of Th17 cell-associated autoimmune diseases.

There is accordingly a need for compounds that inhibit RORc for use in treatment of autoimmune diseases such as rheumatoid arthritis, irritable bowel disease, psoriasis, psoriatic arthritis and spondyloarthridities.

SUMMARY OF THE INVENTION

The invention provides compounds of formula I:

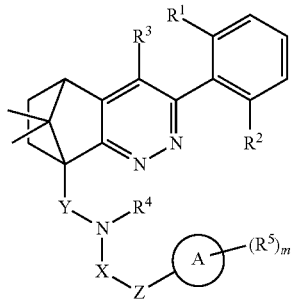

I or pharmaceutically acceptable salts thereof, wherein:
A is:
a five or six membered hetereoaryl selected from: oxazolyl; isoxazolyl; oxadiazolyl; thiazolyl; isothiazolyl; thiadiazolyl; triazolyl; pyrrolyl; pyrazolyl; imidazolyl; tetrazolyl; pyridinyl; pyrimidinyl; pyrazinyl; pyridazinyl; and triazinyl;
a bicyclic heteroaryl selected from: indolyl; indazolyl; isoindolyl; benzoxazinyl; benzoxazolyl; benzothiazolyl; benzimidazolyl; benzotriazinyl; pyrazolo[1,5-a]pyrimidinyl; 3H-imidazo[4,5-b]pyridinyl; and quinazolinyl
a five or six membered heterocyclyl selected from: oxetanyl; azetidinyl; azepinyl; pyrrolidinyl; piperidinyl; piperazinyl; imidazolidinyl; tetrahydrofuranyl; tetrahydropyranyl; tetrahydrothienyl, 1,1-dioxo-tetrahydrothienyl; morpholinyl; thiomorpolinyl; and 1,1-dioxo-thiomorpholinyl;
phenyl; or
$C_{3-6}$cycloalkyl;
X is: —C(O)— or —SO$_2$—;
Y is:
a bond;
$C_{1-6}$alkylene; or
halo-$C_{1-6}$alkylene;
Z is:
a bond;
$C_{1-6}$alkylene;
halo-$C_{1-6}$alkylene;
hydroxy-$C_{1-6}$alkylene;
—O—$C_{1-6}$alkylene; or
—NH—$C_{1-6}$alkylene;
m is: 0; 1; or 2;
$R^1$ is:
halo;
$R^2$ is:
hydrogen; or
halo;
$R^3$ is:
hydrogen;
$C_{1-6}$alkyl; or
halo;
$R^4$ is:
hydrogen;
$C_{1-6}$alkyl;
halo-$C_{1-6}$alkyl;
hydroxy-$C_{1-6}$alkyl;
cyano-$C_{1-6}$alkyl;
—$C_{1-6}$alkylene-C(O)$R^c$;
—$C_{1-6}$alkylene-heteroaryl wherein the heteroaryl is oxazolyl; isoxazolyl; oxadiazolyl; thiazolyl; isothiazolyl; thiadiazolyl; triazolyl; pyrrolyl; pyrazolyl; imidazolyl; tetrazolyl, each of which may be unsubstituted or substituted once with $R^a$.
$C_{3-6}$cycloalkyl which may be unsubstituted or substituted once or twice with $R^a$; or
$C_{3-6}$cycloalkyl-$C_{1-6}$alkyl wherein the $C_{3-6}$cycloalkyl may be unsubstituted or substituted once or twice with $R^a$; or
$R^5$ is:
$C_{1-6}$alkyl;
$C_{1-6}$alkyloxy;
halo-$C_{1-6}$alkyl;
halo-$C_{1-6}$alkoxy;
halo;
hydroxyl;
hydroxyl-$C_{1-6}$alkyl;
oxo;
cyano;
cyano-$C_{1-6}$alkyl;
$C_{1-6}$alkylsulfonyl;
$C_{1-6}$alkylsulfonylamino;
$C_{3-6}$cycloalkylsulfonyl;
$C_{3-6}$cycloalkylsulfonylamino;
$C_{1-6}$alkylsulfonyl;
$C_{3-6}$cycloalkyl-$C_{1-6}$alkylsulfonylamino;
$C_{1-6}$alkylsulfonyl-$C_{1-6}$alkyl;
amino;
aminocarbonyl;

aminosulfonyl;
$C_{1-6}$alkylcarbonyl;
$C_{1-6}$alkylcarbonylamino;
aminocarbonylamino;
$C_{1-6}$alkyloxycarbonyl;
$C_{1-6}$alkylaminosulfonyl;
phenyl which may be unsubstituted or substituted once or twice with $R^b$;
heteroaryl selected from: pyridinyl pyrimidinyl; pyrazinyl triazinyl; pyrazolyl; imidazolyl; oxazolyl; isoxazolyl; oxadiazolyl; and tetrazolyl; each of which may be unsubstituted or substituted once or twice with $R^a$;
heteroaryl-$C_{1-6}$alkyl wherein the heteroaryl is selected from: pyridinyl pyrimidinyl; pyrazinyl triazinyl; pyrazolyl; imidazolyl; oxazolyl; oxadiazolyl; isoxazolyl; and tetrazolyl; each of which may be unsubstituted or substituted once or twice with $R^a$;
heteroaryl-$C_{1-6}$alkoxy wherein the heteroaryl is selected from: pyridinyl pyrimidinyl; pyrazinyl triazinyl; pyrazolyl; imidazolyl; oxazolyl; oxadiazolyl; isoxazolyl; and tetrazolyl; each of which may be unsubstituted or substituted once or twice with $R^a$;
heterocyclyl selected from: morpholinyl; pyrrolidinyl; oxetanyl; and azetidinyl each of which may be unsubstituted or substituted once or twice with $R^b$;
$R^a$ is:
$C_{1-6}$alkyl;
$C_{3-6}$cycloalkyl;
halo-$C_{1-6}$alkyl;
halo;
hydroxyl;
hydroxyl-$C_{1-6}$alkyl; or
oxo;
$R^b$ is:
$C_{1-6}$alkyl;
$C_{1-6}$alkylcarbonyl;
$C_{1-6}$alkylsulfonyl;
halo-$C_{1-6}$alkyl;
halo;
hydroxyl;
hydroxyl-$C_{1-6}$alkyl; or
oxo; and
$R^c$ is:
hydroxyl;
$C_{1-6}$alkoxy; or
amino;
provided that the compound is not N-(((5R,8S)-3-(2,6-difluorophenyl)-9,9-dimethyl-5,6,7,8-tetrahydro-5,8-methanocinnolin-8-yl)methyl)-N-ethyl-5-methylisoxazole-3-carboxamide.

The invention also provides and pharmaceutical compositions comprising the compounds, methods of using the compounds, and methods of preparing the compounds.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise. In some instances dashes ("—") may be used interchangeably within definitions (for example, "alkoxyalkyl" omits the dash found in the equivalent term "alkoxy-alkyl").

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" and "alkyloxy", which may be used interchangeably, mean a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkoxyalkoxy' means a group of the formula —O—R—R' wherein R is alkylene and R' is alkoxy as defined herein.

"Alkylcarbonyl" means a moiety of the formula —C(O)—R, wherein R is alkyl as defined herein.

"Alkoxycarbonyl" means a group of the formula —C(O)—R wherein R is alkoxy as defined herein.

"Alkylcarbonylamino" means a group of the formula —R—C(O)—NR'— wherein R is alkyl and R' is hydrogen or alkyl.

"Alkylcarbonylalkyl" means a group of the formula —R—C(O)—R' wherein R is alkylene and R' is alkyl as defined herein.

"Alkoxyalkylcarbonyl" means a moiety of the formula —C(O)—R—R', wherein R is alkylene and R' is alkoxy as defined herein.

"Alkoxycarbonylalkyl" means a group of the formula —R—C(O)—R wherein R is alkylene and R' is alkoxy as defined herein.

"Alkoxycarbonylamino" means a moiety of the formula R—C(O)—NR'—, wherein R is alkoxy and R' is hydrogen or alkyl as defined herein.

"Alkoxycarbonylaminoalkyl" means a moiety of the formula R—C(O)—NR'—R"—, wherein R is alkoxy, R' is hydrogen or alkyl, and R" is alkylene as defined herein.

"Alkoxycarbonylalkoxy" means a group of the formula —O—R—C(O)—R' wherein R is alkylene and R' is alkoxy as defined herein.

"Hydroxycarbonylalkoxy" means a group of the formula —O—R—C(O)—OH wherein R is alkylene as defined herein.

"Alkylaminocarbonylalkoxy" means a group of the formula —O—R—C(O)—NHR' wherein R is alkylene and R' is alkyl as defined herein.

"Dialkylaminocarbonylalkoxy" means a group of the formula —O—R—C(O)—NR'R" wherein R is alkylene and R' and R" are alkyl as defined herein.

"Alkylaminoalkoxy" means a group of the formula —O—R—NHR' wherein R is alkylene and R' is alkyl as defined herein.

"Dialkylaminoalkoxy" means a group of the formula —O—R—NR'R' wherein R is alkylene and R' and R" are alkyl as defined herein.

"Alkylsulfonyl" means a moiety of the formula —SO$_2$—R, wherein R is alkyl as defined herein.

"Alkylsulfonylalkyl means a moiety of the formula —R'—SO$_2$—R" where where R' is alkylene and R" is alkyl as defined herein.

"Alkylsulfonylalkoxy" means a group of the formula —O—R—SO$_2$—R' wherein R is alkylene and R' is alkyl as defined herein.

"Amino means a moiety of the formula —NRR' wherein R and R' each independently is hyrdogen or alkyl as defined herein. "Amino thus includes "alkylamino (where one of R and R' is alkyl and the other is hydrogen) and "dialkylamino (where R and R' are both alkyl.

"Aminocarbonyl" means a group of the formula —C(O)—R wherein R is amino as defined herein.

"N-hydroxy-aminocarbonyl" means a group of the formula —C(O)—NR—OH wherein R is hydrogen or alkyl as defined herein.

"N-alkoxy-aminocarbonyl" means a group of the formula —C(O)—NR—R' wherein R is hydrogen or alkyl and R' is alkoxy as defined herein.

"Aminocarbonylaminoalkyl" means a group of the formula R$_2$N—C(O)—NR'—R"— wherein each R is independently hydrogen or alkyl, R' is hydrogen or alkyl, and R" is alkylene as defined herein.

"N-alkyl-aminocarbonyl" means a group of the formula —C(O)—NH—R wherein R is alkyl as defined herein.

"N-hydroxy-N-alkylaminocarbonyl" means a group of the formula —C(O)—NRR' wherein R is alkyl as defined herein and R' is hydroxy.

"N-alkoxy-N-alkylaminocarbonyl" means a group of the formula —C(O)—NRR' wherein R is alkyl and R' is alkoxy as defined herein.

"N,N-di-C$_{1-6}$alkyl-aminocarbonyl" means a group of the formula —C(O)—NRR' wherein R and R' are alkyl as defined herein.

"Aminosulfonyl" means a group of the formula —SO$_2$—NH$_2$.

"N-alkylaminosulfonyl" means a group of the formula —SO$_2$—NHR wherein R is alkyl as defined herein.

"N,N-dialkylaminosulfonyl" means a group of the formula —SO$_2$—NRR' wherein R and R' are alkyl as defined herein.

"Alkylsulfonylamino" means a group of the formula —NR'—SO$_2$—R wherein R id alkyl and R' is hydrogen or alkyl as defined herein.

"N-(alkylsulfonyl)-aminoalkyl" means a group of the formula —R—NH—SO$_2$—R' wherein R is alkylene and R' is alkyl as defined herein.

"N-(Alkylsulfonyl)aminocarbonyl" means a group of the formula —C(O)—NH—SO$_2$—R wherein wherein R is alkyl as defined herein.

"N-(Alkylsulfonyl)-N-alkylaminocarbonyl" means a group of the formula —C(O)—NR—SO$_2$—R' wherein wherein R and R' are alkyl as defined herein.

"N-Alkoxyalkyl-aminocarbonyl" means a group of the formula —C(O)—NR—R'—OR" wherein R is hydrogen or alkyl, R' is alkylene, and R" is alkyl as defined herein.

"N-Hydroxyalkyl-aminocarbonyl" means a group of the formula —C(O)—NR—R'—OH" wherein R is hydrogen or alkyl and R' is alkylene as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein.

"Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'SO$_2$—R wherein R is alkyl and R' is hydrogen or alkyl.

"Aminocarbonyloxyalkyl" or "carbamylalkyl" means a group of the formula —R—O—C(O)—NR'R" wherein R is alkylene and R', R" each independently is hydrogen or alkyl as defined herein.

"Alkynylalkoxy" means a group of the formula —O—R—R' wherein R is alkylene and R' is alkynyl as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, of which may be optionally substituted as defined herein.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Arylsulfonyl means a group of the formula —SO$_2$—R wherein R is aryl as defined herein.

"Aryloxy" means a group of the formula —O—R wherein R is aryl as defined herein.

"Aralkyloxy" means a group of the formula —O—R—R" wherein R is alkylene and R' is aryl as defined herein.

"Carboxy" or "hydroxycarbonyl", which may be used interchangeably, means a group of the formula —C(O)—OH.

"Cyanoalkyl" " means a moiety of the formula —R'—R", where R' is alkylene as defined herein and R" is cyano or nitrile.

"Cycloalkyl" means a monovalent saturated carbocyclic moiety consisting of mono- or bicyclic rings. Particular cycloalkyl are unsubstituted or substituted with alkyl. Cycloalkyl can optionally be substituted as defined herein. Unless defined otherwise, cycloalkyl may be optionally substituted with one or more substituents, wherein each substituent is independently hydroxy, alkyl, alkoxy, halo, haloalkyl, amino, monoalkylamino, or dialkylamino. Examples of cycloalkyl moieties include, but are not limited to, cyclopropyl, cyclobutyl, cyclopentyl, cyclohexyl, cycloheptyl, and the like, including partially unsaturated (cycloalkenyl) derivatives thereof.

"Cycloalkenyl" means a cycloalkyl as defined herein that includes at least one double bond or unsaturation. Exemplary cycloalkenyl include cyclohexenyl, cyclopentenyl, cyclobutenyl and the like.

"Cycloalkylalkyl" means a moiety of the formula —R'—R", where R' is alkylene and R" is cycloalkyl as defined herein.

"Cycloalkylalkoxy" means a group of the formula —O—R—R' wherein R is alkylene and R' is cycloalkyl as defined herein.

"Cycloalkylcarbonyl" means a moiety of the formula —C(O)—R, wherein R is cycloalkyl as defined herein.

"$C_{3-6}$cycloalkyl-$C_{1-6}$alkyl-carbonyl" means a moiety of the formula —C(O)—R, wherein R is cycloalkylalkyl as defined herein.

"Cyanoalkylcarbonyl" means a moiety of the formula —C(O)—R—R', wherein R is alkylene as defined herein and R' is cyano or nitrile.

"N-Cyano-aminocarbonyl" means a moiety of the formula —C(O)—NHR, wherein R is cyano or nitrile.

"N-Cyano-N-alkyl-aminocarbonyl" means a moiety of the formula —C(O)—NRR'—R, wherein R' is alkyl as defined herein and R is cyano or nitrile.

"Cycloalkylsulfonyl" means a group of the formula —$SO_2$—R wherein R is cycloalkyl as defined herein.

"Cycloalkylalkylsulfonyl" means a group of the formula —$SO_2$—R wherein R is cycloalkylalkyl as defined herein.

"Formyl" means a moiety of the formula —C(O)—H.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, each of which may be optionally substituted as defined herein.

Heteroarylalkyl" or "heteroaralkyl" means a group of the formula —R—R' wherein R is alkylene and R' is heteroaryl as defined herein.

"Heteroarylsulfonyl means a group of the formula —$SO_2$—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, morpholinyl, thiomorpholinyl, azepinyl, pyrrolidinyl, azetidinyl, tetrahydropyranyl, tetrahydrofuranyl, oxetanyl and the like. Such heterocyclyl may be optionally substituted as defined herein.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxycarbonylalkoxy" means a group of the formula —O—R—C(O)—OH wherein R is alkylene as defined herein.

"Hydroxyalkylcarbonyl" means a moiety of the formula —C(O)—R—R', wherein R is alkylene as defined herein and R' is hydroxy.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, for example, one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"Oxo" means a group of the formula =O (i.e., an oxygen with a double bond). Thus, for example, a 1-oxo-ethyl group is an acetyl group.

"Alkoxy hydroxyalkyl" and "hydroxy alkoxyalkyl", which may be used interchangeably, means an alkyl as defined herein that is substituted at least once with hydroxy and at least once with alkoxy.

"Alkoxy hydroxyalkyl" and "hydroxy alkoxyalkyl" thus encompass, for example, 2-hydroxy-3-methoxy-propan-1-yl and the like.

"Urea" or "ureido" means a group of the formula —NR'—C(O)—NR"R'" wherein R', R" and R'" each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —SO$_2$—NR'R" wherein R', R" and R'" each independently is hydrogen or alkyl.

"Optionally substituted" when used in association with an "aryl", phenyl", "heteroaryl" "cycloalkyl" or "heterocyclyl" moiety means that such moiety may be unsubstituted (i.e., all open valencies are occupied by a hydrogen atom) or substituted with specific groups as related herein.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Arthritis" means a disease or condition that causes damage to joints of the body and pain associated with such joint damage. Arthritis includes rheumatoid arthritis, osteoarthritis, psoriatic arthritis, septic arthritis, spondyloarthropathies, gouty arthritis, systemic lupus erythematosus and juvenile arthritis, osteoarthritis, and other arthritic conditions.

"Respiratory disorder" refers to, without limitation, chronic obstructive pulmonary disease (COPD), asthma, bronchospasm, and the like.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as particular definitions, if any.

"Treating" or "treatment" of a disease state includes, inter alia, inhibiting the disease state, i.e., arresting the development of the disease state or its clinical symptoms, and/or relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature and chemical names used in this Application are based on ChembioOffice™ by Cambridge Soft™. Any open valency appearing on a carbon, oxygen sulfur or nitrogen atom in the structures herein indicates the presence of a hydrogen atom unless indicated otherwise. Where a nitrogen-containing heteroaryl ring is shown with an open valency on a nitrogen atom, and variables such as $R^a$, $R^b$ or $R^c$ are shown on the heteroaryl ring, such variables may be bound or joined to the open valency nitrogen. Where a chiral center exists in a structure but no specific stereochemistry is shown for the chiral center, both enantiomers associated with the chiral center are encompassed by the structure. Where a structure shown herein may exist in multiple tautomeric forms, all such tautomers are encompassed by the structure. The atoms represented in the structures herein are intended to encompass all naturally occurring isotopes of such atoms. Thus, for example, the hydrogen atoms represented herein are meant to include deuterium and tritium, and the carbon atoms are meant to include $C^{13}$ and $C^{14}$ isotopes. One or more carbon atom(s) of a compound of the invention may be replaced by a silicon atom(s), and it is contemplated that one or more oxygen atom(s) of a compound of the invention may be replaced by a sulfur or selenium atom(s).

Compounds of the Invention

The invention provides compounds of formula I:

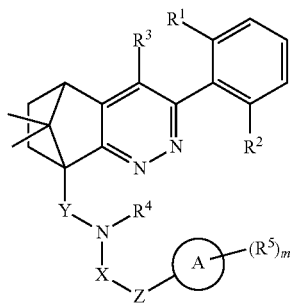

or pharmaceutically acceptable salts thereof, wherein:

A is:
  a five or six membered hetereoaryl selected from: oxazolyl; isoxazolyl; oxadiazolyl; thiazolyl; isothiazolyl; thiadiazolyl; triazolyl; pyrrolyl; pyrazolyl; imidazolyl; tetrazolyl; pyridinyl; pyrimidinyl; pyrazinyl; pyridazinyl; and triazinyl;
  a bicyclic heteroaryl selected from: indolyl; indazolyl; isoindolyl; benzoxazinyl; benzoxazolyl; benzothiazolyl; benzimidazolyl; benzotriazinyl; pyrazolo[1,5-a]pyrimidinyl; 3H-imidazo[4,5-b]pyridinyl; and quinazolinyl a five or six membered heterocyclyl selected from: oxetanyl; azetidinyl; azepinyl; pyrrolidinyl; piperidinyl; piperazinyl; imidazolidinyl; tetrahydrofuranyl; tetrahydropyranyl; tetrahydrothienyl, 1,1-dioxo-tetrahydrothienyl; morpholinyl; thiomorpolinyl; and 1,1-dioxo-thiomorpholinyl;
  phenyl; or
  $C_{3-6}$cycloalkyl;

X is: —C(O)— or —SO$_2$—;

Y is:
  a bond;
  $C_{1-6}$alkylene; or
  halo-$C_{1-6}$alkylene;

Z is:
  a bond;
  $C_{1-6}$alkylene;
  halo-$C_{1-6}$alkylene;
  hydroxy-$C_{1-6}$alkylene;
  —O—$C_{1-6}$alkylene; or
  —NH—$C_{1-6}$alkylene;

m is: 0; 1; or 2;

$R^1$ is:
  halo;

$R^2$ is:
  hydrogen; or
  halo;

$R^3$ is:
  hydrogen;
  $C_{1-6}$alkyl; or
  halo;

$R^4$ is:
  hydrogen;
  $C_{1-6}$alkyl;
  halo-$C_{1-6}$alkyl;
  hydroxy-$C_{1-6}$alkyl;
  cyano-$C_{1-6}$alkyl;
  —$C_{1-6}$alkylene-C(O)$R^c$;
  —$C_{1-6}$alkylene-heteroaryl wherein the heteroaryl is oxazolyl; isoxazolyl; oxadiazolyl; thiazolyl; isothiazolyl; thiadiazolyl; triazolyl; pyrrolyl; pyrazolyl; imidazolyl; tetrazolyl, each of which may be unsubstituted or substituted once with $R^a$.
  $C_{3-6}$cycloalkyl which may be unsubstituted or substituted once or twice with $R^a$; or
  $C_{3-6}$cycloalkyl-$C_{1-6}$alkyl wherein the $C_{3-6}$cycloalkyl may be unsubstituted or substituted once or twice with $R^a$; or $R^5$ is:
  $C_{1-6}$alkyl;
  $C_{1-6}$alkyloxy;
  halo-$C_{1-6}$alkyl;
  halo-$C_{1-6}$alkoxy;
  halo;
  hydroxyl;
  hydroxyl-$C_{1-6}$alkyl;
  oxo;
  cyano;
  cyano-$C_{1-6}$alkyl;
  $C_{1-6}$alkylsulfonyl;
  $C_{1-6}$alkylsulfonylamino;
  $C_{3-6}$cycloalkylsulfonyl;
  $C_{3-6}$cycloalkylsulfonylamino;
  $C_{1-6}$alkylsulfonyl;
  $C_{3-6}$cycloalkyl-$C_{1-6}$alkylsulfonylamino;
  $C_{1-6}$alkylsulfonyl-$C_{1-6}$alkyl;
  amino;
  aminocarbonyl;
  amino sulfonyl;
  $C_{1-6}$alkylcarbonyl;

$C_{1-6}$alkylcarbonylamino;
aminocarbonylamino;
$C_{1-6}$alkyloxycarbonyl;
$C_{1-6}$alkylaminosulfonyl;
phenyl which may be unsubstituted or substituted once or twice with $R^b$;
heteroaryl selected from: pyridinyl pyrimidinyl; pyrazinyl triazinyl; pyrazolyl; imidazolyl; oxazolyl; isoxazolyl; oxadiazolyl; and tetrazolyl; each of which may be unsubstituted or substituted once or twice with $R^a$;
heteroaryl-$C_{1-6}$alkyl wherein the heteroaryl is selected from: pyridinyl pyrimidinyl; pyrazinyl triazinyl; pyrazolyl; imidazolyl; oxazolyl; oxadiazolyl; isoxazolyl; and tetrazolyl; each of which may be unsubstituted or substituted once or twice with $R^a$;
heteroaryl-$C_{1-6}$alkoxy wherein the heteroaryl is selected from: pyridinyl pyrimidinyl; pyrazinyl triazinyl; pyrazolyl; imidazolyl; oxazolyl; oxadiazolyl; isoxazolyl; and tetrazolyl; each of which may be unsubstituted or substituted once or twice with $R^a$;
heterocyclyl selected from: morpholinyl; pyrrolidinyl; oxetanyl; and azetidinyl each of which may be unsubstituted or substituted once or twice with $R^b$;

$R^a$ is:
$C_{1-6}$alkyl;
$C_{3-6}$cycloalkyl;
halo —$C_{1-6}$alkyl;
halo;
hydroxyl;
hydroxyl-$C_{1-6}$alkyl; or
oxo;

$R^b$ is:
$C_{1-6}$alkyl;
$C_{1-6}$alkylcarbonyl;
$C_{1-6}$alkylsulfonyl;
halo-$C_{1-6}$alkyl;
halo;
hydroxyl;
hydroxyl-$C_{1-6}$alkyl; or
oxo; and $R^c$ is:
hydroxyl;
$C_{1-6}$alkoxy; or
amino;

provided that the compound is not N-(((5R,8S)-3-(2,6-difluorophenyl)-9,9-dimethyl-5,6,7,8-tetrahydro-5,8-methanocinnolin-8-yl)methyl)-N-ethyl-5-methylisoxazole-3-carboxamide.

In certain embodiments, the subject compound is of formula I provided that when X is —C(O)—, Y is methylene, Z is a bond, $R^1$ and $R^2$ are fluoro, $R^3$ is hydrogen, $R^4$ is ethyl, then A is not oxazol-3-yl with methyl at the 5-position.

In certain embodiments, A is:
a five or six membered hetereoaryl selected from: oxazolyl; isoxazolyl; oxadiazolyl; thiazolyl; isothiazolyl; thiadiazolyl; triazolyl; pyrrolyl; pyrazolyl; imidazolyl; tetrazolyl; pyridinyl; pyrimidinyl; pyrazinyl; pyridazinyl; and triazinyl;
a five or six membered heterocyclyl selected from: oxetanyl; azetidinyl; azepinyl; pyrrolidinyl; piperidinyl; piperazinyl; imidazolidinyl; tetrahydrofuranyl; tetrahydropyranyl; tetrahydrothienyl, 1,1-dioxo-tetrahydrothienyl; morpholinyl; thiomorpolinyl; and 1,1-dioxo-thiomorpholinyl; or phenyl;

In certain embodiments, A is:
a five or six membered hetereoaryl selected from: oxazolyl; isoxazolyl; oxadiazolyl; thiazolyl; isothiazolyl; thiadiazolyl; triazolyl; pyrrolyl; pyrazolyl; imidazolyl; tetrazolyl; pyridinyl; pyrimidinyl; pyrazinyl; pyridazinyl; and triazinyl; or
phenyl.

In certain embodiments, A is a five or six membered hetereoaryl selected from: oxazolyl; isoxazolyl; oxadiazolyl; thiazolyl; isothiazolyl; thiadiazolyl; triazolyl; pyrrolyl; pyrazolyl; imidazolyl; tetrazolyl; pyridinyl; pyrimidinyl; pyrazinyl; pyridazinyl; and triazinyl.

In certain embodiments, A is a bicyclic heteroaryl selected from: indolyl; indazolyl; isoindolyl; benzoxazinyl; benzoxazolyl; benzothiazolyl; benzimidazolyl; benzotriazinyl; pyrazolo[1,5-a]pyrimidinyl; 3H-imidazo[4,5-b]pyridinyl; and quinazolinyl.

In certain embodiments, A is a five or six membered heterocyclyl selected from: oxetanyl; azetidinyl; azepinyl; pyrrolidinyl; piperidinyl; piperazinyl; imidazolidinyl; tetrahydrofuranyl; tetrahydropyranyl; tetrahydrothienyl, 1,1-dioxo-tetrahydrothienyl; morpholinyl; thiomorpolinyl; and 1,1-dioxo-thiomorpholinyl.

In certain embodiments, A is phenyl.
In certain embodiments, A is $C_{3-6}$cycloalkyl.
In certain embodiments, A is a five or six membered hetereoaryl selected from: oxazolyl; isoxazolyl; oxadiazolyl; thiazolyl; triazolyl; pyrrolyl; pyrazolyl; imidazolyl; tetrazolyl; pyridinyl; pyrimidinyl; pyrazinyl; and pyridazinyl.

In certain embodiments, A is a five or six membered heterocyclyl selected from: oxetanyl; azetidinyl; pyrrolidinyl; piperidinyl; tetrahydrofuranyl; tetrahydropyranyl; tetrahydrothienyl, 1,1-dioxo-tetrahydrothienyl; and morpholinyl.

In certain embodiments, A is oxazolyl.
In certain embodiments, A is isoxazolyl.
In certain embodiments, A is oxadiazolyl.
In certain embodiments, A is thiazolyl.
In certain embodiments, A is isothiazolyl.
In certain embodiments, A is thiadiazolyl.
In certain embodiments, A is triazolyl.
In certain embodiments, A is pyrrolyl.
In certain embodiments, A is pyrazolyl.
In certain embodiments, A is imidazolyl.
In certain embodiments, A is tetrazolyl.
In certain embodiments, A is pyridinyl.
In certain embodiments, A is pyrimidinyl.
In certain embodiments, A is pyrazinyl.
In certain embodiments, A is pyridazinyl.
In certain embodiments, A is triazinyl.
In certain embodiments, A is indolyl.
In certain embodiments, A is indazolyl.
In certain embodiments, A is isoindolyl.
In certain embodiments, A is benzoxazinyl.
In certain embodiments, A is benzoxazolyl.
In certain embodiments, A is benzothiazolyl.
In certain embodiments, A is benzimidazolyl.
In certain embodiments, A is benzotriazinyl.
In certain embodiments, A is pyrazolo[1,5-a]pyrimidinyl.
In certain embodiments, A is 3H-imidazo[4,5-b]pyridinyl.
In certain embodiments, A is quinazolinyl.
In certain embodiments, A is oxetanyl.
In certain embodiments, A is azetidinyl.
In certain embodiments, A is azepinyl.
In certain embodiments, A is pyrrolidinyl.
In certain embodiments, A is piperidinyl.
In certain embodiments, A is piperazinyl.
In certain embodiments, A is imidazolidinyl.
In certain embodiments, A is tetrahydrofuranyl.
In certain embodiments, A is tetrahydropyranyl.

In certain embodiments, A is tetrahydrothienyl.
In certain embodiments, A is 1,1-dioxo-tetrahydrothienyl.
In certain embodiments, A is morpholinyl.
In certain embodiments, A is thiomorpholinyl.
In certain embodiments, A is 1,1-dioxo-thiomorpholinyl.
In certain embodiments, X is —C(O)—.
In certain embodiments, X is —SO$_2$—.
In certain embodiments, Y is a bond.
In certain embodiments, Y is C$_{1-6}$alkylene.
In certain embodiments, Y is halo-C$_{1-6}$alkylene.
In certain embodiments, Y is methylene.
In certain embodiments, Y is —CH$_2$—.
In certain embodiments, Z is a bond.
In certain embodiments, Z is C$_{1-6}$alkylene.
In certain embodiments, Z is halo-C$_{1-6}$alkylene.
In certain embodiments, Z is hydroxy-C$_{1-6}$alkylene;
In certain embodiments, Z is —O—C$_{1-6}$alkylene.
In certain embodiments, Z is —NH—C$_{1-6}$alkylene.
In certain embodiments, Z is methylene.
In certain embodiments, m is 0.
In certain embodiments, m is 1.
In certain embodiments, m is 2.
In certain embodiments, m is 0 or 1.
In certain embodiments, R$^1$ is fluoro.
In certain embodiments, R$^2$ is hydrogen.
In certain embodiments, R$^2$ is halo.
In certain embodiments, R$^2$ is fluoro.
In certain embodiments, R$^3$ is hydrogen.
In certain embodiments, R$^3$ is halo.
In certain embodiments, R$^3$ is C$_{1-6}$alkyl.
In certain embodiments, R$^4$ is:
C$_{1-6}$alkyl;
halo-C$_{1-6}$alkyl;
hydroxy-C$_{1-6}$alkyl;
cyano-C$_{1-6}$alkyl; or
C$_{3-6}$cycloalkyl which may be unsubstituted or substituted once or twice with R$^a$.

In certain embodiments, R$^4$ is hydrogen;
In certain embodiments, R$^4$ is C$_{1-6}$alkyl;
In certain embodiments, R$^4$ is halo-C$_{1-6}$alkyl;
In certain embodiments, R$^4$ is hydroxy-C$_{1-6}$alkyl;
In certain embodiments, R$^4$ is cyano-C$_{1-6}$alkyl;
In certain embodiments, R$^4$ is —C$_{1-6}$alkylene-C(O)R$^c$;
In certain embodiments, R$^4$ is —C$_{1-6}$alkylene-heteroaryl wherein the heteroaryl is oxazolyl; isoxazolyl; oxadiazolyl; thiazolyl; isothiazolyl; thiadiazolyl; triazolyl; pyrrolyl; pyrazolyl; imidazolyl; tetrazolyl, each of which may be unsubstituted or substituted once with R$^a$.
In certain embodiments, R$^4$ is C$_{3-6}$cycloalkyl which may be unsubstituted or substituted once or twice with R$^a$.
In certain embodiments, R$^4$ is C$_{3-6}$cycloalkyl-C$_{1-6}$alkyl wherein the C$_{3-6}$cycloalkyl may be unsubstituted or substituted once or twice with R$^a$.
In certain embodiments, R$^4$ is ethyl.
In certain embodiments, R$^4$ is difluoroethyl.
In certain embodiments, R$^4$ is cyanoethyl.
In certain embodiments, R$^5$ is C$_{1-6}$alkyl;
In certain embodiments, R$^5$ is C$_{1-6}$alkyloxy;
In certain embodiments, R$^5$ is halo-C$_{1-6}$alkyl;
In certain embodiments, R$^5$ is halo-C$_{1-6}$alkoxy5
In certain embodiments, R$^5$ is halo.
In certain embodiments, R$^5$ is hydroxyl.
In certain embodiments, R$^5$ is oxo.
In certain embodiments, R$^5$ is cyano.
In certain embodiments, R$^5$ is cyano-C$_{1-6}$alkyl.
In certain embodiments, R$^5$ is C$_{1-6}$alkylsulfonyl.
In certain embodiments, R$^5$ is C$_{1-6}$alkylsulfonylamino.

In certain embodiments, R$^5$ is C$_{3-6}$cycloalkylsulfonyl.
In certain embodiments, R$^5$ is C$_{3-6}$cycloalkylsulfonylamino.
In certain embodiments, R$^5$ is C$_{1-6}$alkylsulfonyl.
In certain embodiments, R$^5$ is C$_{3-6}$cycloalkyl-C$_{1-6}$alkylsulfonylamino.
In certain embodiments, R$^5$ is C$_{1-6}$alkylsulfonyl-C$_{1-6}$alkyl.
In certain embodiments, R$^5$ is C$_{1-6}$alkylsulfonyl-C$_{1-6}$alkyl.
In certain embodiments, R$^5$ is C$_{1-6}$alkylsulfonyl-C$_{1-6}$alkyl.
In certain embodiments, R$^5$ is amino.
In certain embodiments, R$^5$ is aminocarbonyl.
In certain embodiments, R$^5$ is aminosulfonyl.
In certain embodiments, R$^5$ is C$_{1-6}$alkylcarbonyl.
In certain embodiments, R$^5$ is C$_{1-6}$alkylcarbonylamino.
In certain embodiments, R$^5$ is aminocarbonylamino.
In certain embodiments, R$^5$ is C$_{1-6}$alkyloxycarbonyl.
In certain embodiments, R$^5$ is C$_{1-6}$alkylaminosulfonyl.
In certain embodiments, R$^5$ is phenyl which may be unsubstituted or substituted once or twice with R$^b$;
In certain embodiments, R$^5$ is heteroaryl selected from: pyridinyl pyrimidinyl; pyrazinyl triazinyl; pyrazolyl; imidazolyl; oxazolyl; isoxazolyl; oxadiazolyl; and tetrazolyl; each of which may be unsubstituted or substituted once or twice with R$^a$.
In certain embodiments, R$^5$ is heteroaryl-C$_{1-6}$alkyl wherein the heteroaryl is selected from: pyridinyl pyrimidinyl; pyrazinyl triazinyl; pyrazolyl; imidazolyl; oxazolyl; oxadiazolyl; isoxazolyl; and tetrazolyl; each of which may be unsubstituted or substituted once or twice with R$^a$.
In certain embodiments, R$^5$ is heteroaryl-C$_{1-6}$alkoxy wherein the heteroaryl is selected from: pyridinyl pyrimidinyl; pyrazinyl triazinyl; pyrazolyl; imidazolyl; oxazolyl; oxadiazolyl; isoxazolyl; and tetrazolyl; each of which may be unsubstituted or substituted once or twice with R$^a$.
In certain embodiments, R$^5$ is heterocyclyl selected from: morpholinyl; pyrrolidinyl; oxetanyl; and azetidinyl each of which may be unsubstituted or substituted once or twice with R$^b$.
In certain embodiments, R$^a$ is C$_{1-6}$alkyl.
In certain embodiments, R$^a$ is C$_{3-6}$cycloalkyl.
In certain embodiments, R$^a$ is halo-C$_{1-6}$alkyl.
In certain embodiments, R$^a$ is halo.
In certain embodiments, R$^a$ is hydroxyl.
In certain embodiments, R$^a$ is hydroxyl-C$_{1-6}$alkyl. or
In certain embodiments, R$^a$ is oxo.
In certain embodiments, R$^b$ is C$_{1-6}$alkyl.
In certain embodiments, R$^b$ is C$_{1-6}$alkylcarbonyl.
In certain embodiments, R$^b$ is C$_{1-6}$alkylsulfonyl.
In certain embodiments, R$^b$ is halo-C$_{1-6}$alkyl.
In certain embodiments, R$^b$ is halo.
In certain embodiments, R$^b$ is hydroxyl.
In certain embodiments, R$^b$ is hydroxyl-C$_{1-6}$alkyl. or
In certain embodiments, R$^b$ is oxo.
In certain embodiments, R$^c$ is hydroxyl.
In certain embodiments, is C$_{1-6}$alkoxy.
In certain embodiments, R$^b$ is amino.
In certain embodiments, the compounds of the invention may be of formula Ia or Ib

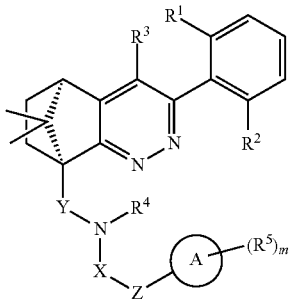

Ia

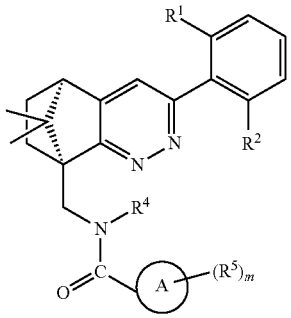

IIa

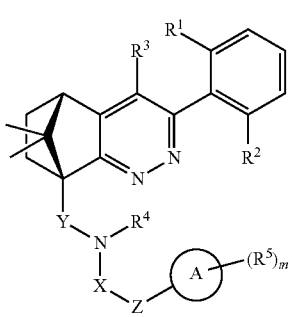

Ib

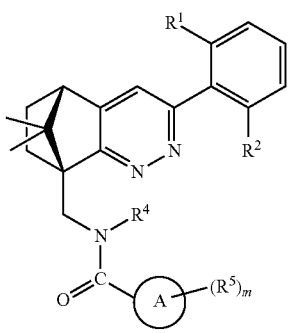

IIb wherein m, A, X, Y, Z, $R^1$, $R^2$, $R^3$, $R^4$ and $R^5$ are as defined herein.

In certain embodiments, the compounds of the invention are of formula Ia.

In certain embodiments, the compounds of the invention are of formula Ib.

In certain embodiments, the compounds of the invention are of formula II wherein m, A, $R^1$, $R^2$, $R^4$ and $R^5$ are as defined herein.

In certain embodiments, the compounds of the invention are of formula IIa.

In certain embodiments, the compounds of the invention are of formula IIb.

In certain embodiments, the compounds of the invention are of formula III

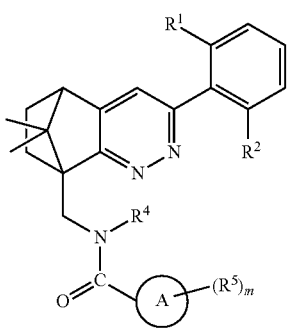

II

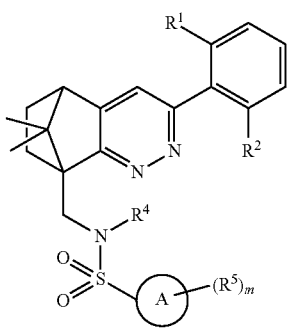

III wherein m, A, $R^1$, $R^2$, $R^4$ and $R^5$ are as defined herein.

In certain embodiments, the compounds of the invention may be of formula IIa or IIb wherein m, A, $R^1$, $R^2$, $R^4$ and $R^5$ are as defined herein.

In certain embodiments, the compounds of the invention may be of formula IIIa or IIIb

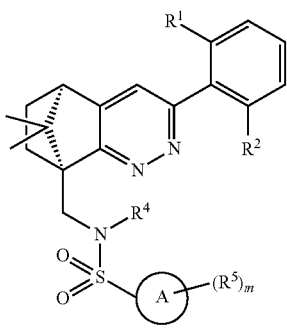

IIIa

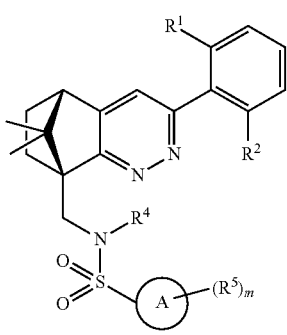

IIIa wherein m, A, $R^1$, $R^2$, $R^4$ and $R^5$ are as defined herein.

In certain embodiments, the compounds of the invention are of formula IIIa.

In certain embodiments, the compounds of the invention are of formula IIIb.

Methods

The invention also provides a method for treating a disease or condition mediated by or otherwise associated with the RORc receptor, the method comprising administering to a subject in need thereof an effective amount of a compound of the invention.

The disease may be arthritis such as rheumatoid arthritis or osteoarthritis.

The disease may be asthma or COPD.

The disease may be psoriasis.

The disease may be muscular distrophy.

The compounds may be used for treatment of cancer and inhibition or tumor growth, including prostate cancer and castrate-resistant prostate cancer.

Representative compounds in accordance with the methods of the invention are shown in the experimental examples below.

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein may be conducted under an inert atmosphere at atmospheric pressure at a reaction temperature range of from about −78° C. to about 150° C., for example, from about 0° C. to about 125° C., or conveniently at about room (or ambient) temperature, e.g., about 20° C.

Scheme A below illustrates one synthetic procedure usable to prepare specific compounds of formula I, wherein R is lower alkyl and m, n, A, $R^1$, $R^2$, $R^4$ and $R^5$ are as defined herein.

SCHEME A

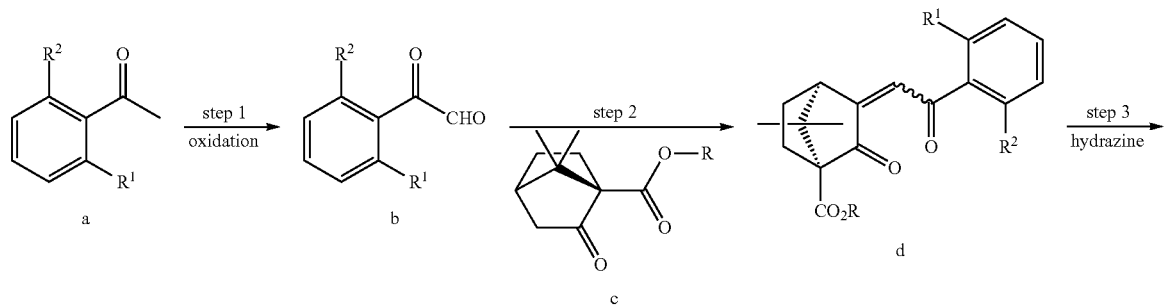

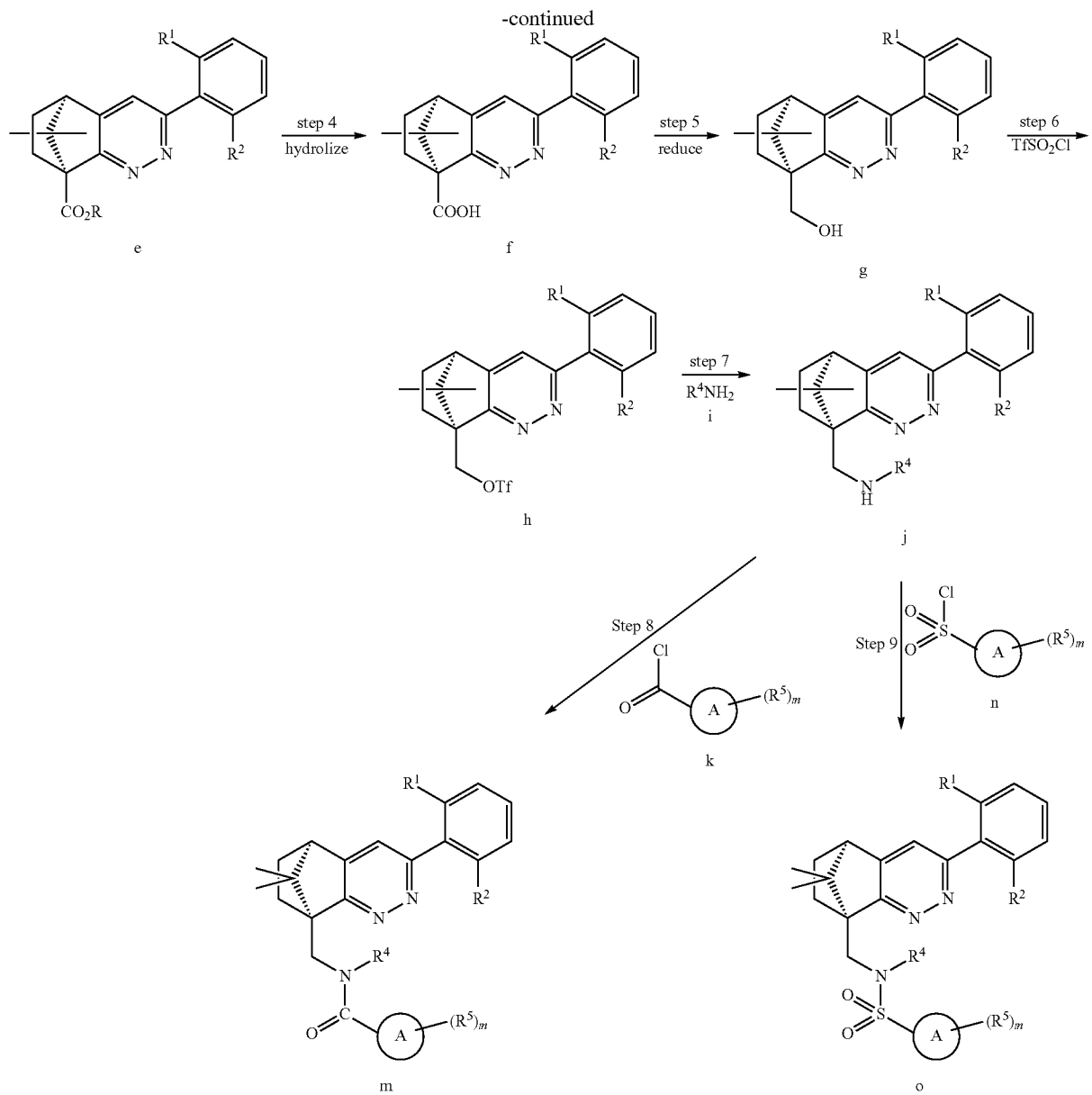

In step 1 of Scheme A, benzophenone compound a undergoes oxidation to afford benzaldehyde compound b. This oxidation may be achieved, for example, using selenium dioxide under polar protic solvent conditions. In step 2, benzaldehyde compound b is reacted with camphor carboxylate ester c to yield camphor ketophenyl compound d. Compound d is then reacted with hydrazine in step 3 to effect a cyclization reaction and provide cinnoline carboxylate ester compound e. Ester compound e then undergoes hydrolysis in step 4 to yield the corresponding carboxy cinnoline compound f. In step 5 carboxycinnoline compound f undergoes reduction to give the corresponding alcohol compound g. Compound g is treated with trifluoromethanesulfonyl chloride in step 6 to introduce a triflate leaving group on compound h. Triflated compound h is reacted with amine i in step 7 to afford amino cinnoline compound j. Amino cinnoline j may then be reacted with acid halide compound k in step 8 to give carboxamide compound m, or alternatively may be reacted with acid halide n in step 9 to give sulfonamide compound o. Cinnoline compounds m and o are compounds of formula I in accordance with the invention.

Many variations on the procedures of Scheme A are possible and will suggest themselves to those skilled in the art. In step 8, for example, acid halide may be replaced with the corresponding carboxylic acid or carboxylate salt, and the amide formation may be facilitated via use of HATU or like amide formation reagent. Specific details for producing compounds of the invention are described in the Examples below.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, for example 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. A particular manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets may contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations may be in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

Utility

The compounds of the invention are useful for treatment of immune disorders generally. The compounds may be used for treatment of arthritis, including rheumatoid arthritis, osteoarthritis, psoriatic arthritis, septic arthritis, spondyloarthropathies, gouty arthritis, systemic lupus erythematosus and juvenile arthritis, osteoarthritis, and other arthritic conditions.

The compounds may be used for treatment of respiratory disorders such as chronic obstructive pulmonary disease (COPD), asthma, bronchospasm, and the like.

The compounds may be used for treatment of gastrointestinal disorder ("GI disorder") such as Irritable Bowel Syndrome (IBS), Inflammatory Bowel Disease (IBD), biliary colic and other biliary disorders, renal colic, diarrhea-dominant IBS, pain associated with GI distension, and the like.

The compounds may be used for treatment of pain conditions such as inflammatory pain; arthritic pain, surgical pain; visceral pain; dental pain; premenstrual pain; central pain; pain due to burns; migraine or cluster headaches; nerve injury; neuritis; neuralgias; poisoning; ischemic injury; interstitial cystitis; cancer pain; viral, parasitic or bacterial infection; post-traumatic injury; or pain associated with irritable bowel syndrome.

The compounds may be used for treatment of muscular sclerosis, Sjogren's disease, lupus, and pulmonary fibrosis.

General Experimental

LCMS Methods:

High Pressure Liquid Chromatography-Mass Spectrometry (LCMS) experiments to determine retention times (RT) and associated mass ions were performed using one of the following methods:

Method A: Compounds were analyzed using the following conditions: Experiments were performed on a Waters ZMD single quadrupole mass spectrometer linked to a Hewlett-Packard HP1100 LC system with UV diode array detector and 100 position autosampler. The spectrometer has an electrospray source operating in positive and negative ion mode. This system uses a Phenomenex Luna 3 µm C18(2) 30×4.6 mm column at ambient temperature and a 2.0 mL/min flow rate. The initial solvent system was 95% water containing 0.1% formic acid (solvent A) and 5% acetonitrile containing 0.1% formic acid (solvent B) for the first 0.5 min followed by a gradient up to 5% solvent A and 95% solvent B over the next 4 min. This was maintained for 1 min before returning to 95% solvent A and 5% solvent B over the next 0.5 min. Total run time was 6 min.

Method B: Compounds were analysed using the following conditions: Experiments were performed on a Waters Micromass ZQ2000 quadrupole mass spectrometer linked to a Waters Acquity UPLC system with a PDA UV detector. The spectrometer has an electrospray source operating in positive and negative ion mode. This system uses an Acquity BEH C18 1.7 µm 100×2.1 mm column, maintained at 40° C. or an Acquity BEH Shield RP18 1.7 µm 100×2.1 mm column, maintained at 40° C. and a 0.4 mL/min flow rate. The initial solvent system was 95% water containing 0.1% formic acid (solvent A) and 5% acetonitrile containing 0.1% formic acid (solvent B) for the first 0.4 min followed by a gradient up to 5% solvent A and 95% solvent B over the next 5.6 min. This was maintained for 0.8 min before returning to 95% solvent A and 5% solvent B over the next 1.2 min. Total run time was 8 min.

NMR Methods:

$^1$H NMR spectra were recorded at ambient temperature or at 80° C. where indicated using one of the following machines: Varian Unity Inova (400 MHz) spectrometer with a triple resonance 5 mm probe, Bruker Avance DRX 400 (400 MHz) spectrometer with a triple resonance 5 mm probe, a Bruker Avance DPX 300 (300 MHz) equipped with a standard 5 mm dual frequency probe for detection of $^1$H and $^{13}$C, Bruker Fourier 300 MHz system equipped with a standard 5 mm $^1$H/$^{13}$C probe, a Bruker AVIII (400 MHz) using a BBI Broad Band Inverse 5 mm probe, or a Bruker AVIII (500 MHz) using a QNP (Quad Nucleus detect) 5 mm probe. Chemical shifts are expressed in ppm relative to an internal standard, tetramethylsilane (ppm=0.00). The following abbreviations have been used: br=broad signal, s=singlet, d=doublet, dd=double doublet, t=triplet, td=triplet doublet, dddd=doublet doublet doublet doublet, q=quartet, m=multiplet, or any combination thereof.

Microwave Reactor:

Microwave reactions were carried out using a Biotage® Initiator® in vials appropriate to the scale of the reaction and at the temperature and time described in the experimental details.

Purification Equipment:

Purifications were carried out using pre-packed silica gel cartridges either on a Teledyne ISCO CombiFlash® or Biotage® Isolera Four® or using compressed air to apply external pressure. Solvents and gradients shown in the experimental details were used.

Reverse Phase High Pressure Liquid Chromatography (HPLC) was used to purify compounds where indicated. Separation using gradient elution on a Phenomenex Gemini C18 column (250×21.2 mm, 5 μm) as stationary phase and using mobile phase indicated, operating at a 18 mL/min flow rate using a Gilson UV/Vis −155 dual channel detector and Gilson GX-271 automated liquid handler.

Phase separator cartridges are supplied by Biotage® as Isolute® phase separator cartridges.

LIST OF ABBREVIATIONS

AcOH Acetic acid
AIBN 2,2'-Azobis(2-methylpropionitrile)
Atm. Atmosphere
BOC tert-Butyloxycarbonyl group
(BOC)$_2$O Di-tert-butyl dicarbonate
CrO$_3$ Chromium(VI) oxide
CDCl$_3$ Deuterated chloroform
CCl$_4$ Carbon tetrachloride
DavePhos 2-Dicyclohexylphosphino-2'-(N,N-dimethylamino)biphenyl
DCM Dichloromethane/methylene chloride
DMA N,N-Dimethylacetamide
DIAD Diisopropyl azodicarboxylate
DIPEA Diisopropylethylamine
DMAP 4-Dimethylaminopyridine
DME 1,2-Dimethoxyethane
DMF N,N-Dimethylformamide
DMSO Dimethyl sulfoxide
DPPF 1,1'-Bis(diphenylphosphino)ferrocene
ES Electrospray
Et$_2$O Diethyl ether
Et$_3$N Triethylamine
EtOH Ethanol/Ethyl alcohol
EtOAc Ethyl acetate
H$_2$O Water
H$_2$SO$_4$ Sulfuric acid
HATU 2-(1H-7-Azabenzotriazol-1-yl)-1,1,3,3-tetramethyl uronium hexafluorophosphate methanaminium
HBTU O-Benzotriazol-1-yl-N,N,N',N'-tetramethyluronium hexafluorophosphate
HCO$_2$H Formic acid
HCl Hydrochloric acid
HOBT 1-Hydroxybenzotriazole
HPLC High pressure liquid chromatography
RP HPLC Reverse phase high pressure liquid chromatography
IBX 2-Iodoxybenzoic acid
IMS Industrial methylated spirit
KOH Potassium hydroxide
K$_2$CO$_3$ Potassium carbonate
LDA Lithium diisopropylamide
i-PrOH Isopropanol/isopropyl alcohol/propan-2-ol
i-PrOAc Isopropyl acetate
LCMS Liquid Chromatograph/Mass Spectroscopy
LiOH Lithium hydroxide
MgSO$_4$ Magnesium sulphate
MeOH Methanol/Methyl alcohol
MW Microwaves
NaH Sodium hydride
NaCl Sodium chloride
NaOH Sodium hydroxide
Na$_2$SO$_4$ Sodium sulfate
Na$_2$CO$_3$ Sodium carbonate
NaHCO$_3$ Sodium bicarbonate/Sodium hydrogen carbonate
NBS N-Bromosuccinimide
NH$_4$Cl Ammonium chloride
NMP 1-Methyl-2-pyrrolidinone
POCl$_3$ Phosphorus oxychloride
PhCH$_3$ Toluene
Pd$_2$(dba)$_3$ Tris(dibenzylideneacetone)dipalladium(O)
PSI Pound per square inch
RT Room temperature
sat. Saturated
SCX-2 Pre-packed Isolute® silica-based sorbent with a chemically bonded propylsulfonic acid functional group
TBDMS tert-Butyldimethylsilyl
TFA Trifluoroacetic acid
THF Tetrahydrofuran
TIPS Triisopropylsilyl
TLC Thin layer chromatography
XantPhos 4,5-Bis(diphenylphosphino)-9,9-dimethylxanthene Intermediate A: (1R)-5-(2,6-Fluorophenyl)-11,11-dimethyl-3,4-diazatricyclo[6.2.1.02,7]undeca-2(7),3,5-triene-1-carboxylic Acid

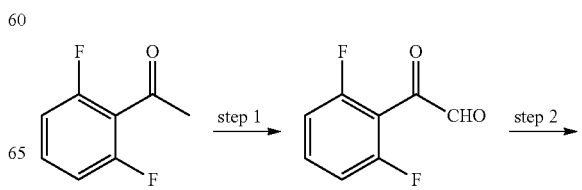

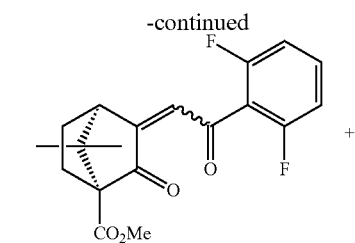

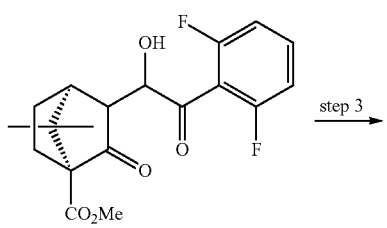

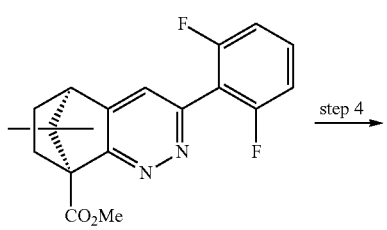

Step 1: 2-(2,6-Difluorophenyl)-2-oxoacetaldehyde

A mixture of selenium dioxide (111 g, 1000 mmol) in 1,4-dioxane/H$_2$O (500 mL/20 mL) at 55° C. was stirred for 30 min and then added 1-(2,6-difluorophenyl)ethanone (156 g, 1000 mmol). The mixture was refluxed for 20 h. The reaction was cooled to room temperature and filtered. The filtrate was concentrated under reduced pressure. The residue was purified by fractional distillation collecting the fractions between 90-94° C., under vacuum (~1 mm mercury), to afford the title compound as yellow oil (98.5 g). $^1$H NMR (500 MHz, DMSO-d$_6$): δ 9.48 (t, J=2.0 Hz, 1H), 7.79-7.76 (m, 1H), 7.33-7.29 (m, 2H); MS (ESI): [M+H]$^+$ 171.

Step 2: Methyl (1R)-3-[2-(2,6-difluorophenyl)-2-oxoethylidene]-7,7-dimethyl-2-oxobicyclo[2.2.1]heptane-1-carboxylate and (1R)-methyl 3-(2-(2,6-difluorophenyl)-1-hydroxy-2-oxoethyl)-7,7-dimethyl-2-oxobicyclo[2.2.1]heptane-1-carboxylate A solution of (1R)-methyl 7,7-dimethyl-2-oxobicyclo[2.2.1]heptane-1-carboxylate (19.6 g, 100 mmol) in anhydrous THF (100 mL) at −78° C. under nitrogen was added LDA (75 mL, 2 M in THF) drop-wise. The mixture was stirred at −78° C. for 1 h, and then 2-(2,6-difluorophenyl)-2-oxoacetaldehyde (20.4 g, 120 mmol) in THF (50 mL) was added. The mixture was stirred at −78° C. for 1 h and allowed to warm to room temperature. The reaction mixture was quenched with 1 N aqueous HCl and concentrated under reduced pressure. The residue was extracted with EtOAc. The combined organic layers were concentrated under reduced pressure and the residue was purified by chromatography on silica (1:30 EtOAc in petroleum ether) to afford the title compounds as yellow solids: methyl (1R)-3-[2-(2,6-difluorophenyl)-2-oxoethylidene]-7,7-dimethyl-2-oxobicyclo[2.2.1]heptane-1-carboxylate, (2.12 g), $^1$H NMR (500 MHz, DMSO-d$_6$): δ 7.72-7.66 (m, 1H), 7.29-7.26 (m, 2H), 6.99 (s, 1H), 3.72 (s, 3H), 3.30-3.29 (m, 1H), 2.45-2.39 (m, 1H), 2.24-2.17 (m, 1H), 1.79-1.74 (m, 1H), 1.43-1.38 (m, 1H), 1.07 (s, 3H), 1.03 (s, 3H); MS (ESI): [M+H]$^+$ 349.1; (1R)-methyl 3-(2-(2,6-difluorophenyl)-1-hydroxy-2-oxoethyl)-7,7-dimethyl-2-oxobicyclo[2.2.1]heptane-1-carboxylate, (5.51 g), $^1$H NMR (500 MHz, DMSO-d$_6$): δ 7.65-7.58 (m, 1H), 7.24-7.20 (m, 2H), 6.27 (d, J=7.5 Hz, 1H), 4.63-4.60 (m, 1H), 3.66 (s, 3H), 2.28-2.23 (m, 1H), 2.04-1.97 (m, 2H), 1.87-1.81 (m, 1H), 1.51-1.46 (m, 1H), 1.89 (s, 3H), 0.99 (s, 3H); MS (ESI): [M+H]$^+$ 367.1.

Step 3: Methyl (1R)-5-(2,6-fluorophenyl)-11,11-dimethyl-3,4-diazatricyclo[6.2.1.0 2.7]undeca-2(7),3,5-triene-1-carboxylate A mixture of methyl (1R)-3-[2-(2,6-difluorophenyl)-2-oxoethylidene]-7,7-dimethyl-2-oxobicyclo[2.2.1]heptane-1-carboxylate (2.09 g, 6.0 mmol) and hydrazine hydrochloride (4.08 g, 60 mmol) in butan-1-ol (100 mL) was heated at 135° C. for 20 h. The reaction mixture was concentrated under reduced pressure. The residue was dissolved in H$_2$O and extracted with EtOAc (20 mL×3). The combined organic fractions were concentrated under reduced pressure and the residue was purified by chromatography on silica (3:1 petroleum ether-EtOAc) to afford the title compound as yellow solid (1.78 g). MS (ESI): [M+H]$^+$ 345.1.

Following the procedure described above and starting with (1R)-methyl 3-(2-(2,6-difluorophenyl)-1-hydroxy-2-oxoethyl)-7,7-dimethyl-2-oxobicyclo[2.2.1]heptane-1-carboxylate (5.49 g, 15 mmol), the title compound was obtained as a yellow solid (4.39 g). MS (ESI): [M+H]$^+$ 345.1.

Step 4: (1R)-5-(2,6-Fluorophenyl)-11,11-dimethyl-3,4-diazatricyclo[6.2.1.0 2.7]undeca-2(7),3,5-triene-1-carboxylic Acid A mixture of the product from Step 3 (5.16 g, 15 mmol) and LiOH monohydrate (0.84 g, 63.5 mmol) in THF/H$_2$O (50 mL/5 mL) was heated at 30° C. for 20 h. The reaction mixture was cooled to room temperature and concentrated under reduced pressure. The residue was dissolved in H$_2$O and 1 N aqueous HCl added slowly until pH 3 was achieved. The mixture was extracted with EtOAc and the combined organic fractions were concentrated under reduced pressure to afford the title compound as yellow solid (4.21 g). $^1$H NMR (500 MHz, DMSO-d$_6$): δ 12.88 (s, 1H), 7.75 (s, 1H), 7.65-7.59 (m, 1H), 7.32-7.29 (m, 1H), 3.16-3.15 (m, 1H), 2.61-2.54 (m, 1H), 2.32-2.27 (m, 1H), 1.52-1.47 (m, 1H), 1.18-1.13 (m, overlap, 4H), 0.79 (s, 3H); MS (ESI): [M+H]$^+$ 331.1.

Intermediate B: [(1R,8R)-5-(2,6-Difluoro-phenyl)-11,11-dimethyl-3,4-diazatricyclo[6.2.1.0*2.7*]undeca-2(7),3,5-trien-1-yl]-methanol

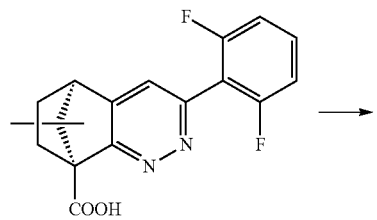

Isobutyl chloroformate (55 mg, 0.4 mmol) was added to a stirred, ice-cooled solution of (1R)-5-(2,6-fluorophenyl)-11,11-dimethyl-3,4-diazatricyclo[6.2.1.02.7]undeca-2(7),3,5-triene-1-carboxylic acid (110 mg, 0.33 mmol) and triethylamine (51 mg, 0.5 mmol) in THF and stirred for 15 min before being filtered and concentrated in vacuo. The residue was dissolved in EtOH (5 mL) and sodium borohydride (19 mg, 0.5 mmol) was added with stirring and cooling in ice. After 1 h, the solution was concentrated in vacuo and the residue dissolved in EtOAc and H$_2$O and the organic phase dried with Na$_2$SO$_4$, filtered and the filtrate concentrated in vacuo to afford the title compound as a white solid (101 mg). MS (ESI): [M+H]$^+$ 317.0.

Intermediate C: (1S,8R)-5-(2,6-Difluoro-phenyl)-11,11-dimethyl-3,4-diaza-tricyclo[6.2.1.0*2.7*]undeca-2(7),3,5-trien-1-yl amine

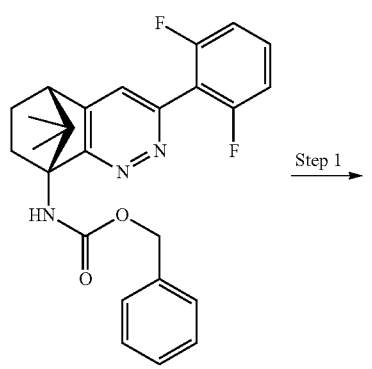

[(1S,8R)-5-(2,6-Difluoro-phenyl)-11,11-dimethyl-3,4-diaza-tricyclo[6.2.1.0*2.7*]undeca-2(7),3,5-trien-1-yl]-carbamic acid benzyl ester (598 mg, 1.37 mmol) was dissolved in a 33% solution of hydrogen bromide in acetic acid (3 mL). After stirring at RT for 45 min, the solvent was removed under vacuum and the residue azeotroped with toluene. The resulting solid was partitioned between cyclohexane and water. The aqueous layer was separated and basified with potassium carbonate, then extracted with EtOAc. The EtOAc extracts were dried over sodium sulfate, then the solvent removed under vacuum to yield the title compound as an off-white solid (371 mg, 1.23 mmol). LCMS RT=2.31 min, [M+H]$^+$ 302.3.

Intermediate D: 2-(methylsulfonylmethyl)oxazole-4-carboxylic acid

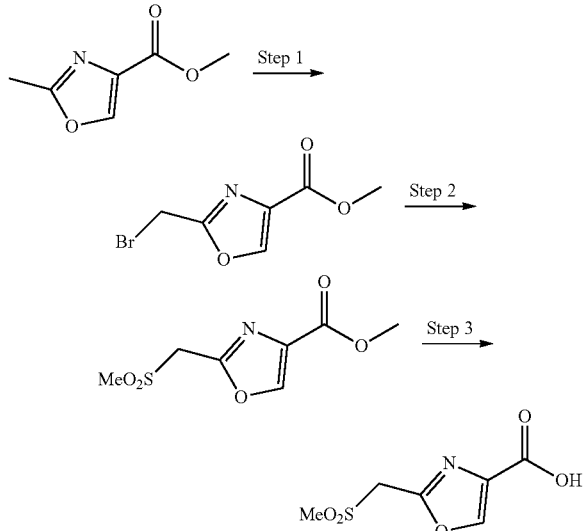

Step 1: Methyl 2-(bromomethyl)oxazole-4-carboxylate

To a solution of methyl 2-methyloxazole-4-carboxylate (5.00 g, 35.4 mmol) in CCl$_4$ (177 mL) was added AIBN (297 mg, 1.77 mmol) and NBS (6.31 g, 35.4 mmol). The resulting solution was heated at reflux for 2 h. The reaction mixture was cooled to room temperature and concentrated under reduced pressure. Purification by column chromatography (0-100% Heptanes-i-PrOAc) afforded the product (3.38 g, 15.4 mmol). $^1$H NMR (CDCl$_3$, 400 MHz): δ 8.25 (s, 1H), 4.47 (s, 2H), 3.93 (s, 3H); MS (ESI): m/z=221.9 [M+H]$^+$.

Step 2: Methyl 2-(methylsulfonylmethyl)oxazole-4-carboxylate

To a solution of the product from step 2 (3.38 g, 15.4 mmol) in DMF (77 mL) was added sodium methanesulfonate (2.61 mg, 23 mmol). The resulting solution was heated at 60° C. for 2 h. The reaction mixture was cooled to room temperature and concentrated under reduced pressure. Purification by column chromatography (0-100% Heptanes-i-PrOAc) afforded the product, which was used in the subsequent reaction. $^1$H NMR (CDCl$_3$, 400 MHz): δ 8.30 (s, 1H), 4.50 (q, J=0.9 Hz, 2H), 3.93 (s, 3H), 3.09 (d, J=0.9 Hz, 3H); MS (ESI): m/z=220.0 [M+H]$^+$.

Step 3:
2-(Methylsulfonylmethyl)oxazole-4-carboxylic Acid

To a solution of the product from step 3 in water (79 mL) and THF (79 mL) was added lithium hydroxide monohydrate (1.33 g, 31.5 mmol). The resulting solution was heated at 45° C. for 12 h. The reaction mixture was cooled to room temperature, then acidified to pH=2 with 1 N. The mixture was extracted with 10% MeOH in DCM. The organic extracts were dried over sodium sulfate, then the solvent removed under vacuum to yield the title compound (1.45 g, 7.07 mmol). $^1$H NMR (CD$_3$OD 400 MHz, 6/7 H): δ 8.30 (s, 1H), 4.50 (q, J=0.9 Hz, 2H), 3.93 (s, 3H), 3.09 (d, J=0.9 Hz, 3H) δ 8.57 (s, 1H), 4.78 (s, 2H), 3.15 (s, 3H).

Example 1: 3-Methyl-isoxazole-5-carboxylic acid [(1S,8R)-5-(2,6-difluoro-phenyl)-11,11-dimethyl-3,4-diaza-tricyclo[6.2.1.0*2.7*]undeca-2(7),3,5-trien-1-ylmethyl]-ethyl-amide

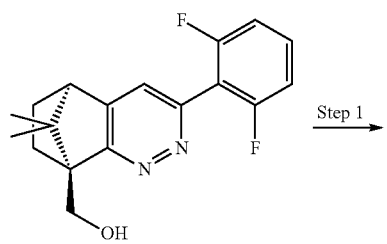

Step 1

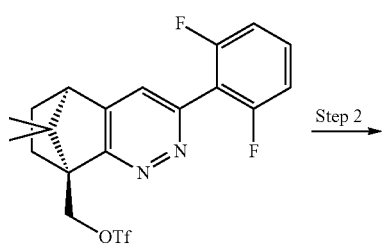

Step 2

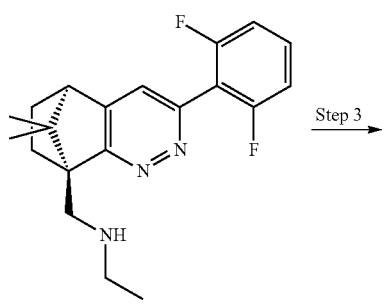

Step 3

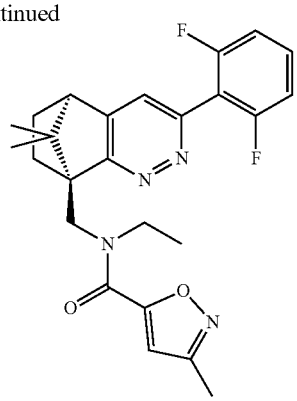

Step 1: Trifluoro-methanesulfonic Acid (1R,8R)-5-(2,6-difluoro-phenyl)-11,11-dimethyl-3,4-diaza-tricyclo[6.2.1.0*2.7*]undeca-2(7),3,5-trien-1-ylmethyl Ester Trifluoromethanesulfonic anhydride (2.12 g, 7.50 mmol) was added drop-wise to a stirred solution of [(1R,8R)-5-(2,6-difluoro-phenyl)-11,11-dimethyl-3,4-diazatricyclo[6.2.1.0*2.7*]undeca-2(7),3,5-trien-1-yl]-methanol (1.58 g, 5.00 mmol) and pyridine (2.0 mL) in CH$_2$Cl$_2$ at 0° C. The cooling bath was then removed and the mixture stirred for an additional 30 min. The mixture was then washed with water, filtered through a phase separation cartridge, and then concentrated in vacuo. The resulting residue was purified by flash chromatography (0-30% EtOAc-cyclohexane) to give the title compound as a pale colored solid (2.19 g). MS (ESI): [M+H]$^+$ 449.2.

Step 2: [(1S,8R)-5-(2,6-Difluoro-phenyl)-11,11-dimethyl-3,4-diaza-tricyclo[6.2.1.0*2.7*]undeca-2(7),3,5-trien-1-ylmethyl]-ethyl-amine A solution of the product from step 1 (2.19 g, 4.89 mmol) and ethylamine (15 mL, 30 mmol, 2 M in THF) in CH$_3$CN (15 mL) was stirred at room temperature for 18 h. The mixture was concentrated in vacuo and the residue partitioned between H$_2$O and EtOAc. The organic phase was dried (Na$_2$SO$_4$), filtered, and concentrated in vacuo to give the title compound as a brown oil (1.64 g). MS (ESI): [M+H]$^+$ 344.

Step 3: 3-Methyl-isoxazole-5-carboxylic Acid [(1S,8R)-5-(2,6-difluoro-phenyl)-11,11-dimethyl-3,4-diaza-tricyclo[6.2.1.0*2.7*]undeca-2(7),3,5-trien-1-ylmethyl]-ethyl-amide To a solution of the product from step 2 (57 mg, 0.17 mmol) and 5-methylisoxazole-3-carboxylic acid (23 mg, 0.18 mmol) in CH$_2$Cl$_2$ (2 mL) were added 1-ethyl-3-(3-dimethylaminopropyl)carbodiimide hydrochloride (38 mg, 0.20 mmol) and HOBT.H$_2$O (2.5 mg, 0.017 mmol) and the solution stirred at RT for 20 h. 5-Methylisoxazole-3-carboxylic acid (23 mg, 0.18 mmol) and 1-ethyl-3-(3-dimethyl-amino-propyl)carbodiimide hydrochloride (38 mg, 0.20 mmol) were added and the solution stirred at RT for 3 days. Water (2 mL) was added then the aqueous extracted with CH$_2$Cl$_2$ (2 mL). The combined organics were passed through a hydrophobic frit and concentrated in vacuo to leave a colourless residue. Flash chromatography (10-45%

EtOAc-cyclohexane) gave a clear gum (62 mg). Freeze-drying from acetonitrile-water (1:1, 3 mL) left a white solid (56 mg). NMR (400 MHz, DMSO-$d_6$) ~3:1 ratio rotamers: $^1$H NMR (400 MHz, CDCl3) 7.42-7.35 (2H, m), 7.03 (2H, dd, J=8.0, 8.0 Hz), 6.56 (1H, s), 4.47 (1H, d, J=14.3 Hz), 4.21-3.91 (3H, m), 2.97 (1H, d, J=4.0 Hz), 2.36-2.34 (6H, m), 1.37-1.23 (7H, m), 0.70 (3H, s); MS (ESI): [M+H]$^+$ 453.2.

Example 2: (1S,8R)-5-(2,6-Difluoro-phenyl)-11,11-dimethyl-3,4-diaza-tricyclo[6.2.1.0*2.7*]undeca-2(7),3,5-trien-1-ylamine

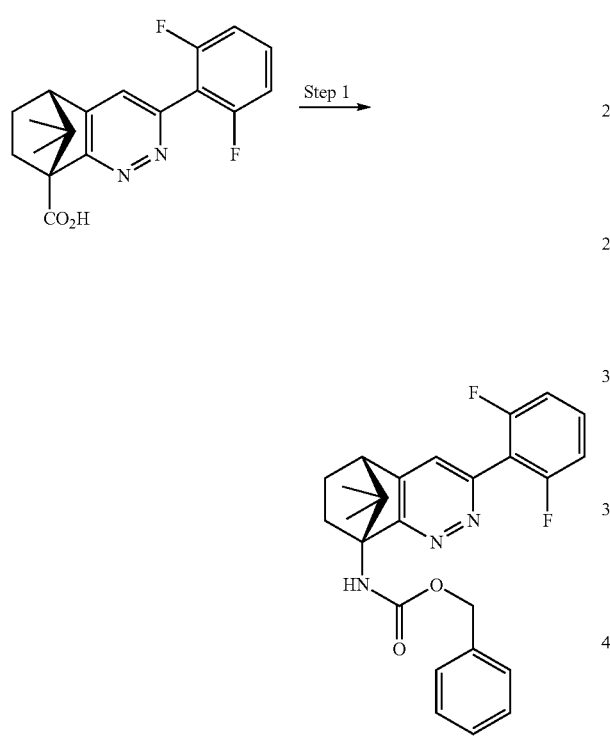

Step 1: [(1S,8S)-5-(2,6-Diphenyl-11,11-dimethyl-3,4-diaza-tricyclo[6.2.1.0*2.7*]undeca-2(7),3,5-trien-1-yl]-carbamic Acid Benzyl Ester A mixture of (1S,8S)-5-(2,6-difluoro-phenyl)-11,11-dimethyl-3,4-diaza-tricyclo[6.2.1.0*2.7*]undeca-2(7),3,5-triene-1-carboxylic acid (0.66 g, 2 mmol), diphenylphoshoryl azide (0.605 g, 2.2 mmol) and triethylamine (0.242 g, 2.4 mmol) in toluene (6 mL) was stirred and heated at 90° C. for one hour then cooled and benzyl alcohol (0.259 g, 2.4 mmol) was added. The resulting solution was warmed to 90° C. for four hours then cooled, diluted with EtOAc, washed with water and the organic phase dried (Na$_2$SO$_4$), filtered, and evaporated. The residue was purified by chromatography (0-40% EtOAc-cyclohexane) to give the title compound as a yellow gum (0.601 g). $^1$H NMR (CDCl$_3$, 300 MHz): δ 7.30-7.45 (m, 7H), 7.00-7.09 (m, 2H), 6.18 (br. s. 1H), 5.17 (s, 2H), 3.35-3.50 (m, 1H), 2.95 (d, J=4.5 Hz, 1H), 2.34-2.47 (m, 1H), 1.59 (s, 3H), 1.30-1.57 (m, 2H), 0.65 (s, 3H); LCMS ES$^+$ 436.3 [M+H]$^+$.

Example 3: N—((R)-1-(5R,8S)-3-(2,6-Difluorophenyl)-9,9-dimethyl-6,7-dihydro-5,8-methanocinnolin-8(5H)-yl)ethyl)-N-ethyloxazole-2-carboxamide and N—((S)-1-(5R,8S)-3-(2,6-Difluorophenyl)-9,9-dimethyl-6,7-dihydro-5,8-methanocinnolin-8(5H)-yl)ethyl)-N-ethyloxazole-2-carboxamide

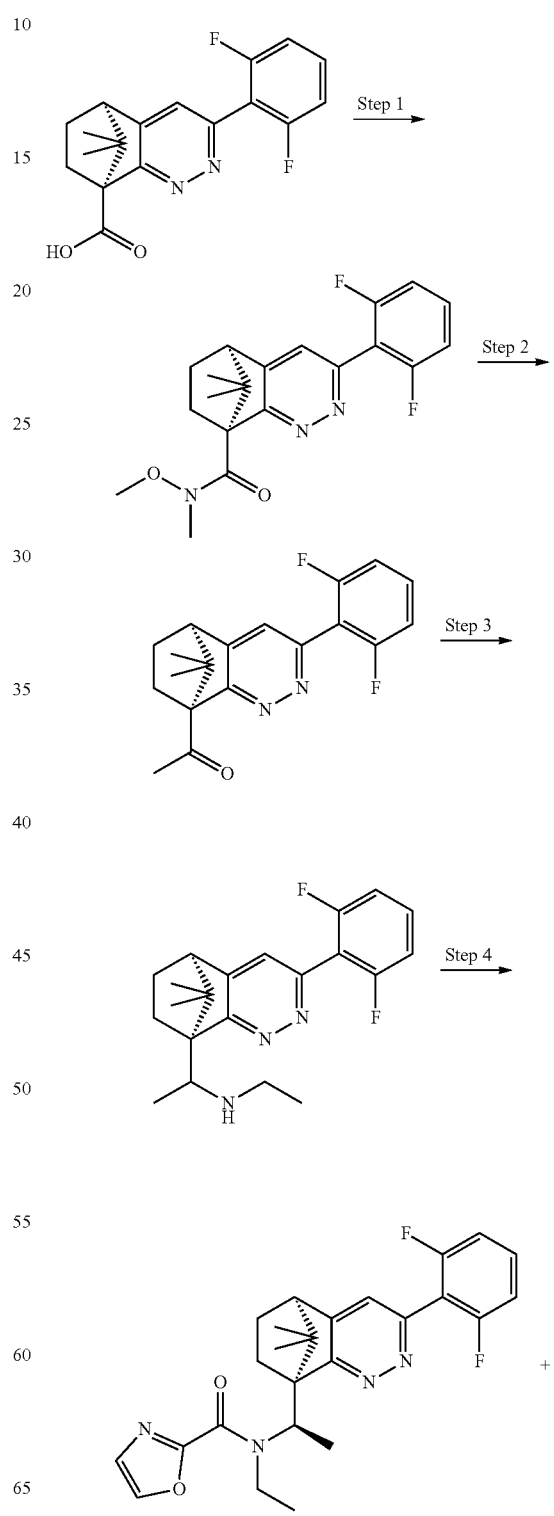

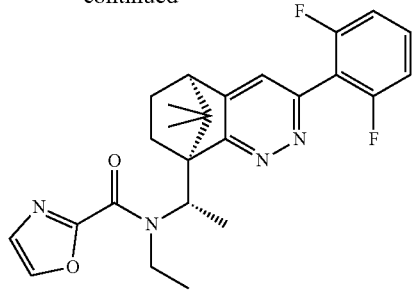

Step 1: (5R,8R)-3-(2,6-Difluorophenyl)-N-methoxy-N,9,9-trimethyl-6,7-dihydro-5,8-methanocinnoline-8 (5H)-carboxamide To a solution of (5R,8R)-3-(2,6-difluorophenyl)-9,9-dimethyl-6,7-dihydro-5,8-methanocinnoline-8(5H)-carboxylic acid (11.0 g, 33.3 mmol) in DCM was added oxalyl dichloride (4.20 mL, 50.0 mmol) and DMF (0.200 mL). The mixture was stirred at room temperature for 1 h. The reaction was concentrated in vacuo, then the crude was redissolved in DCM and Et$_3$N (9.30 mL, 66.6 mmol) was added. The mixture was cooled to 0° C. and N,O-dimethylhydroxylamine hydrochloride (3.25 g, 43.3 mmol) was added in portions. The mixture was allowed to warm up to room temperature and stirred for 40 min, quenched with saturated aqueous NH$_4$Cl. The organic phase was separated and dried over anhydrous Na$_2$SO$_4$, filtered and then concentrated under reduced pressure. The residue was purified by flash chromatography (0-50% EtOAc-petroleum ether) to give the title compound as a yellow solid (12.1 g). MS (ESI): m/z=374.2 [M+H]$^+$.

Step 2: 1-((5R,8R)-3-(2,6-Difluorophenyl)-9,9-dimethyl-6,7-dihydro-5,8-methanocinnolin-8 (5H)-yl)ethan-1-one To a solution of the product from step 1 (12.1 g, 32.4 mmol) in dry THF (100 mL) under nitrogen atmosphere was added methylmagnesium bromide (3M in Et$_2$O, 16.2 mL, 48.6 mmol) dropwise at 0° C. The mixture was stirred at room temperature for 0.5 h before being quenched with saturated aqueous NH$_4$Cl (150 mL) and extracted with EtOAc. The combined organics were dried over anhydrous Na$_2$SO$_4$, filtered and concentrated under reduced pressure. The residue was purified by flash chromatography (0-37% EtOAc-petroleum ether) to give the title compound as a yellow solid (8.4 g). MS (ESI): m/z=329.2 [M+H]$^+$.

Step 3: 1-(5R,8S)-3-(2,6-Difluorophenyl)-9,9-dimethyl-6,7-dihydro-5,8-methanocinnolin-8 (5H)-yl)-N-ethylethan-1-amine To a solution of the product from step 2 (7.00 g, 21.3 mmol) in CH$_2$Cl$_2$ (150 mL) at 0° C. was added ethanamine (2 M in THF, 32.0 mL, 63.9 mmol) and titanium tetraisopropanolate (18.2 g, 63.9 mmol), the reaction was stirred at 25° C. for 3 h. MeOH and sodium cyanoborohydride (4 g, 63.9 mmol) were added to the reaction and the mixture was stirred at room temperature for 12 h. The reaction was quenched with saturated aqueous NaHCO$_3$ and extracted with DCM (2×80 mL). The combined organics were dried over anhydrous Na$_2$SO$_4$, filtered and concentrated under reduced pressure. The residue was purified by flash chromatography (0-10% MeOH-DCM to give the title compound as a yellow solid (3.1 g). MS (ESI): m/z=358.2 [M+H]$^+$.

Step 4: N—((R)-1(5R,8S)-3-(2,6-Difluorophenyl)-9,9-dimethyl-6,7-dihydro-5,8-methanocinnolin-8 (5H)-yl)ethyl)-N-ethyloxazole-2-carboxamide and N—((S)-1-((5R,8S)-3-(2,6-Difluorophenyl)-9,9-dimethyl-6,7-dihydro-5,8-methanocinnolin-8(5H)-yl)ethyl)-N-ethyloxazole-2-carboxamide To a solution of the product from step 3 (200 mg, 0.560 mmol), sodium oxazole-2-carbonylate (151 mg, 1.10 mmol) and DIPEA (206 mg, 1.68 mmol) in DMF (5 mL) was added HATU (212 mg, 0.56 mmol) at 25° C. The reaction mixture was stirred at room temperature for 16 h before being diluted with DCM (100 mL). The organics were washed with water, dried over sodium sulfate and the solvent removed in vacuo. Purification by column chromatography (0-10% MeOH-DCM) afforded the product (220 mg) as a mixture of diastereomers. The mixture of diastereomers were purified by chiral separation (SFC: CO$_2$/MeOH{0.5% Ammonia (7M methanol)}=65/35) to give N—((R)-1-(5R,8S)-3-(2,6-Difluorophenyl)-9,9-dimethyl-6,7-dihydro-5,8-methanocinnolin-8(5H)-yl)ethyl)-N-ethyloxazole-2-carboxamide (98 mg) as a white solid and N—((S)-1-(5R,8S)-3-(2,6-Difluorophenyl)-9,9-dimethyl-6,7-dihydro-5,8-methanocinnolin-8 (5H)-yl)ethyl)-N-ethyloxazole-2-carboxamide (49.9 mg) as a white solid. MS (ESI): m/z=453.0 [M+H]$^+$.

Example 4: N-(((5R,8S)-3-(2,6-difluorophenyl)-9,9-dimethyl-5,6,7,8-tetrahydro-5,8-methanocinnolin-8-yl)methyl)-N-ethyl-2-((methylsulfonyl)methyl)oxazole-4-carboxamide

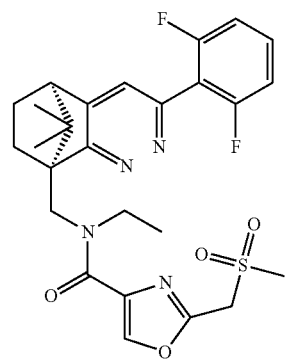 [SMILES: CCN(C[C@@]12CC[C@@H](/C(=C/C(=N)c3c(F)cccc3F)C1=N)C2(C)C)C(=O)c1coc(CS(C)(=O)=O)n1]

Using the procedure of step 4 of Example 3 above, but replacing sodium oxazole-2-carbonylate with 2-methylsulfonylmethyl)oxazole-4-carboxylic acid, N-(((5R,8S)-3-(2,6-difluorophenyl)-9,9-dimethyl-5,6,7,8-tetrahydro-5,8-methanocinnolin-8-yl)methyl)-N-ethyl-2-((methylsulfonyl)methyl)oxazole-4-carboxamide was prepared.

The above compounds, together with additional compounds made using the above procedure, are shown in Table 1 below, together with RORc IC$_{50}$ (micromolar) data for selected compounds determined using the assays described below.

TABLE 1

| | Structure | Name | IC$_{50}$ |
|---|---|---|---|
| 1 | 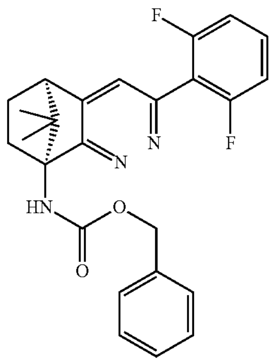 [SMILES: CC1(C)[C@H]2CC[C@]1(NC(=O)OCc1ccccc1)C(=N)/C2=C\C(=N)c1c(F)cccc1F] | benzyl ((5R,8R)-3-(2,6-difluorophenyl)-9,9-dimethyl-5,6,7,8-tetrahydro-5,8-methanocinnolin-8-yl)carbamate | 0.194 |
| 2 | 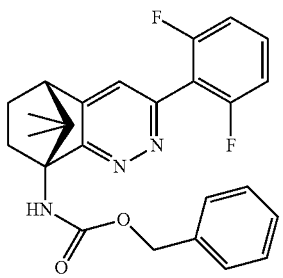 [SMILES: CC1(C)[C@@H]2CC[C@@]1(NC(=O)OCc1ccccc1)c1nnc(-c3c(F)cccc3F)cc12] | benzyl ((5S,8S)-3-(2,6-difluorophenyl)-9,9-dimethyl-5,6,7,8-tetrahydro-5,8-methanocinnolin-8-yl)carbamate | 0.222 |
| 3 | 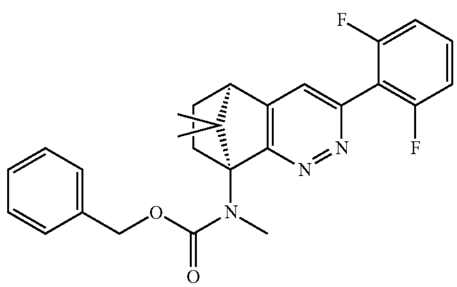 [SMILES: CN(C(=O)OCc1ccccc1)[C@@]12CC[C@@H](c3cc(-c4c(F)cccc4F)nnc31)C2(C)C] | benzyl ((5R,8R)-3-(2,6-difluorophenyl)-9,9-dimethyl-5,6,7,8-tetrahydro-5,8-methanocinnolin-8-yl)(methyl)carbamate | 0.0302 |
| 4 | 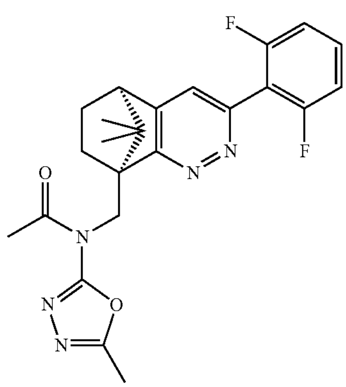 [SMILES: CC(=O)N(C[C@@]12CC[C@@H](c3cc(-c4c(F)cccc4F)nnc31)C2(C)C)c1nnc(C)o1] | N-(((5R,8S)-3-(2,6-difluorophenyl)-9,9-dimethyl-5,6,7,8-tetrahydro-5,8-methanocinnolin-8-yl)methyl)-N-(5-methyl-1,3,4-oxadiazol-2-yl)acetamide | 0.641 |
| 5 | 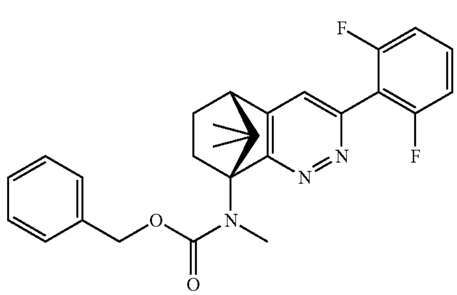 [SMILES: CN(C(=O)OCc1ccccc1)[C@]12CC[C@H](c3cc(-c4c(F)cccc4F)nnc31)C2(C)C] | benzyl ((5S,8S)-3-(2,6-difluorophenyl)-9,9-dimethyl-5,6,7,8-tetrahydro-5,8-methanocinnolin-8-yl)(methyl)carbamate | 0.479 |

TABLE 1-continued

| Structure | Name | IC$_{50}$ |
|---|---|---|
| 6 | N-(((5R,8S)-3-(2,6-difluorophenyl)-9,9-dimethyl-5,6,7,8-tetrahydro-5,8-methanocinnolin-8-yl)methyl)-N-ethyl-3-methylisoxazole-5-carboxamide | 0.0090 |
| 7 | N-(((5R,8S)-3-(2,6-difluorophenyl)-9,9-dimethyl-5,6,7,8-tetrahydro-5,8-methanocinnolin-8-yl)methyl)-N-(2-hydroxyethyl)-5-methylisoxazole-3-carboxamide | 0.0289 |
| 8 | N-(((5R,8S)-3-(2,6-difluorophenyl)-9,9-dimethyl-5,6,7,8-tetrahydro-5,8-methanocinnolin-8-yl)methyl)-N-(2-fluoroethyl)-5-methylisoxazole-3-carboxamide | 0.0094 |
| 9 | N-(((5R,8S)-3-(2,6-difluorophenyl)-9,9-dimethyl-5,6,7,8-tetrahydro-5,8-methanocinnolin-8-yl)methyl)-N-ethyl-2-methyloxazole-4-carboxamide | 0.0117 |

TABLE 1-continued

| | Structure | Name | IC$_{50}$ |
|---|---|---|---|
| 10 | 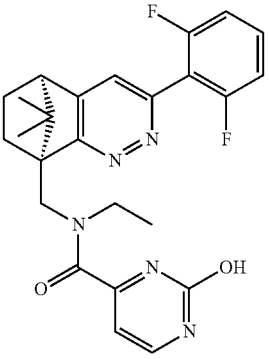 [SMILES: CCN(C[C@@]12CC[C@@H](c3cc(-c4c(F)cccc4F)nnc31)C2(C)C)C(=O)c1ccnc(O)n1] | N-(((5R,8S)-3-(2,6-difluorophenyl)-9,9-dimethyl-5,6,7,8-tetrahydro-5,8-methanocinnolin-8-yl)methyl)-N-ethyl-2-hydroxypyrimidine-4-carboxamide | 0.131 |
| 11 | 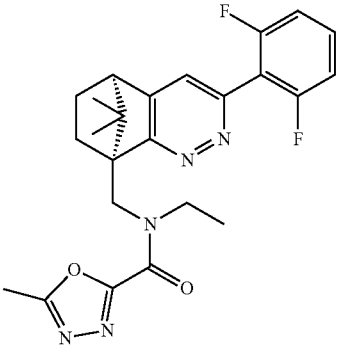 [SMILES: CCN(C[C@@]12CC[C@@H](c3cc(-c4c(F)cccc4F)nnc31)C2(C)C)C(=O)c1nnc(C)o1] | N-(((5R,8S)-3-(2,6-difluorophenyl)-9,9-dimethyl-5,6,7,8-tetrahydro-5,8-methanocinnolin-8-yl)methyl)-N-ethyl-5-methyl-1,3,4-oxadiazole-2-carboxamide | 0.0213 |
| 12 | 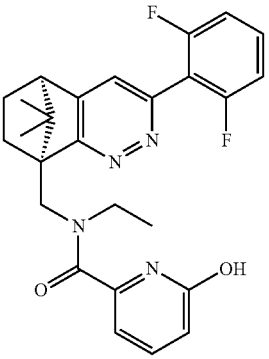 [SMILES: CCN(C[C@@]12CC[C@@H](c3cc(-c4c(F)cccc4F)nnc31)C2(C)C)C(=O)c1cccc(O)n1] | N-(((5R,8S)-3-(2,6-difluorophenyl)-9,9-dimethyl-5,6,7,8-tetrahydro-5,8-methanocinnolin-8-yl)methyl)-N-ethyl-6-hydroxypicolinamide | 0.070 |
| 13 | 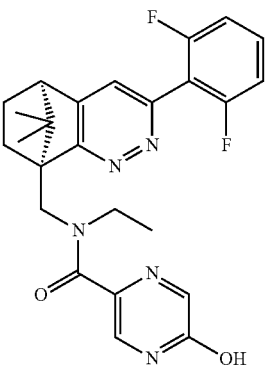 [SMILES: CCN(C[C@@]12CC[C@@H](c3cc(-c4c(F)cccc4F)nnc31)C2(C)C)C(=O)c1cnc(O)cn1] | N-(((5R,8S)-3-(2,6-difluorophenyl)-9,9-dimethyl-5,6,7,8-tetrahydro-5,8-methanocinnolin-8-yl)methyl)-N-ethyl-5-hydroxypyrazine-2-carboxamide | 0.047 |

TABLE 1-continued

| | Structure | Name | IC$_{50}$ |
|---|---|---|---|
| 14 | 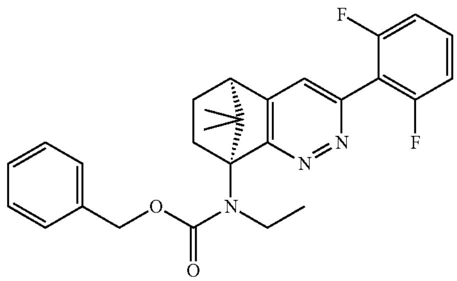 [SMILES: CCN(C(=O)OCc1ccccc1)[C@@]12CC[C@@H](c3cc(-c4c(F)cccc4F)nnc31)C2(C)C] | benzyl ((5R,8R)-3-(2,6-difluorophenyl)-9,9-dimethyl-5,6,7,8-tetrahydro-5,8-methanocinnolin-8-yl)(ethyl)carbamate | 0.0296 |
| 15 | 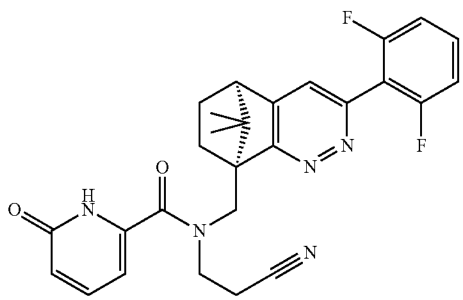 [SMILES: CC1(C)[C@H]2CC[C@]1(CN(CCC#N)C(=O)c1cccc(=O)[nH]1)c1nnc(-c3c(F)cccc3F)cc12] | N-(2-cyanoethyl)-N-(((5R,8S)-3-(2,6-difluorophenyl)-9,9-dimethyl-5,6,7,8-tetrahydro-5,8-methanocinnolin-8-yl)methyl)-6-oxo-1,6-dihydropyridine-2-carboxamide | 0.228 |
| 16 | 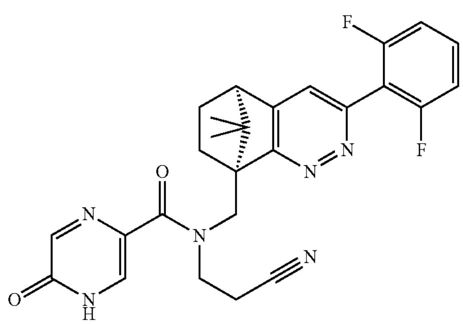 [SMILES: CC1(C)[C@H]2CC[C@]1(CN(CCC#N)C(=O)c1c[nH]c(=O)cn1)c1nnc(-c3c(F)cccc3F)cc12] | N-(2-cyanoethyl)-N-(((5R,8S)-3-(2,6-difluorophenyl)-9,9-dimethyl-5,6,7,8-tetrahydro-5,8-methanocinnolin-8-yl)methyl)-5-oxo-4,5-dihydropyrazine-2-carboxamide | 0.178 |
| 17 | 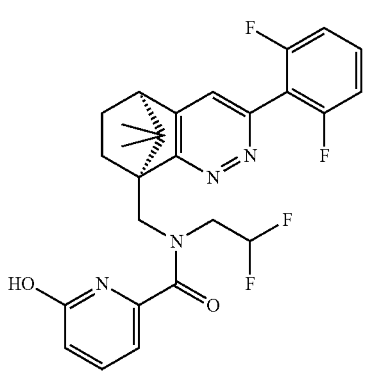 [SMILES: CC1(C)[C@H]2CC[C@]1(CN(CC(F)F)C(=O)c1cccc(O)n1)c1nnc(-c3c(F)cccc3F)cc12] | N-(2,2-difluoroethyl)-N-(((5R,8S)-3-(2,6-difluorophenyl)-9,9-dimethyl-5,6,7,8-tetrahydro-5,8-methanocinnolin-8-yl)methyl)-6-hydroxypicolinamide | 0.0513 |

TABLE 1-continued

| Structure | Name | IC$_{50}$ |
|---|---|---|
| 18 | N-(2,2-difluoroethyl)-N-(((5R,8S)-3-(2,6-difluorophenyl)-9,9-dimethyl-5,6,7,8-tetrahydro-5,8-methanocinnolin-8-yl)methyl)-5-hydroxypyrazine-2-carboxamide | 0.0244 |
| 19 | N-(((5R,8S)-3-(2,6-difluorophenyl)-9,9-dimethyl-5,6,7,8-tetrahydro-5,8-methanocinnolin-8-yl)methyl)-N-ethyl-6-hydroxynicotinamide | 0.049 |
| 20 | N-(((5R,8S)-3-(2,6-difluorophenyl)-9,9-dimethyl-5,6,7,8-tetrahydro-5,8-methanocinnolin-8-yl)methyl)-N-ethyl-2-hydroxyisonicotinamide | 0.055 |
| 21 | N-(((5R,8S)-3-(2,6-difluorophenyl)-9,9-dimethyl-5,6,7,8-tetrahydro-5,8-methanocinnolin-8-yl)methyl)-N-ethyl-2-hydroxypyrimidine-5-carboxamide | 0.061 |

TABLE 1-continued

| | Structure | Name | IC$_{50}$ |
|---|---|---|---|
| 22 | 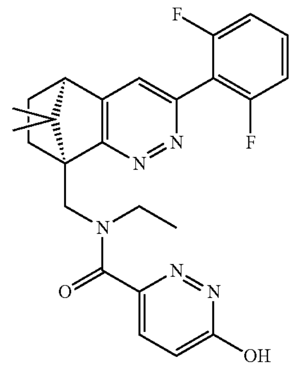 [SMILES: CCN(C[C@@]12CC[C@@H](c3cc(-c4c(F)cccc4F)nnc31)C2(C)C)C(=O)c1ccc(O)nn1] | N-(((5R,8S)-3-(2,6-difluorophenyl)-9,9-dimethyl-5,6,7,8-tetrahydro-5,8-methanocinnolin-8-yl)methyl)-N-ethyl-6-hydroxypyridazine-3-carboxamide | 0.0437 |
| 23 | 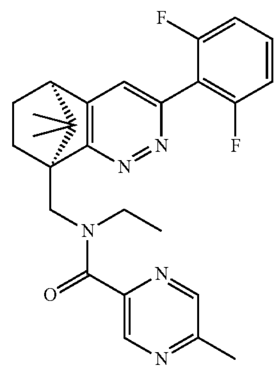 [SMILES: CCN(C[C@@]12CC[C@@H](c3cc(-c4c(F)cccc4F)nnc31)C2(C)C)C(=O)c1cnc(C)cn1] | N-(((5R,8S)-3-(2,6-difluorophenyl)-9,9-dimethyl-5,6,7,8-tetrahydro-5,8-methanocinnolin-8-yl)methyl)-N-ethyl-5-methylpyrazine-2-carboxamide | 0.0204 |
| 24 | 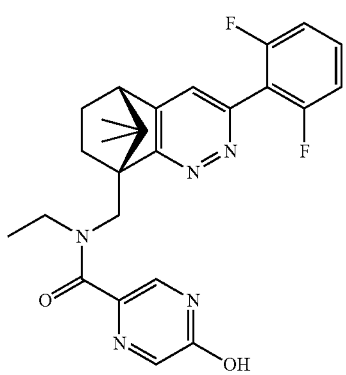 [SMILES: CCN(C[C@]12CC[C@H](c3cc(-c4c(F)cccc4F)nnc31)C2(C)C)C(=O)c1cnc(O)cn1] | N-(((5S,8R)-3-(2,6-difluorophenyl)-9,9-dimethyl-5,6,7,8-tetrahydro-5,8-methanocinnolin-8-yl)methyl)-N-ethyl-5-hydroxypyrazine-2-carboxamide | 0.274 |
| 25 | 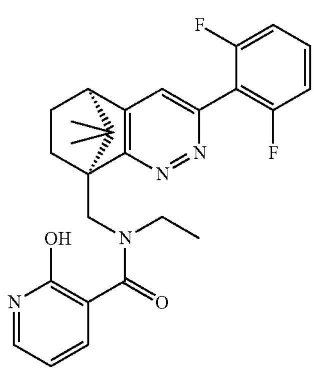 [SMILES: CCN(C[C@@]12CC[C@@H](c3cc(-c4c(F)cccc4F)nnc31)C2(C)C)C(=O)c1cccnc1O] | N-(((5R,8S)-3-(2,6-difluorophenyl)-9,9-dimethyl-5,6,7,8-tetrahydro-5,8-methanocinnolin-8-yl)methyl)-N-ethyl-2-hydroxynicotinamide | 0.184 |

TABLE 1-continued

| | Structure | Name | IC$_{50}$ |
|---|---|---|---|
| 26 | 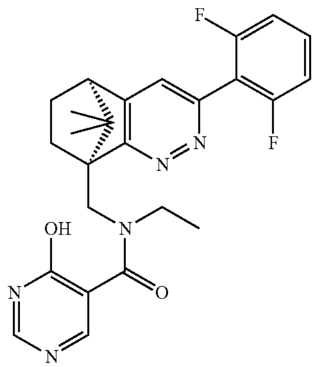 [SMILES: CCN(C[C@@]12CC[C@@H](c3cc(-c4c(F)cccc4F)nnc31)C2(C)C)C(=O)c1cncnc1O] | N-(((5R,8S)-3-(2,6-difluorophenyl)-9,9-dimethyl-5,6,7,8-tetrahydro-5,8-methanocinnolin-8-yl)methyl)-N-ethyl-4-hydroxypyrimidine-5-carboxamide | 0.221 |
| 27 | 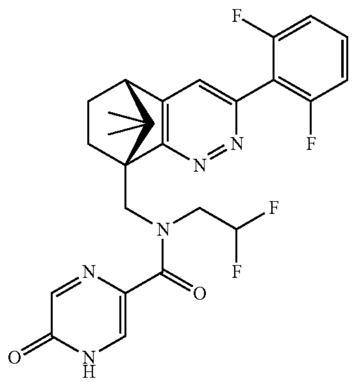 [SMILES: CC1(C)[C@@H]2CC[C@@]1(CN(CC(F)F)C(=O)c1c[nH]c(=O)cn1)c1nnc(-c3c(F)cccc3F)cc12] | N-(2,2-difluoroethyl)-N-(((5S,8R)-3-(2,6-difluorophenyl)-9,9-dimethyl-5,6,7,8-tetrahydro-5,8-methanocinnolin-8-yl)methyl)-5-oxo-4,5-dihydropyrazine-2-carboxamide | 0.356 |
| 28 | 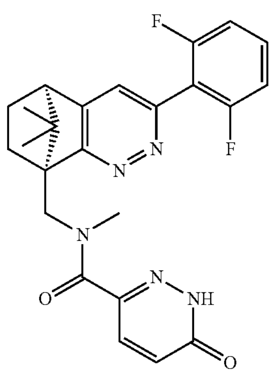 [SMILES: CN(C[C@@]12CC[C@@H](c3cc(-c4c(F)cccc4F)nnc31)C2(C)C)C(=O)c1ccc(=O)[nH]n1] | N-(((5R,8S)-3-(2,6-difluorophenyl)-9,9-dimethyl-5,6,7,8-tetrahydro-5,8-methanocinnolin-8-yl)methyl)-N-methyl-6-oxo-1,6-dihydropyridazine-3-carboxamide | 0.0371 |
| 29 | 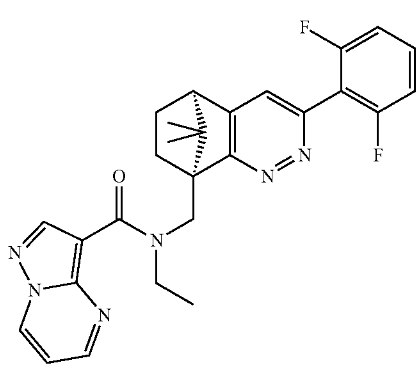 [SMILES: CCN(C[C@@]12CC[C@@H](c3cc(-c4c(F)cccc4F)nnc31)C2(C)C)C(=O)c1cnn2cccnc12] | N-(((5R,8S)-3-(2,6-difluorophenyl)-9,9-dimethyl-5,6,7,8-tetrahydro-5,8-methanocinnolin-8-yl)methyl)-N-ethylpyrazolo[1,5-a]pyrimidine-3-carboxamide | 0.0352 |

TABLE 1-continued

| Structure | Name | IC$_{50}$ |
|---|---|---|
| 30 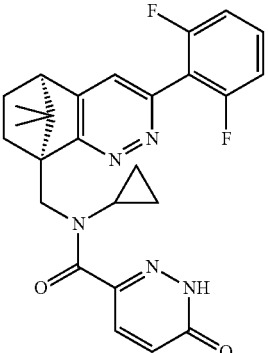 | N-cyclopropyl-N-(((5R,8S)-3-(2,6-difluorophenyl)-9,9-dimethyl-5,6,7,8-tetrahydro-5,8-methanocinnolin-8-yl)methyl)-6-oxo-1,6-dihydropyridazine-3-carboxamide | 0.167 |
| 31 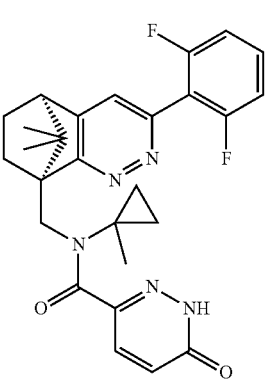 [SMILES: CC1(N(C[C@@]23CC[C@@H](c4cc(-c5c(F)cccc5F)nnc42)C3(C)C)C(=O)c2ccc(=O)[nH]n2)CC1] | N-(((5R,8S)-3-(2,6-difluorophenyl)-9,9-dimethyl-5,6,7,8-tetrahydro-5,8-methanocinnolin-8-yl)methyl)-N-(1-methylcyclopropyl)-6-oxo-1,6-dihydropyridazine-3-carboxamide | 0.0966 |
| 32 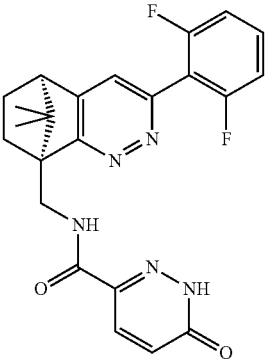 [SMILES: CC1(C)[C@H]2CC[C@]1(CNC(=O)c1ccc(=O)[nH]n1)c1nnc(-c3c(F)cccc3F)cc12] | N-(((5R,8S)-3-(2,6-difluorophenyl)-9,9-dimethyl-5,6,7,8-tetrahydro-5,8-methanocinnolin-8-yl)methyl)-6-oxo-1,6-dihydropyridazine-3-carboxamide | 0.23 |
| 33 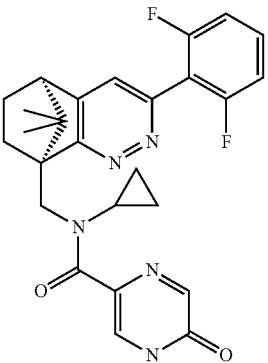 | N-cyclopropyl-N-(((5R,8S)-3-(2,6-difluorophenyl)-9,9-dimethyl-5,6,7,8-tetrahydro-5,8-methanocinnolin-8-yl)methyl)-5-oxo-4,5-dihydropyrazine-2-carboxamide | 0.158 |

TABLE 1-continued

| Structure | Name | IC$_{50}$ |
|---|---|---|
| 34 | N-(((5R,8S)-3-(2,6-difluorophenyl)-9,9-dimethyl-5,6,7,8-tetrahydro-5,8-methanocinnolin-8-yl)methyl)-N-(1-methylcyclopropyl)-5-oxo-4,5-dihydropyrazine-2-carboxamide | 0.136 |
| 35 | N-(((5R,8S)-3-(2,6-difluorophenyl)-9,9-dimethyl-5,6,7,8-tetrahydro-5,8-methanocinnolin-8-yl)methyl)-N-methyl-5-oxo-4,5-dihydropyrazine-2-carboxamide | 0.0337 |
| 36 | N-(((5R,8S)-3-(2,6-difluorophenyl)-9,9-dimethyl-5,6,7,8-tetrahydro-5,8-methanocinnolin-8-yl)methyl)-N-methyl-5-oxo-4,5-dihydropyrazine-2-carboxamide | 0.0396 |
| 37 | N-(((5R,8S)-3-(2,6-difluorophenyl)-9,9-dimethyl-5,6,7,8-tetrahydro-5,8-methanocinnolin-8-yl)methyl)-N-ethyl-2-(pyrazin-2-yl)acetamide | 0.024 |

TABLE 1-continued

| | Structure | Name | IC$_{50}$ |
|---|---|---|---|
| 38 | 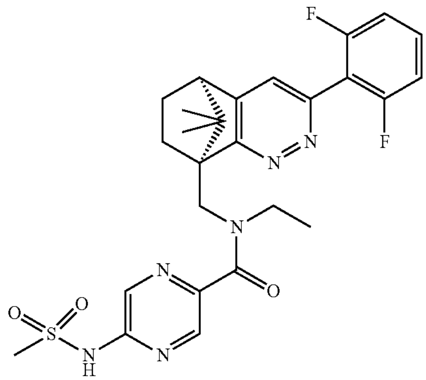 [SMILES: CCN(C[C@@]12CC[C@@H](c3cc(-c4c(F)cccc4F)nnc31)C2(C)C)C(=O)c1cnc(NS(C)(=O)=O)cn1] | N-(((5R,8S)-3-(2,6-difluorophenyl)-9,9-dimethyl-5,6,7,8-tetrahydro-5,8-methanocinnolin-8-yl)methyl)-N-ethyl-5-(methylsulfonamido)pyrazine-2-carboxamide | 0.101 |
| 39 | 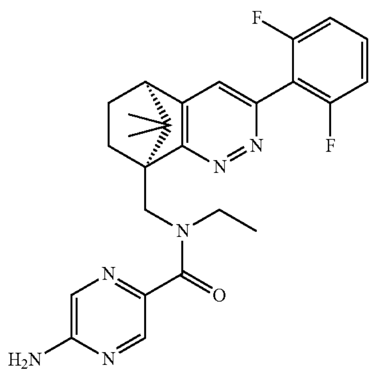 [SMILES: CCN(C[C@@]12CC[C@@H](c3cc(-c4c(F)cccc4F)nnc31)C2(C)C)C(=O)c1cnc(N)cn1] | 5-amino-N-(((5R,8S)-3-(2,6-difluorophenyl)-9,9-dimethyl-5,6,7,8-tetrahydro-5,8-methanocinnolin-8-yl)methyl)-N-ethylpyrazine-2-carboxamide | 0.0279 |
| 40 | 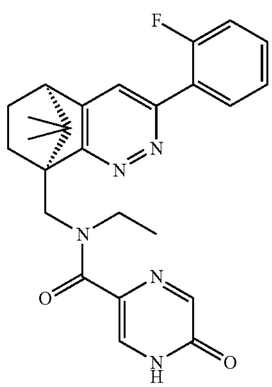 [SMILES: CCN(C[C@@]12CC[C@@H](c3cc(-c4ccccc4F)nnc31)C2(C)C)C(=O)c1c[nH]c(=O)cn1] | N-ethyl-N-(((5R,8S)-3-(2-fluorophenyl)-9,9-dimethyl-5,6,7,8-tetrahydro-5,8-methanocinnolin-8-yl)methyl)-5-oxo-4,5-dihydropyrazine-2-carboxamide | 0.030 |
| 41 | 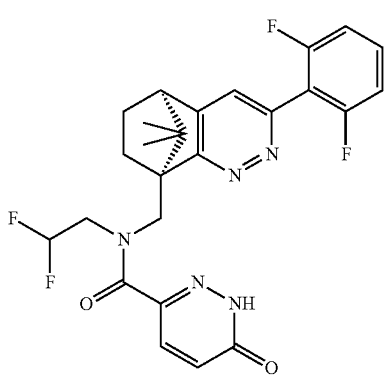 [SMILES: CC1(C)[C@H]2CC[C@]1(CN(CC(F)F)C(=O)c1ccc(=O)[nH]n1)c1nnc(-c3c(F)cccc3F)cc12] | N-(2,2-difluoroethyl)-N-(((5R,8S)-3-(2,6-difluorophenyl)-9,9-dimethyl-5,6,7,8-tetrahydro-5,8-methanocinnolin-8-yl)methyl)-6-oxo-1,6-dihydropyridazine-3-carboxamide | 0.0294 |

TABLE 1-continued

| | Structure | Name | IC$_{50}$ |
|---|---|---|---|
| 42 | 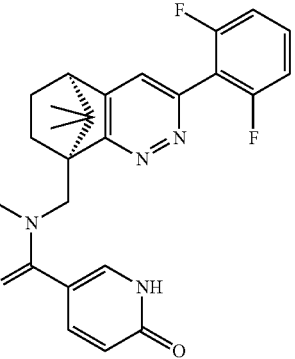 | N-(2,2-difluoroethyl)-N-(((5R,8S)-3-(2,6-difluorophenyl)-9,9-dimethyl-5,6,7,8-tetrahydro-5,8-methanocinnolin-8-yl)methyl)-6-oxo-1,6-dihydropyridine-3-carboxamide | 0.0755 |
| 43 | 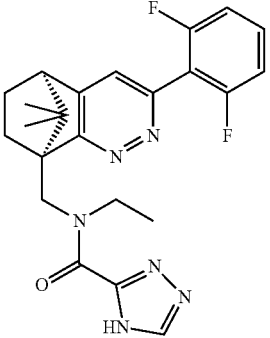 [SMILES: CCN(C[C@@]12CC[C@@H](c3cc(-c4c(F)cccc4F)nnc31)C2(C)C)C(=O)c1nnc[nH]1] | N-(((5R,8S)-3-(2,6-difluorophenyl)-9,9-dimethyl-5,6,7,8-tetrahydro-5,8-methanocinnolin-8-yl)methyl)-N-ethyl-4H-1,2,4-triazole-3-carboxamide | 0.0576 |
| 44 | 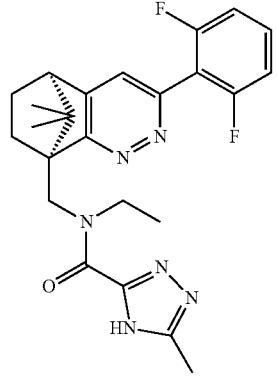 [SMILES: CCN(C[C@@]12CC[C@@H](c3cc(-c4c(F)cccc4F)nnc31)C2(C)C)C(=O)c1nnc(C)[nH]1] | N-(((5R,8S)-3-(2,6-difluorophenyl)-9,9-dimethyl-5,6,7,8-tetrahydro-5,8-methanocinnolin-8-yl)methyl)-N-ethyl-5-methyl-4H-1,2,4-triazole-3-carboxamide | 0.0697 |
| 45 | 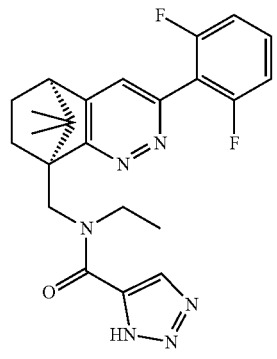 [SMILES: CCN(C[C@@]12CC[C@@H](c3cc(-c4c(F)cccc4F)nnc31)C2(C)C)C(=O)c1cnn[nH]1] | N-(((5R,8S)-3-(2,6-difluorophenyl)-9,9-dimethyl-5,6,7,8-tetrahydro-5,8-methanocinnolin-8-yl)methyl)-N-ethyl-1H-1,2,3-triazole-5-carboxamide | 0.0282 |

TABLE 1-continued

| | Structure | Name | IC$_{50}$ |
|---|---|---|---|
| 46 | 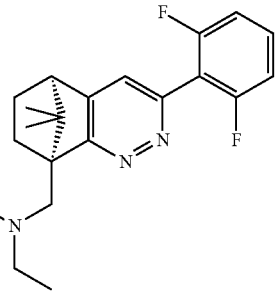 | N-(((5R,8S)-3-(2,6-difluorophenyl)-9,9-dimethyl-5,6,7,8-tetrahydro-5,8-methanocinnolin-8-yl)methyl)-N-ethyl-5-oxo-4,5-dihydro-1H-1,2,4-triazole-3-carboxamide | 0.0428 |
| 47 | 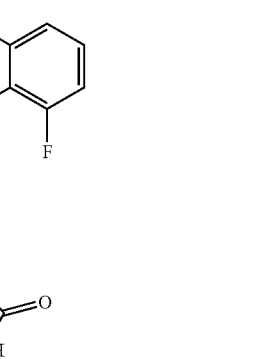 | N-(((5R,8S)-3-(2,6-difluorophenyl)-9,9-dimethyl-5,6,7,8-tetrahydro-5,8-methanocinnolin-8-yl)methyl)-N-ethyl-5-oxo-2,5-dihydro-1H-pyrazole-3-carboxamide | 0.137 |
| 48 | 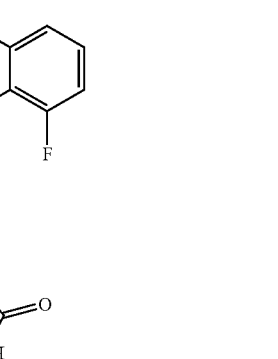 | N-(((5R,8S)-3-(2,6-difluorophenyl)-9,9-dimethyl-5,6,7,8-tetrahydro-5,8-methanocinnolin-8-yl)methyl)-N-ethyl-2-oxo-2,3-dihydro-1H-imidazole-4-carboxamide | 0.119 |
| 49 | 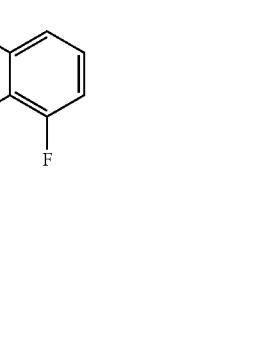 | N-(((5R,8S)-3-(2,6-difluorophenyl)-9,9-dimethyl-5,6,7,8-tetrahydro-5,8-methanocinnolin-8-yl)methyl)-N-ethyl-3-hydroxyoxetane-3-carboxamide | 0.030 |

TABLE 1-continued

| | Structure | Name | IC$_{50}$ |
|---|---|---|---|
| 50 | 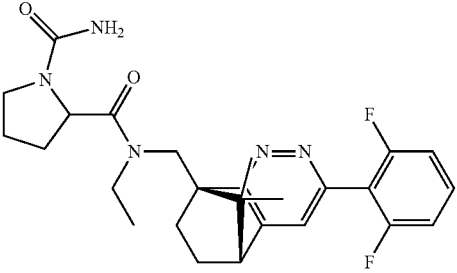 | N2-(((5R,8S)-3-(2,6-difluorophenyl)-9,9-dimethyl-5,6,7,8-tetrahydro-5,8-methanocinnolin-8-yl)methyl)-N2-ethylpyrrolidine-1,2-dicarboxamide | 0.115 |
| 51 | 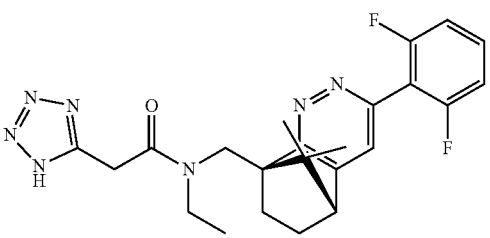 | N-(((5R,8S)-3-(2,6-difluorophenyl)-9,9-dimethyl-5,6,7,8-tetrahydro-5,8-methanocinnolin-8-yl)methyl)-N-ethyl-2-(1H-tetrazol-5-yl)acetamide | 0.0442 |
| 52 | 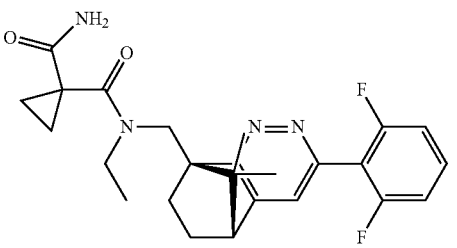 | N-(((5R,8S)-3-(2,6-difluorophenyl)-9,9-dimethyl-5,6,7,8-tetrahydro-5,8-methanocinnolin-8-yl)methyl)-N-ethylcyclopropane-1,1-dicarboxamide | 0.0826 |
| 53 | 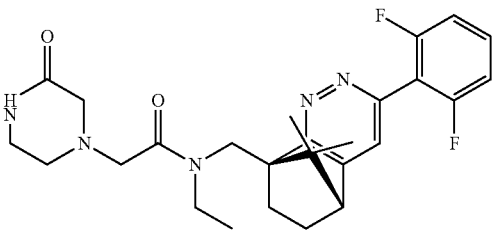 | N-(((5R,8S)-3-(2,6-difluorophenyl)-9,9-dimethyl-5,6,7,8-tetrahydro-5,8-methanocinnolin-8-yl)methyl)-N-ethyl-2-(3-oxopiperazin-1-yl)acetamide | 0.0764 |
| 54 | 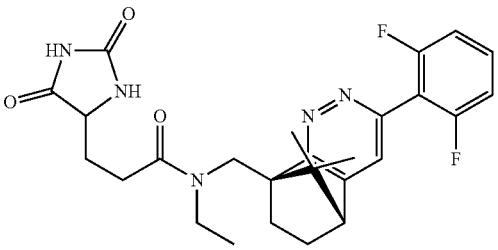 | N-(((5R,8S)-3-(2,6-difluorophenyl)-9,9-dimethyl-5,6,7,8-tetrahydro-5,8-methanocinnolin-8-yl)methyl)-3-(2,5-dioxoimidazolidin-4-yl)-N-ethylpropanamide | 0.0377 |
| 55 | 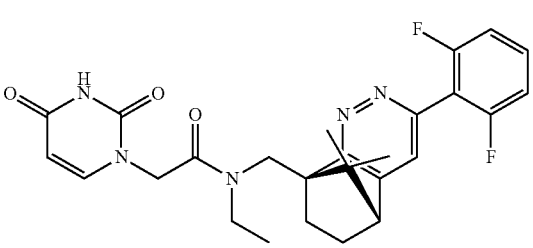 | N-(((5R,8S)-3-(2,6-difluorophenyl)-9,9-dimethyl-5,6,7,8-tetrahydro-5,8-methanocinnolin-8-yl)methyl)-2-(2,4-dioxo-3,4-dihydropyrimidin-1(2H)-yl)-N-ethylacetamide | 0.0742 |

TABLE 1-continued

| | Structure | Name | IC$_{50}$ |
|---|---|---|---|
| 56 | 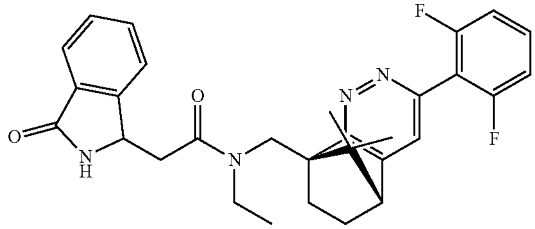 | N-(((5R,8S)-3-(2,6-difluorophenyl)-9,9-dimethyl-5,6,7,8-tetrahydro-5,8-methanocinnolin-8-yl)methyl)-N-ethyl-2-(3-oxoisoindolin-1-yl)acetamide | 0.0355 |
| 57 | 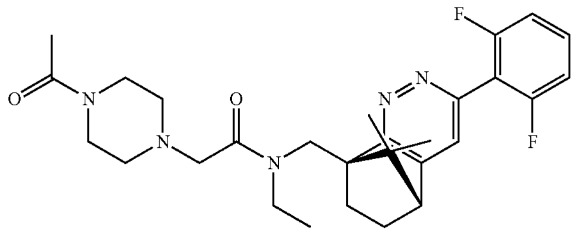 | 2-(4-acetylpiperazin-1-yl)-N-(((5R,8S)-3-(2,6-difluorophenyl)-9,9-dimethyl-5,6,7,8-tetrahydro-5,8-methanocinnolin-8-yl)methyl)-N-ethylacetamide | 0.0966 |
| 58 | 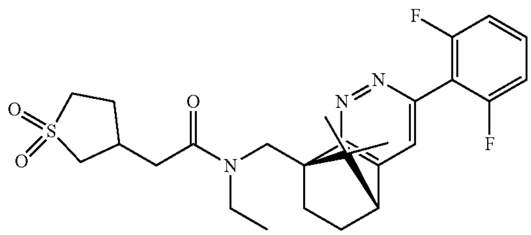 | N-(((5R,8S)-3-(2,6-difluorophenyl)-9,9-dimethyl-5,6,7,8-tetrahydro-5,8-methanocinnolin-8-yl)methyl)-2-(1,1-dioxidotetrahydrothiophen-3-yl)-N-ethylacetamide | 0.0386 |
| 59 | 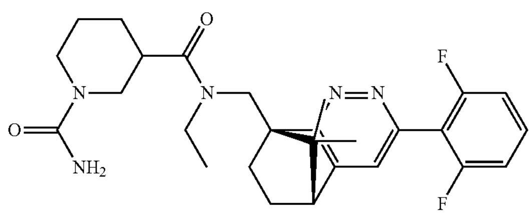 | N3-(((5R,8S)-3-(2,6-difluorophenyl)-9,9-dimethyl-5,6,7,8-tetrahydro-5,8-methanocinnolin-8-yl)methyl)-N3-ethylpiperidine-1,3-dicarboxamide | 0.0812 |
| 60 | 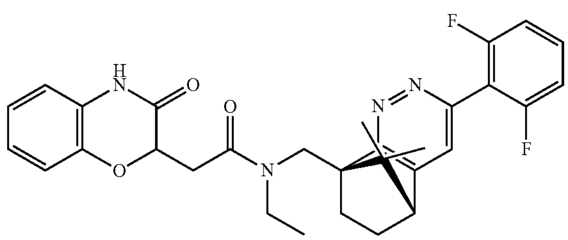 | N-(((5R,8S)-3-(2,6-difluorophenyl)-9,9-dimethyl-5,6,7,8-tetrahydro-5,8-methanocinnolin-8-yl)methyl)-N-ethyl-2-(3-oxo-3,4-dihydro-2H-benzo[b][1,4]oxazin-2-yl)acetamide | 0.0132 |
| 61 | 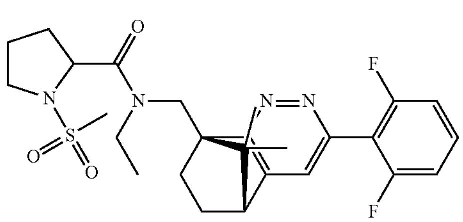 | N-(((5R,8S)-3-(2,6-difluorophenyl)-9,9-dimethyl-5,6,7,8-tetrahydro-5,8-methanocinnolin-8-yl)methyl)-N-ethyl-1-(methylsulfonyl)pyrrolidine-2-carboxamide | 0.0608 |
| 62 | 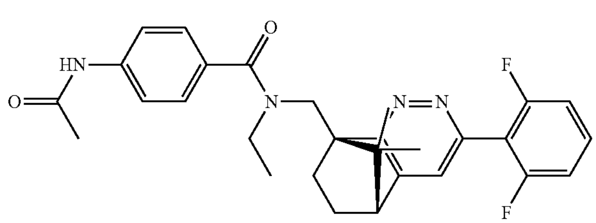 | 4-acetamido-N-(((5R,8S)-3-(2,6-difluorophenyl)-9,9-dimethyl-5,6,7,8-tetrahydro-5,8-methanocinnolin-8-yl)methyl)-N-ethylbenzamide | 0.0213 |

TABLE 1-continued

| | Structure | Name | IC$_{50}$ |
|---|---|---|---|
| 63 | 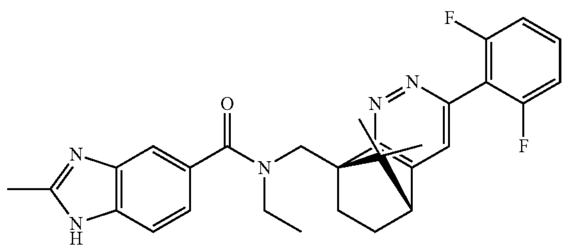 | N-(((5R,8S)-3-(2,6-difluorophenyl)-9,9-dimethyl-5,6,7,8-tetrahydro-5,8-methanocinnolin-8-yl)methyl)-N-ethyl-2-methyl-1H-benzo[d]imidazole-5-carboxamide | 0.037 |
| 64 | 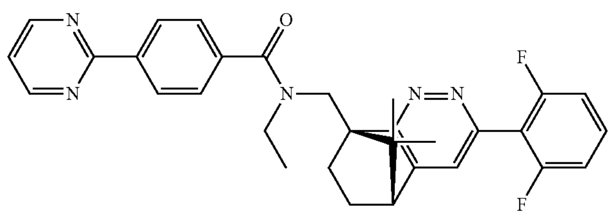 | N-(((5R,8S)-3-(2,6-difluorophenyl)-9,9-dimethyl-5,6,7,8-tetrahydro-5,8-methanocinnolin-8-yl)methyl)-N-ethyl-4-(pyrimidin-2-yl)benzamide | 0.0121 |
| 65 | 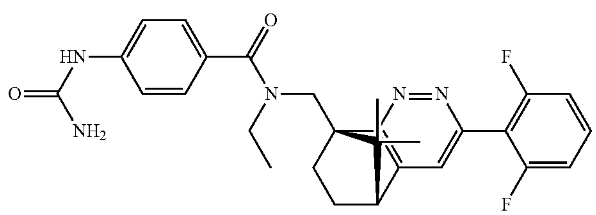 | N-(((5R,8S)-3-(2,6-difluorophenyl)-9,9-dimethyl-5,6,7,8-tetrahydro-5,8-methanocinnolin-8-yl)methyl)-N-ethyl-4-ureidobenzamide | 0.0257 |
| 66 | 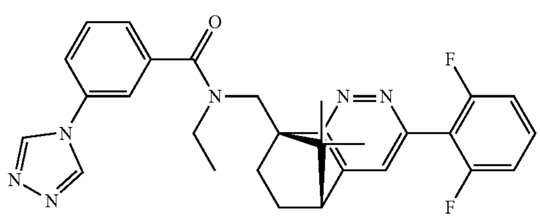 | N-(((5R,8S)-3-(2,6-difluorophenyl)-9,9-dimethyl-5,6,7,8-tetrahydro-5,8-methanocinnolin-8-yl)methyl)-N-ethyl-3-(4H-1,2,4-triazol-4-yl)benzamide | 0.0406 |
| 67 | 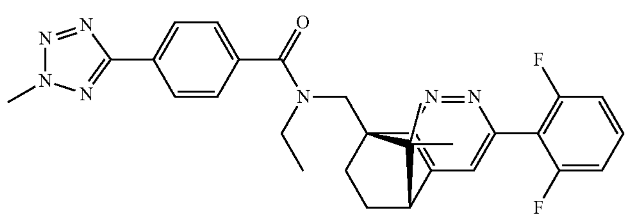 | N-(((5R,8S)-3-(2,6-difluorophenyl)-9,9-dimethyl-5,6,7,8-tetrahydro-5,8-methanocinnolin-8-yl)methyl)-N-ethyl-4-(2-methyl-2H-tetrazol-5-yl)benzamide | 0.0134 |
| 68 | 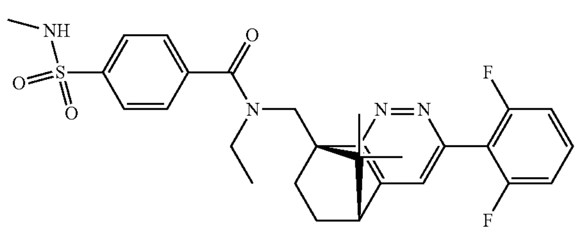 | N-(((5R,8S)-3-(2,6-difluorophenyl)-9,9-dimethyl-5,6,7,8-tetrahydro-5,8-methanocinnolin-8-yl)methyl)-N-ethyl-4-(N-methylsulfamoyl)benzamide | 0.0155 |
| 69 | 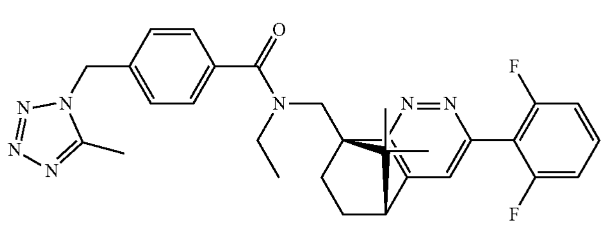 | N-(((5R,8S)-3-(2,6-difluorophenyl)-9,9-dimethyl-5,6,7,8-tetrahydro-5,8-methanocinnolin-8-yl)methyl)-N-ethyl-4-((5-methyl-1H-tetrazol-1-yl)methyl)benzamide | 0.0243 |

TABLE 1-continued

| | Structure | Name | IC$_{50}$ |
|---|---|---|---|
| 70 | 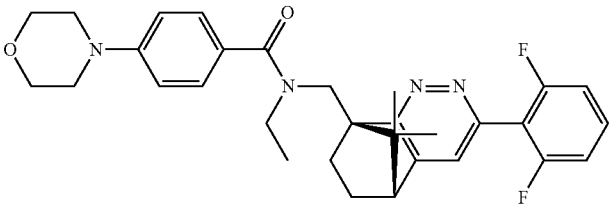 | N-(((5R,8S)-3-(2,6-difluorophenyl)-9,9-dimethyl-5,6,7,8-tetrahydro-5,8-methanocinnolin-8-yl)methyl)-N-ethyl-4-morpholinobenzamide | 0.0331 |
| 71 | 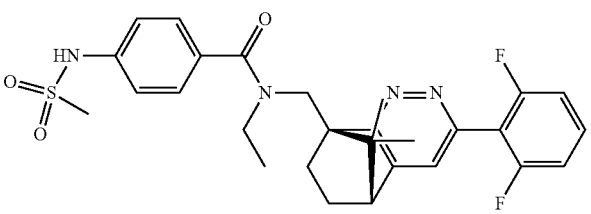 | N-(((5R,8S)-3-(2,6-difluorophenyl)-9,9-dimethyl-5,6,7,8-tetrahydro-5,8-methanocinnolin-8-yl)methyl)-N-ethyl-4-(methylsulfonamido)benzamide | 0.0261 |
| 72 | 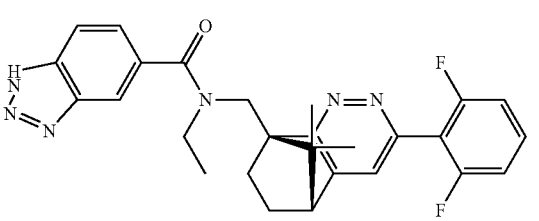 | N-(((5R,8S)-3-(2,6-difluorophenyl)-9,9-dimethyl-5,6,7,8-tetrahydro-5,8-methanocinnolin-8-yl)methyl)-N-ethyl-1H-benzo[d][1,2,3]triazole-5-carboxamide | 0.0184 |
| 73 | 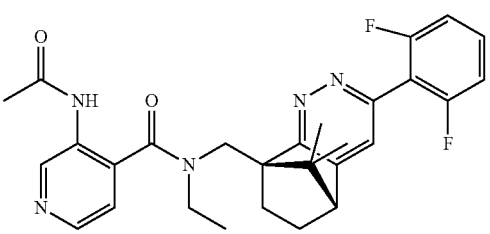 | 3-acetamido-N-(((5R,8S)-3-(2,6-difluorophenyl)-9,9-dimethyl-5,6,7,8-tetrahydro-5,8-methanocinnolin-8-yl)methyl)-N-ethylisonicotinamide | 0.124 |
| 74 | 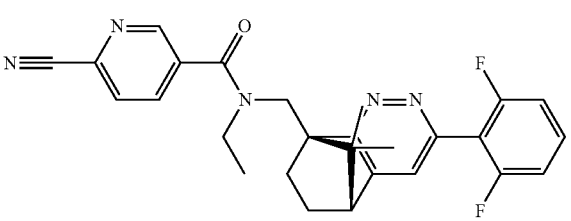 | 6-cyano-N-(((5R,8S)-3-(2,6-difluorophenyl)-9,9-dimethyl-5,6,7,8-tetrahydro-5,8-methanocinnolin-8-yl)methyl)-N-ethylnicotinamide | 0.0225 |
| 75 | 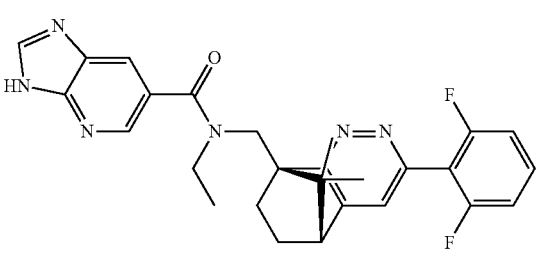 | N-(((5R,8S)-3-(2,6-difluorophenyl)-9,9-dimethyl-5,6,7,8-tetrahydro-5,8-methanocinnolin-8-yl)methyl)-N-ethyl-3H-imidazo[4,5-b]pyridine-6-carboxamide | 0.0623 |
| 76 | 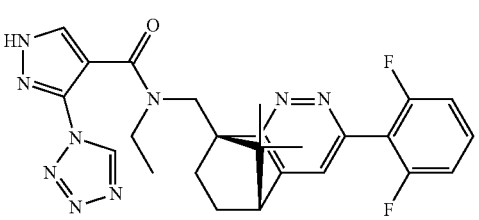 | N-(((5R,8S)-3-(2,6-difluorophenyl)-9,9-dimethyl-5,6,7,8-tetrahydro-5,8-methanocinnolin-8-yl)methyl)-N-ethyl-3-(1H-tetrazol-1-yl)-1H-pyrazole-4-carboxamide | 0.043 |

TABLE 1-continued

| | Structure | Name | IC$_{50}$ |
|---|---|---|---|
| 77 | 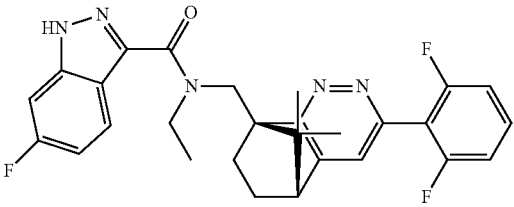 | N-(((5R,8S)-3-(2,6-difluorophenyl)-9,9-dimethyl-5,6,7,8-tetrahydro-5,8-methanocinnolin-8-yl)methyl)-N-ethyl-6-fluoro-1H-indazole-3-carboxamide | 0.0092 |
| 78 | 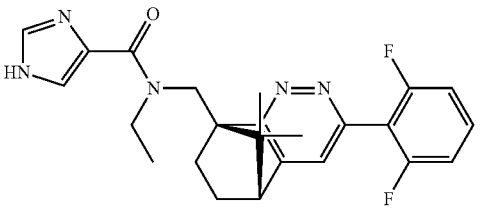 | N-(((5R,8S)-3-(2,6-difluorophenyl)-9,9-dimethyl-5,6,7,8-tetrahydro-5,8-methanocinnolin-8-yl)methyl)-N-ethyl-1H-imidazole-4-carboxamide | 0.0314 |
| 79 | 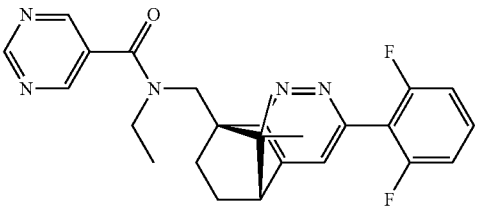 | N-(((5R,8S)-3-(2,6-difluorophenyl)-9,9-dimethyl-5,6,7,8-tetrahydro-5,8-methanocinnolin-8-yl)methyl)-N-ethylpyrimidine-5-carboxamide | 0.0433 |
| 80 | 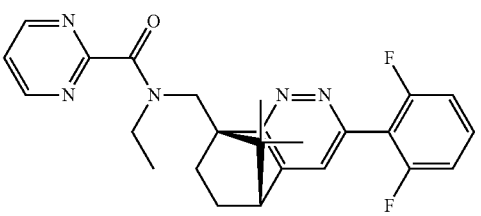 | N-(((5R,8S)-3-(2,6-difluorophenyl)-9,9-dimethyl-5,6,7,8-tetrahydro-5,8-methanocinnolin-8-yl)methyl)-N-ethylpyrimidine-2-carboxamide | 0.0399 |
| 81 | 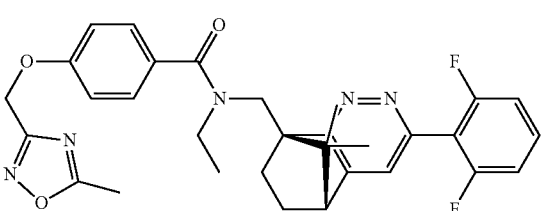 | N-(((5R,8S)-3-(2,6-difluorophenyl)-9,9-dimethyl-5,6,7,8-tetrahydro-5,8-methanocinnolin-8-yl)methyl)-N-ethyl-4-((5-methyl-1,2,4-oxadiazol-3-yl)methoxy)benzamide | 0.0147 |
| 82 | 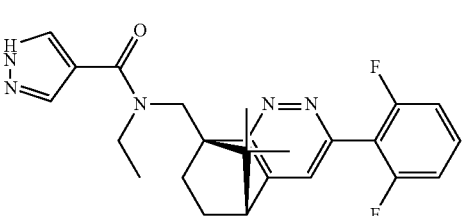 | N-(((5R,8S)-3-(2,6-difluorophenyl)-9,9-dimethyl-5,6,7,8-tetrahydro-5,8-methanocinnolin-8-yl)methyl)-N-ethyl-1H-pyrazole-4-carboxamide | 0.0224 |
| 83 | 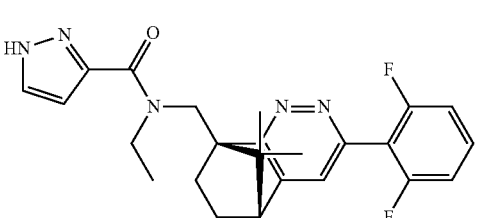 | N-(((5R,8S)-3-(2,6-difluorophenyl)-9,9-dimethyl-5,6,7,8-tetrahydro-5,8-methanocinnolin-8-yl)methyl)-N-ethyl-1H-pyrazole-3-carboxamide | 0.0213 |

TABLE 1-continued

| | Structure | Name | IC$_{50}$ |
|---|---|---|---|
| 84 | 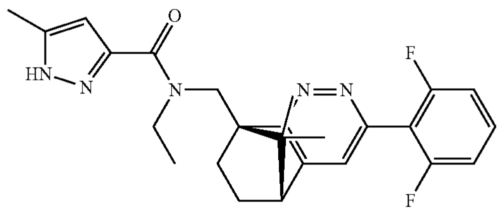 | N-(((5R,8S)-3-(2,6-difluorophenyl)-9,9-dimethyl-5,6,7,8-tetrahydro-5,8-methanocinnolin-8-yl)methyl)-N-ethyl-5-methyl-1H-pyrazole-3-carboxamide | 0.0428 |
| 85 | 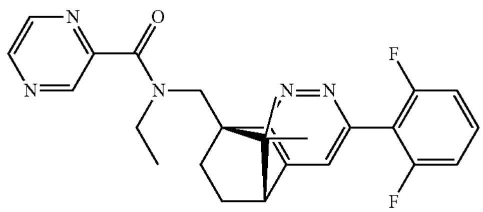 | N-(((5R,8S)-3-(2,6-difluorophenyl)-9,9-dimethyl-5,6,7,8-tetrahydro-5,8-methanocinnolin-8-yl)methyl)-N-ethylpyrazine-2-carboxamide | 0.0415 |
| 86 | 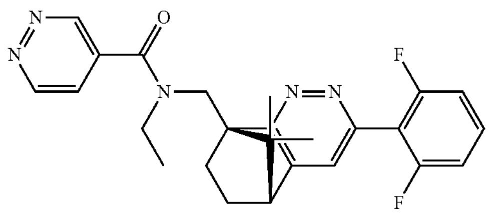 | N-(((5R,8S)-3-(2,6-difluorophenyl)-9,9-dimethyl-5,6,7,8-tetrahydro-5,8-methanocinnolin-8-yl)methyl)-N-ethylpyridazine-4-carboxamide | 0.0114 |
| 87 | 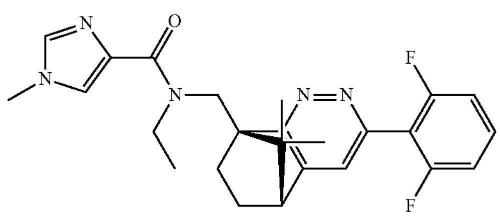 | N-(((5R,8S)-3-(2,6-difluorophenyl)-9,9-dimethyl-5,6,7,8-tetrahydro-5,8-methanocinnolin-8-yl)methyl)-N-ethyl-1-methyl-1H-imidazole-4-carboxamide | 0.0277 |
| 88 | 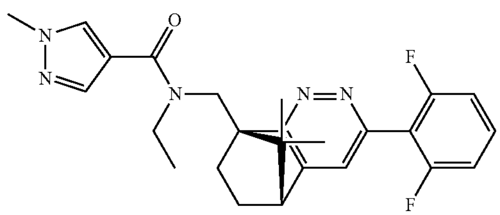 | N-(((5R,8S)-3-(2,6-difluorophenyl)-9,9-dimethyl-5,6,7,8-tetrahydro-5,8-methanocinnolin-8-yl)methyl)-N-ethyl-1-methyl-1H-pyrazole-4-carboxamide | 0.0235 |
| 89 | 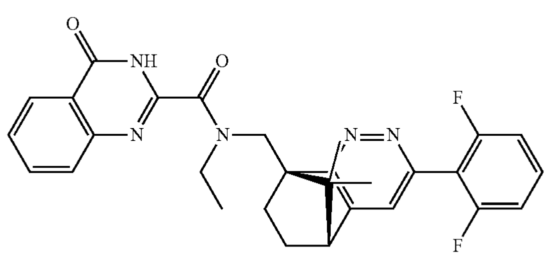 | N-(((5R,8S)-3-(2,6-difluorophenyl)-9,9-dimethyl-5,6,7,8-tetrahydro-5,8-methanocinnolin-8-yl)methyl)-N-ethyl-4-oxo-3,4-dihydroquinazoline-2-carboxamide | 0.105 |
| 90 | 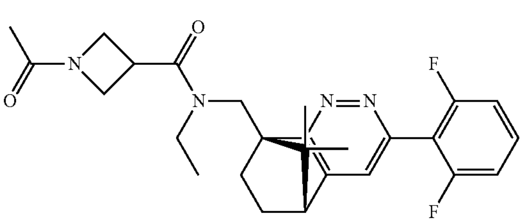 | 1-acetyl-N-(((5R,8S)-3-(2,6-difluorophenyl)-9,9-dimethyl-5,6,7,8-tetrahydro-5,8-methanocinnolin-8-yl)methyl)-N-ethylazetidine-3-carboxamide | 0.0826 |

TABLE 1-continued

| | Structure | Name | IC$_{50}$ |
|---|---|---|---|
| 91 | 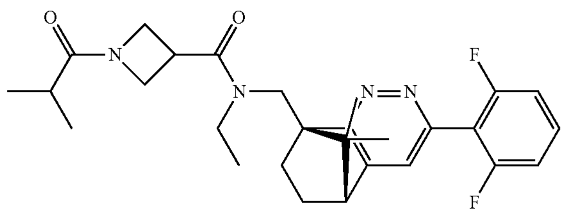 | N-(((5R,8S)-3-(2,6-difluorophenyl)-9,9-dimethyl-5,6,7,8-tetrahydro-5,8-methanocinnolin-8-yl)methyl)-N-ethyl-1-isobutyrylazetidine-3-carboxamide | 0.0687 |
| 92 | 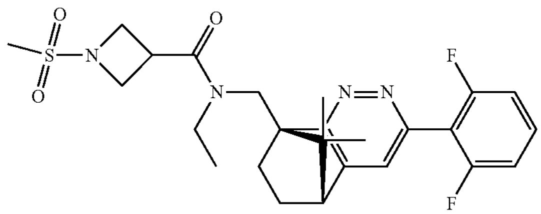 | N-(((5R,8S)-3-(2,6-difluorophenyl)-9,9-dimethyl-5,6,7,8-tetrahydro-5,8-methanocinnolin-8-yl)methyl)-N-ethyl-1-(methylsulfonyl)azetidine-3-carboxamide | 0.0281 |
| 93 | 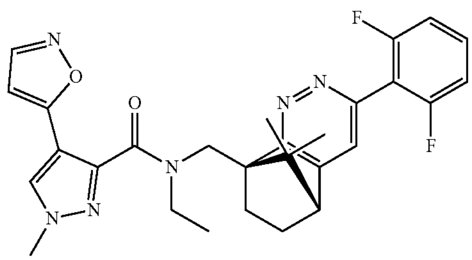 | N-(((5R,8S)-3-(2,6-difluorophenyl)-9,9-dimethyl-5,6,7,8-tetrahydro-5,8-methanocinnolin-8-yl)methyl)-N-ethyl-4-(isoxazol-5-yl)-1-methyl-1H-pyrazole-3-carboxamide | 0.0729 |
| 94 | 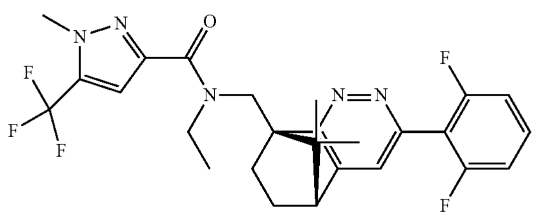 | N-(((5R,8S)-3-(2,6-difluorophenyl)-9,9-dimethyl-5,6,7,8-tetrahydro-5,8-methanocinnolin-8-yl)methyl)-N-ethyl-1-methyl-5-(trifluoromethyl)-1H-pyrazole-3-carboxamide | 0.0055 |
| 95 | 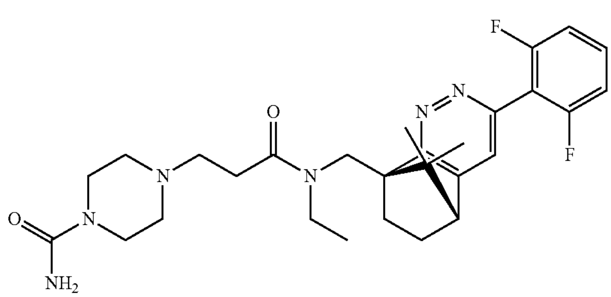 | 4-(3-((((5R,8S)-3-(2,6-difluorophenyl)-9,9-dimethyl-5,6,7,8-tetrahydro-5,8-methanocinnolin-8-yl)methyl)(ethyl)amino)-3-oxopropyl)piperazine-1-carboxamide | 0.152 |
| 96 | 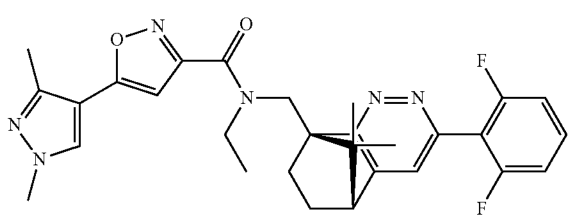 | N-(((5R,8S)-3-(2,6-difluorophenyl)-9,9-dimethyl-5,6,7,8-tetrahydro-5,8-methanocinnolin-8-yl)methyl)-5-(1,3-dimethyl-1H-pyrazol-4-yl)-N-ethylisoxazole-3-carboxamide | 0.0104 |

TABLE 1-continued

| | Structure | Name | IC$_{50}$ |
|---|---|---|---|
| 97 | 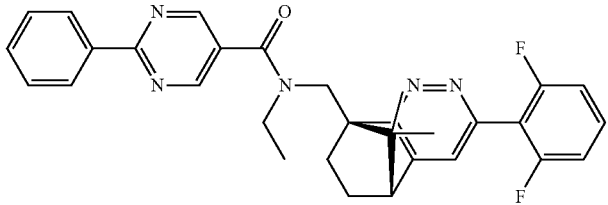 | N-(((5R,8S)-3-(2,6-difluorophenyl)-9,9-dimethyl-5,6,7,8-tetrahydro-5,8-methanocinnolin-8-yl)methyl)-N-ethyl-2-phenylpyrimidine-5-carboxamide | 0.0331 |
| 98 | 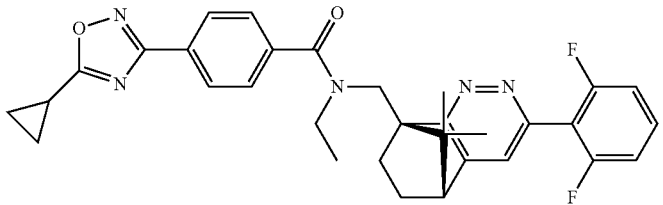 | 4-(5-cyclopropyl-1,2,4-oxadiazol-3-yl)-N-(((5R,8S)-3-(2,6-difluorophenyl)-9,9-dimethyl-5,6,7,8-tetrahydro-5,8-methanocinnolin-8-yl)methyl)-N-ethylbenzamide | 0.0069 |
| 99 | 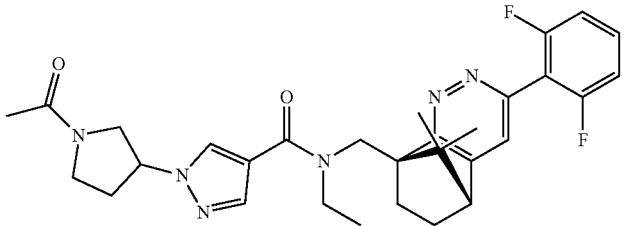 | 1-(1-acetylpyrrolidin-3-yl)-N-(((5R,8S)-3-(2,6-difluorophenyl)-9,9-dimethyl-5,6,7,8-tetrahydro-5,8-methanocinnolin-8-yl)methyl)-N-ethyl-1H-pyrazole-4-carboxamide | 0.0816 |
| 100 | 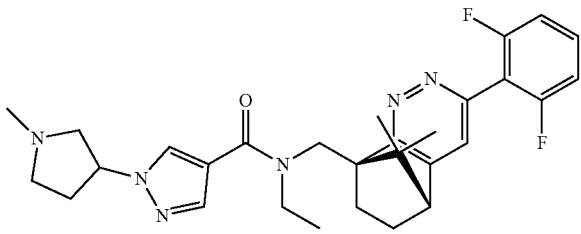 | N-(((5R,8S)-3-(2,6-difluorophenyl)-9,9-dimethyl-5,6,7,8-tetrahydro-5,8-methanocinnolin-8-yl)methyl)-N-ethyl-1-(1-methylpyrrolidin-3-yl)-1H-pyrazole-4-carboxamide | 0.0787 |
| 101 | 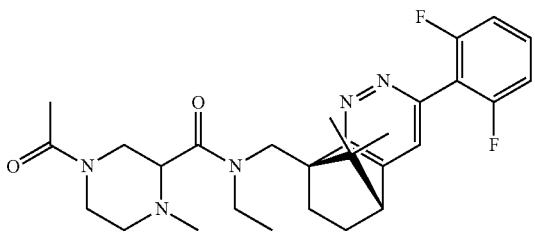 | 4-acetyl-N-(((5R,8S)-3-(2,6-difluorophenyl)-9,9-dimethyl-5,6,7,8-tetrahydro-5,8-methanocinnolin-8-yl)methyl)-N-ethyl-1-methylpiperazine-2-carboxamide | 1.15 |
| 102 | 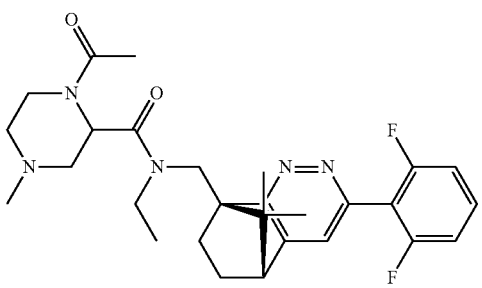 | 1-acetyl-N-(((5R,8S)-3-(2,6-difluorophenyl)-9,9-dimethyl-5,6,7,8-tetrahydro-5,8-methanocinnolin-8-yl)methyl)-N-ethyl-4-methylpiperazine-2-carboxamide | 0.71 |

TABLE 1-continued

| | Structure | Name | IC$_{50}$ |
|---|---|---|---|
| 103 | 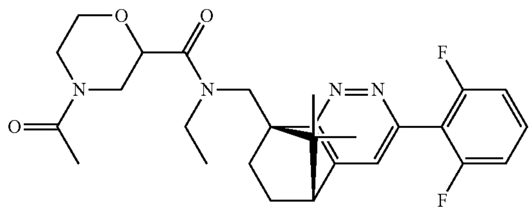 | 4-acetyl-N-(((5R,8S)-3-(2,6-difluorophenyl)-9,9-dimethyl-5,6,7,8-tetrahydro-5,8-methanocinnolin-8-yl)methyl)-N-ethylmorpholine-2-carboxamide | 0.149 |
| 104 | 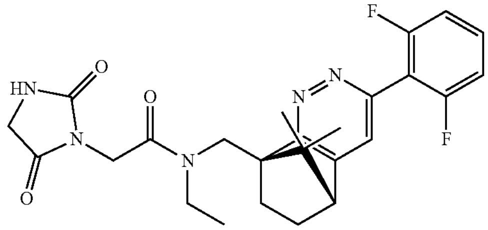 | N-(((5R,8S)-3-(2,6-difluorophenyl)-9,9-dimethyl-5,6,7,8-tetrahydro-5,8-methanocinnolin-8-yl)methyl)-2-(2,5-dioxoimidazolidin-1-yl)-N-ethylacetamide | 0.080 |
| 105 | 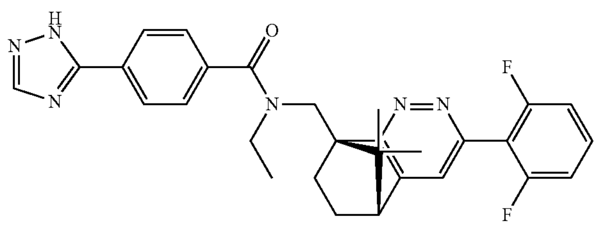 | N-(((5R,8S)-3-(2,6-difluorophenyl)-9,9-dimethyl-5,6,7,8-tetrahydro-5,8-methanocinnolin-8-yl)methyl)-N-ethyl-4-(1H-1,2,4-triazol-5-yl)benzamide | 0.0555 |
| 106 | 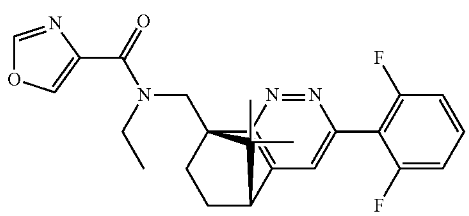 | N-(((5R,8S)-3-(2,6-difluorophenyl)-9,9-dimethyl-5,6,7,8-tetrahydro-5,8-methanocinnolin-8-yl)methyl)-N-ethyloxazole-4-carboxamide | 0.0055 |
| 107 | 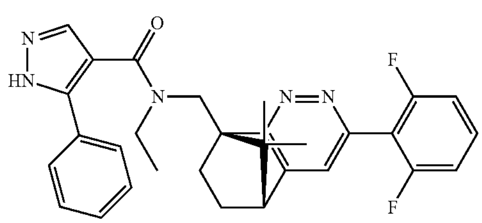 | N-(((5R,8S)-3-(2,6-difluorophenyl)-9,9-dimethyl-5,6,7,8-tetrahydro-5,8-methanocinnolin-8-yl)methyl)-N-ethyl-5-phenyl-1H-pyrazole-4-carboxamide | 0.114 |
| 108 | 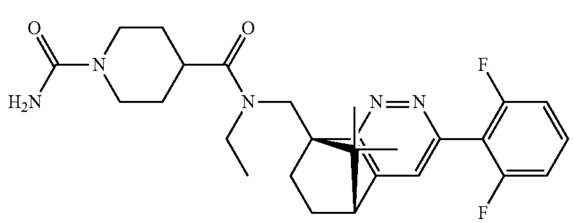 | N4-(((5R,8S)-3-(2,6-difluorophenyl)-9,9-dimethyl-5,6,7,8-tetrahydro-5,8-methanocinnolin-8-yl)methyl)-N4-ethylpiperidine-1,4-dicarboxamide | 0.163 |
| 109 | 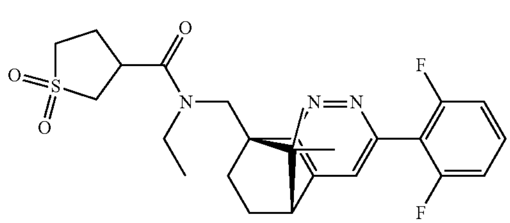 | N-(((5R,8S)-3-(2,6-difluorophenyl)-9,9-dimethyl-5,6,7,8-tetrahydro-5,8-methanocinnolin-8-yl)methyl)-N-ethyltetrahydrothiophene-3-carboxamide 1,1-dioxide | 0.070 |

TABLE 1-continued

| | Structure | Name | IC$_{50}$ |
|---|---|---|---|
| 110 | 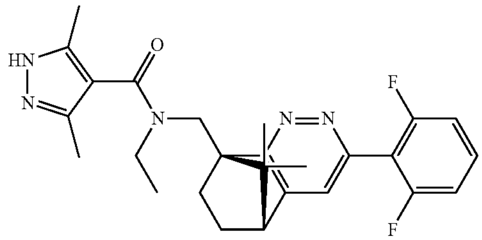 | N-(((5R,8S)-3-(2,6-difluorophenyl)-9,9-dimethyl-5,6,7,8-tetrahydro-5,8-methanocinnolin-8-yl)methyl)-N-ethyl-3,5-dimethyl-1H-pyrazole-4-carboxamide | 0.157 |
| 111 | 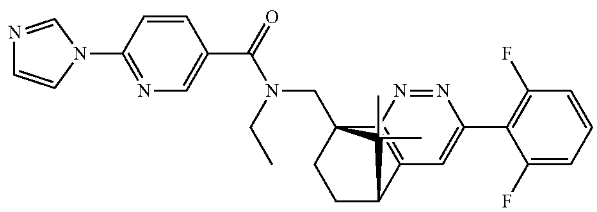 | N-(((5R,8S)-3-(2,6-difluorophenyl)-9,9-dimethyl-5,6,7,8-tetrahydro-5,8-methanocinnolin-8-yl)methyl)-N-ethyl-6-(1H-imidazol-1-yl)nicotinamide | 0.0478 |
| 112 | 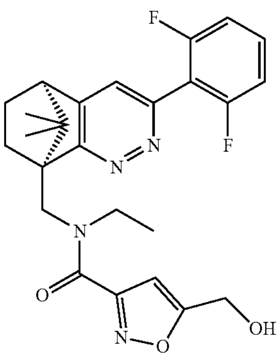 [SMILES: CCN(C[C@@]12CC[C@@H](c3cc(-c4c(F)cccc4F)nnc31)C2(C)C)C(=O)c1cc(CO)on1] | N-(((5R,8S)-3-(2,6-difluorophenyl)-9,9-dimethyl-5,6,7,8-tetrahydro-5,8-methanocinnolin-8-yl)methyl)-N-ethyl-5-(hydroxymethyl)isoxazole-3-carboxamide | 0.0069 |
| 113 | 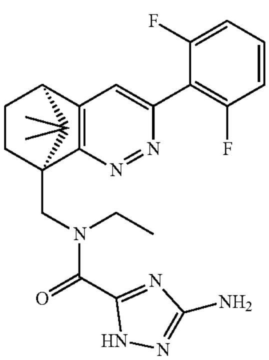 [SMILES: CCN(C[C@@]12CC[C@@H](c3cc(-c4c(F)cccc4F)nnc31)C2(C)C)C(=O)c1nc(N)n[nH]1] | 3-amino-N-(((5R,8S)-3-(2,6-difluorophenyl)-9,9-dimethyl-5,6,7,8-tetrahydro-5,8-methanocinnolin-8-yl)methyl)-N-ethyl-1H-1,2,4-triazole-5-carboxamide | 0.0564 |
| 114 | 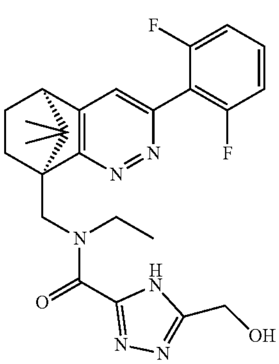 [SMILES: CCN(C[C@@]12CC[C@@H](c3cc(-c4c(F)cccc4F)nnc31)C2(C)C)C(=O)c1nnc(CO)[nH]1] | N-(((5R,8S)-3-(2,6-difluorophenyl)-9,9-dimethyl-5,6,7,8-tetrahydro-5,8-methanocinnolin-8-yl)methyl)-N-ethyl-5-(hydroxymethyl)-4H-1,2,4-triazole-3-carboxamide | 0.0582 |

TABLE 1-continued

| | Structure | Name | IC$_{50}$ |
|---|---|---|---|
| 115 | 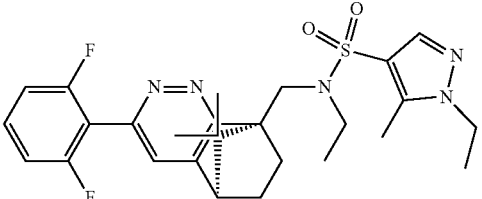 | N-(((5R,8S)-3-(2,6-difluorophenyl)-9,9-dimethyl-5,6,7,8-tetrahydro-5,8-methanocinnolin-8-yl)methyl)-N,1-diethyl-5-methyl-1H-pyrazole-4-sulfonamide | 0.0068 |
| 116 | 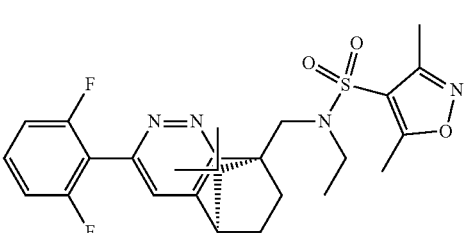 | N-(((5R,8S)-3-(2,6-difluorophenyl)-9,9-dimethyl-5,6,7,8-tetrahydro-5,8-methanocinnolin-8-yl)methyl)-N-ethyl-3,5-dimethylisoxazole-4-sulfonamide | 0.0092 |
| 117 | 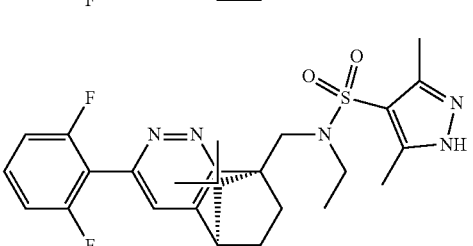 | N-(((5R,8S)-3-(2,6-difluorophenyl)-9,9-dimethyl-5,6,7,8-tetrahydro-5,8-methanocinnolin-8-yl)methyl)-N-ethyl-3,5-dimethyl-1H-pyrazole-4-sulfonamide | 0.0147 |
| 118 | 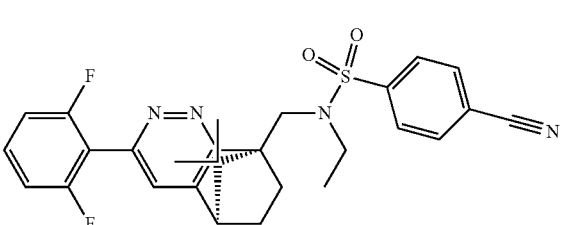 | 4-cyano-N-(((5R,8S)-3-(2,6-difluorophenyl)-9,9-dimethyl-5,6,7,8-tetrahydro-5,8-methanocinnolin-8-yl)methyl)-N-ethylbenzenesulfonamide | 0.0106 |
| 119 | 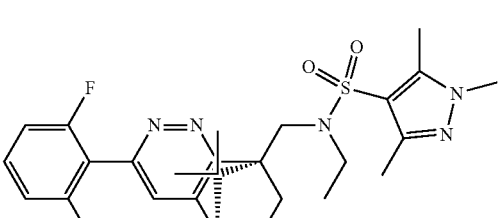 | N-(((5R,8S)-3-(2,6-difluorophenyl)-9,9-dimethyl-5,6,7,8-tetrahydro-5,8-methanocinnolin-8-yl)methyl)-N-ethyl-1,3,5-trimethyl-1H-pyrazole-4-sulfonamide | 0.0162 |
| 120 | 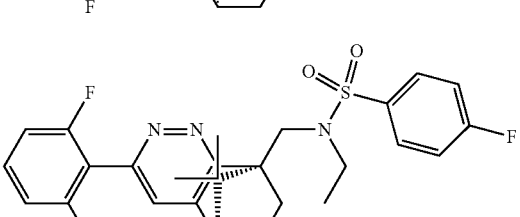 | N-(((5R,8S)-3-(2,6-difluorophenyl)-9,9-dimethyl-5,6,7,8-tetrahydro-5,8-methanocinnolin-8-yl)methyl)-N-ethyl-4-fluorobenzenesulfonamide | 0.0165 |
| 121 | 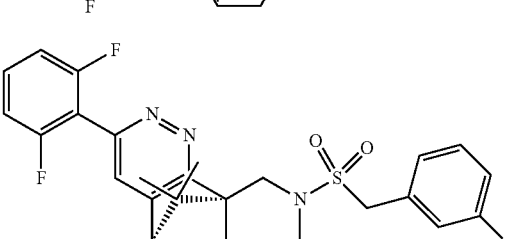 | N-(((5R,8S)-3-(2,6-difluorophenyl)-9,9-dimethyl-5,6,7,8-tetrahydro-5,8-methanocinnolin-8-yl)methyl)-N-ethyl-1-(3-fluorophenyl)methanesulfonamide | 0.0048 |

TABLE 1-continued

| | Structure | Name | IC$_{50}$ |
|---|---|---|---|
| 122 | 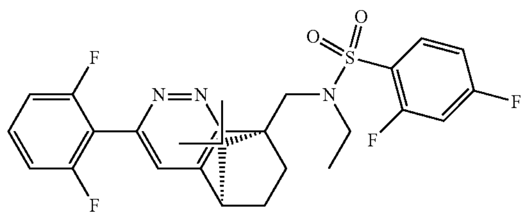 | N-(((5R,8S)-3-(2,6-difluorophenyl)-9,9-dimethyl-5,6,7,8-tetrahydro-5,8-methanocinnolin-8-yl)methyl)-N-ethyl-2,4-difluorobenzenesulfonamide | 0.0091 |
| 123 | 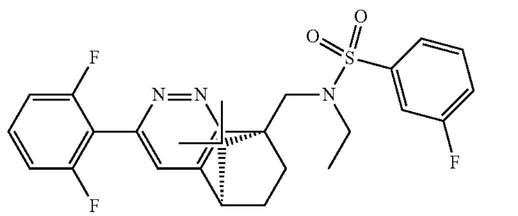 | N-(((5R,8S)-3-(2,6-difluorophenyl)-9,9-dimethyl-5,6,7,8-tetrahydro-5,8-methanocinnolin-8-yl)methyl)-N-ethyl-3-fluorobenzenesulfonamide | 0.0156 |
| 124 | 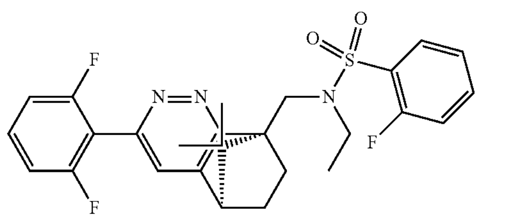 | N-(((5R,8S)-3-(2,6-difluorophenyl)-9,9-dimethyl-5,6,7,8-tetrahydro-5,8-methanocinnolin-8-yl)methyl)-N-ethyl-2-fluorobenzenesulfonamide | 0.0042 |
| 125 | 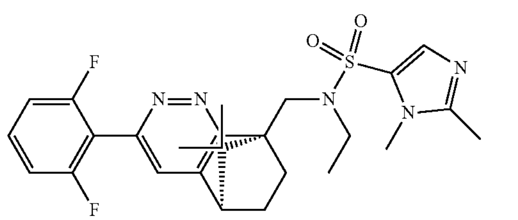 | N-(((5R,8S)-3-(2,6-difluorophenyl)-9,9-dimethyl-5,6,7,8-tetrahydro-5,8-methanocinnolin-8-yl)methyl)-N-ethyl-1,2-dimethyl-1H-imidazole-5-sulfonamide | 0.091 |
| 126 | 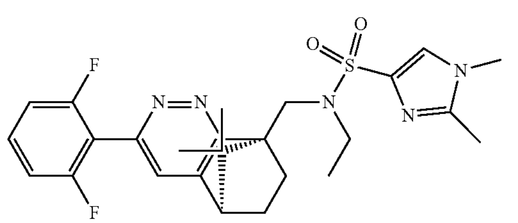 | N-(((5R,8S)-3-(2,6-difluorophenyl)-9,9-dimethyl-5,6,7,8-tetrahydro-5,8-methanocinnolin-8-yl)methyl)-N-ethyl-1,2-dimethyl-1H-imidazole-4-sulfonamide | 0.224 |
| 127 | 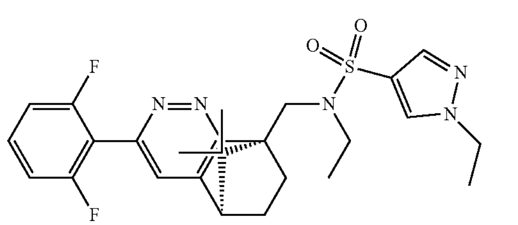 | N-(((5R,8S)-3-(2,6-difluorophenyl)-9,9-dimethyl-5,6,7,8-tetrahydro-5,8-methanocinnolin-8-yl)methyl)-N,1-diethyl-1H-pyrazole-4-sulfonamide | 0.0121 |
| 128 | 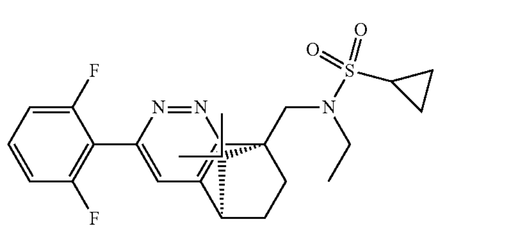 | N-(((5R,8S)-3-(2,6-difluorophenyl)-9,9-dimethyl-5,6,7,8-tetrahydro-5,8-methanocinnolin-8-yl)methyl)-N-ethylcyclopropanesulfonamide | 0.0073 |

TABLE 1-continued

| | Structure | Name | IC$_{50}$ |
|---|---|---|---|
| 129 | 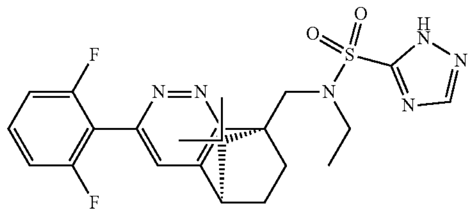 | N-(((5R,8S)-3-(2,6-difluorophenyl)-9,9-dimethyl-5,6,7,8-tetrahydro-5,8-methanocinnolin-8-yl)methyl)-N-ethyl-1H-1,2,4-triazole-5-sulfonamide | 0.0579 |
| 130 | 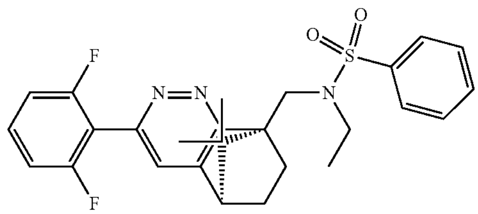 | N-(((5R,8S)-3-(2,6-difluorophenyl)-9,9-dimethyl-5,6,7,8-tetrahydro-5,8-methanocinnolin-8-yl)methyl)-N-ethylbenzenesulfonamide | 0.0093 |
| 131 | 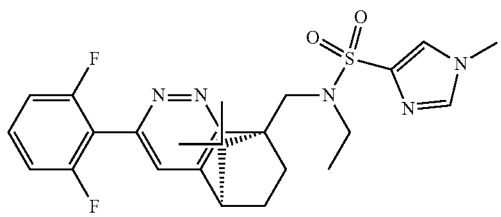 | N-(((5R,8S)-3-(2,6-difluorophenyl)-9,9-dimethyl-5,6,7,8-tetrahydro-5,8-methanocinnolin-8-yl)methyl)-N-ethyl-1-methyl-1H-imidazole-4-sulfonamide | 0.137 |
| 132 | 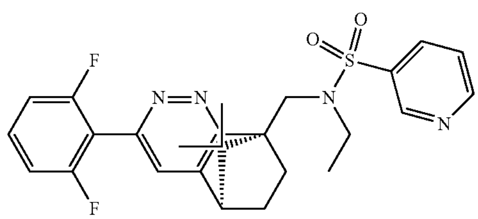 | N-(((5R,8S)-3-(2,6-difluorophenyl)-9,9-dimethyl-5,6,7,8-tetrahydro-5,8-methanocinnolin-8-yl)methyl)-N-ethylpyridine-3-sulfonamide | 0.0241 |
| 133 | 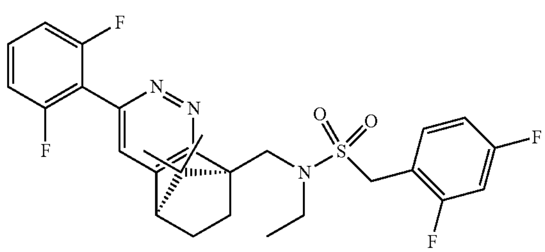 | 1-(2,4-difluorophenyl)-N-(((5R,8S)-3-(2,6-difluorophenyl)-9,9-dimethyl-5,6,7,8-tetrahydro-5,8-methanocinnolin-8-yl)methyl)-N-ethylmethanesulfonamide | 0.0026 |
| 134 | 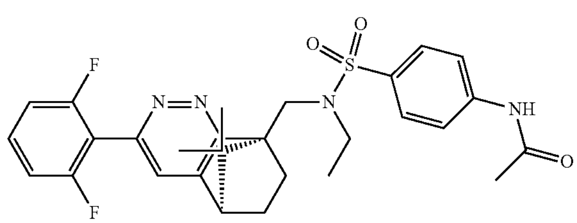 | N-(4-(N-(((5R,8S)-3-(2,6-difluorophenyl)-9,9-dimethyl-5,6,7,8-tetrahydro-5,8-methanocinnolin-8-yl)methyl)-N-ethylsulfamoyl)phenyl)acetamide | 0.0055 |
| 135 | 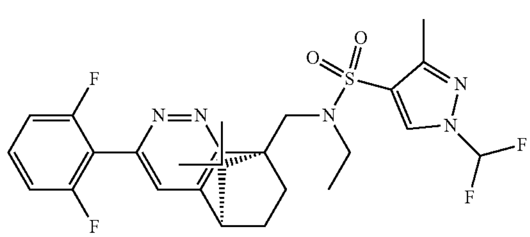 | 1-(difluoromethyl)-N-(((5R,8S)-3-(2,6-difluorophenyl)-9,9-dimethyl-5,6,7,8-tetrahydro-5,8-methanocinnolin-8-yl)methyl)-N-ethyl-3-methyl-1H-pyrazole-4-sulfonamide | 0.011 |

TABLE 1-continued

| | Structure | Name | IC$_{50}$ |
|---|---|---|---|
| 136 | 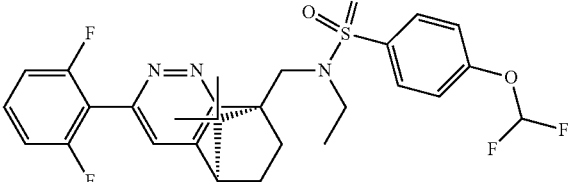 | 4-(difluoromethoxy)-N-(((5R,8S)-3-(2,6-difluorophenyl)-9,9-dimethyl-5,6,7,8-tetrahydro-5,8-methanocinnolin-8-yl)methyl)-N-ethylbenzenesulfonamide | 0.0109 |
| 137 | 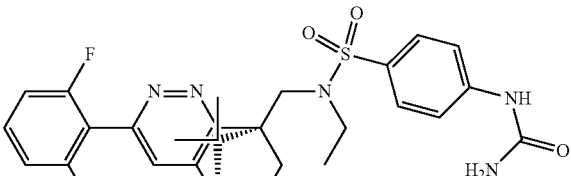 | N-(((5R,8S)-3-(2,6-difluorophenyl)-9,9-dimethyl-5,6,7,8-tetrahydro-5,8-methanocinnolin-8-yl)methyl)-N-ethyl-4-ureidobenzenesulfonamide | 0.0065 |
| 138 | 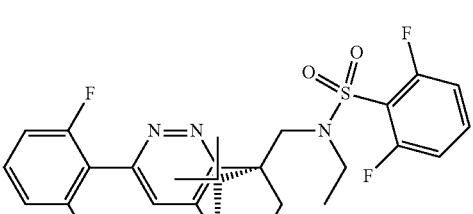 | N-(((5R,8S)-3-(2,6-difluorophenyl)-9,9-dimethyl-5,6,7,8-tetrahydro-5,8-methanocinnolin-8-yl)methyl)-N-ethyl-2,6-difluorobenzenesulfonamide | 0.00564 |
| 139 | 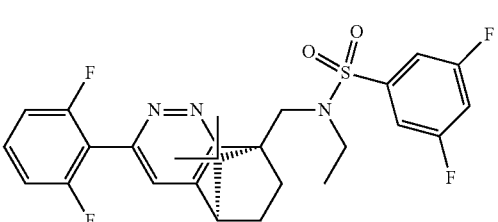 | N-(((5R,8S)-3-(2,6-difluorophenyl)-9,9-dimethyl-5,6,7,8-tetrahydro-5,8-methanocinnolin-8-yl)methyl)-N-ethyl-3,5-difluorobenzenesulfonamide | 0.0219 |
| 140 | 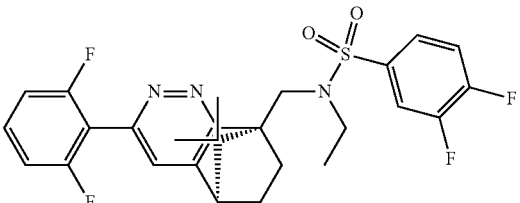 | N-(((5R,8S)-3-(2,6-difluorophenyl)-9,9-dimethyl-5,6,7,8-tetrahydro-5,8-methanocinnolin-8-yl)methyl)-N-ethyl-3,4-difluorobenzenesulfonamide | 0.0203 |
| 141 | 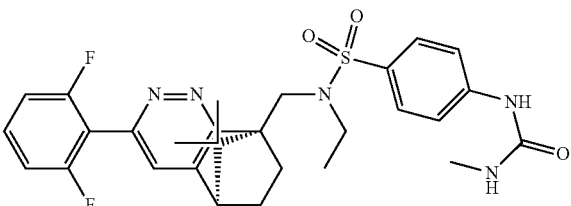 | N-(((5R,8S)-3-(2,6-difluorophenyl)-9,9-dimethyl-5,6,7,8-tetrahydro-5,8-methanocinnolin-8-yl)methyl)-N-ethyl-4-(3-methylureido)benzenesulfonamide | 0.0087 |
| 142 | 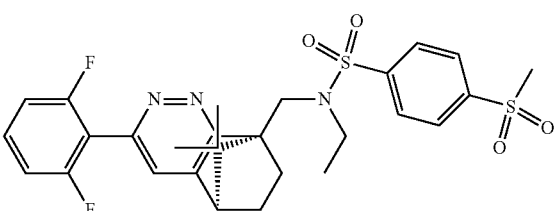 | N-(((5R,8S)-3-(2,6-difluorophenyl)-9,9-dimethyl-5,6,7,8-tetrahydro-5,8-methanocinnolin-8-yl)methyl)-N-ethyl-4-(methylsulfonyl)benzenesulfonamide | 0.0338 |

TABLE 1-continued

| | Structure | Name | IC$_{50}$ |
|---|---|---|---|
| 143 | 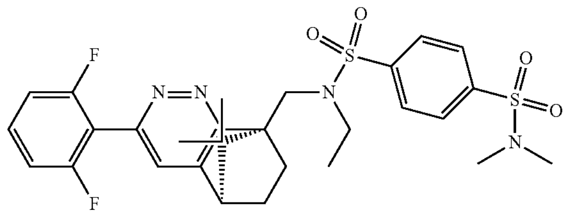 | N1-(((5R,8S)-3-(2,6-difluorophenyl)-9,9-dimethyl-5,6,7,8-tetrahydro-5,8-methanocinnolin-8-yl)methyl)-N1-ethyl-N4,N4-dimethylbenzene-1,4-disulfonamide | 0.0279 |
| 144 | 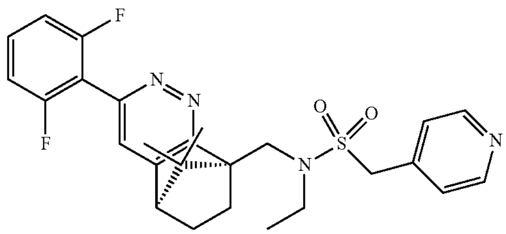 | N-(((5R,8S)-3-(2,6-difluorophenyl)-9,9-dimethyl-5,6,7,8-tetrahydro-5,8-methanocinnolin-8-yl)methyl)-N-ethyl-1-(pyridin-4-yl)methanesulfonamide | 0.0108 |
| 145 | 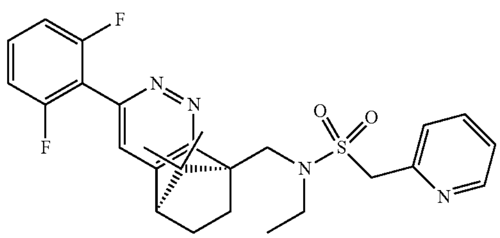 | N-(((5R,8S)-3-(2,6-difluorophenyl)-9,9-dimethyl-5,6,7,8-tetrahydro-5,8-methanocinnolin-8-yl)methyl)-N-ethyl-1-(pyridin-2-yl)methanesulfonamide | 0.0092 |
| 146 | 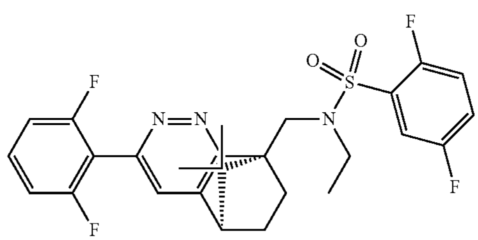 | N-(((5R,8S)-3-(2,6-difluorophenyl)-9,9-dimethyl-5,6,7,8-tetrahydro-5,8-methanocinnolin-8-yl)methyl)-N-ethyl-2,5-difluorobenzenesulfonamide | 0.0079 |
| 147 | 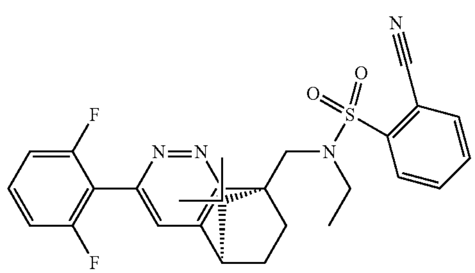 | 2-cyano-N-(((5R,8S)-3-(2,6-difluorophenyl)-9,9-dimethyl-5,6,7,8-tetrahydro-5,8-methanocinnolin-8-yl)methyl)-N-ethylbenzenesulfonamide | 0.0036 |
| 148 | 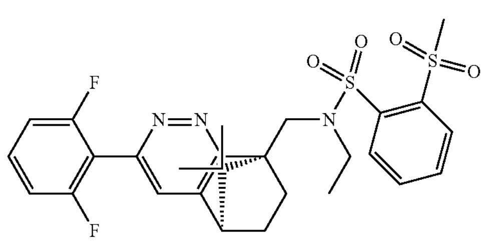 | N-(((5R,8S)-3-(2,6-difluorophenyl)-9,9-dimethyl-5,6,7,8-tetrahydro-5,8-methanocinnolin-8-yl)methyl)-N-ethyl-2-(methylsulfonyl)benzenesulfonamide | 0.0198 |

TABLE 1-continued

| | Structure | Name | IC$_{50}$ |
|---|---|---|---|
| 149 | 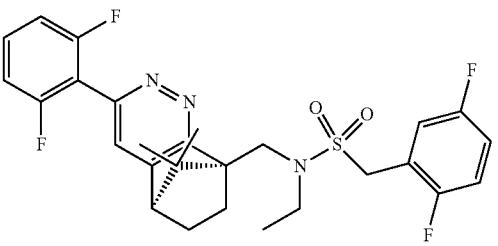 | 1-(2,5-difluorophenyl)-N-(((5R,8S)-3-(2,6-difluorophenyl)-9,9-dimethyl-5,6,7,8-tetrahydro-5,8-methanocinnolin-8-yl)methyl)-N-ethylmethanesulfonamide | 0.0029 |
| 150 | 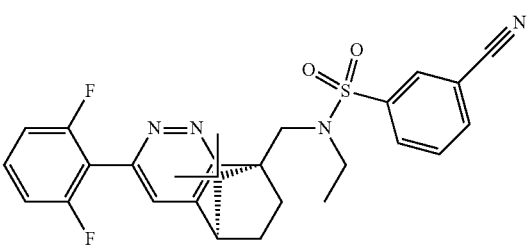 | 3-cyano-N-(((5R,8S)-3-(2,6-difluorophenyl)-9,9-dimethyl-5,6,7,8-tetrahydro-5,8-methanocinnolin-8-yl)methyl)-N-ethylbenzenesulfonamide | 0.0113 |
| 151 | 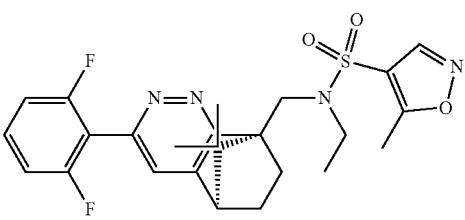 | N-(((5R,8S)-3-(2,6-difluorophenyl)-9,9-dimethyl-5,6,7,8-tetrahydro-5,8-methanocinnolin-8-yl)methyl)-N-ethyl-5-methylisoxazole-4-sulfonamide | 0.0259 |
| 152 | 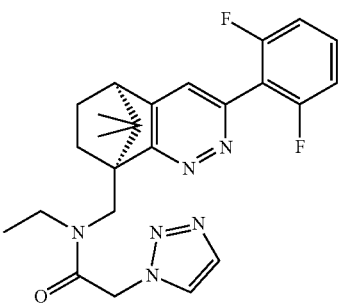 | N-(((5R,8S)-3-(2,6-difluorophenyl)-9,9-dimethyl-5,6,7,8-tetrahydro-5,8-methanocinnolin-8-yl)methyl)-N-ethyl-2-(1H-1,2,3-triazol-1-yl)acetamide | 0.0595 |
| 153 | 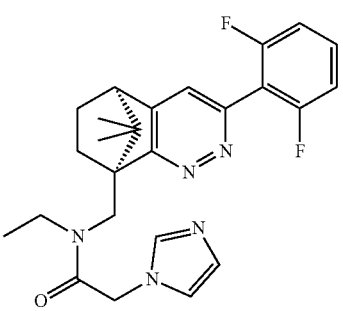 [SMILES: CCN(C[C@@]12CC[C@@H](c3cc(-c4c(F)cccc4F)nnc31)C2(C)C)C(=O)Cn1ccnc1] | N-(((5R,8S)-3-(2,6-difluorophenyl)-9,9-dimethyl-5,6,7,8-tetrahydro-5,8-methanocinnolin-8-yl)methyl)-N-ethyl-2-(1H-imidazol-1-yl)acetamide | 0.0492 |

TABLE 1-continued

| Structure | Name | IC$_{50}$ |
|---|---|---|
| 154 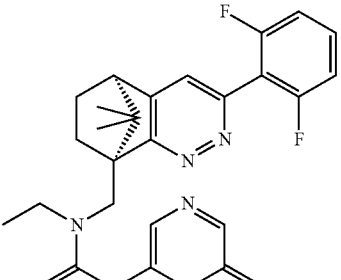 | N-(((5R,8S)-3-(2,6-difluorophenyl)-9,9-dimethyl-5,6,7,8-tetrahydro-5,8-methanocinnolin-8-yl)methyl)-N-ethyl-2-(6-oxo-1,6-dihydropyrazin-2-yl)acetamide | 0.0623 |
| 155 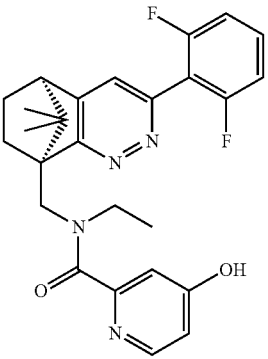 [SMILES: CCN(C[C@@]12CC[C@@H](c3cc(-c4c(F)cccc4F)nnc31)C2(C)C)C(=O)c1cc(O)ccn1] | N-(((5R,8S)-3-(2,6-difluorophenyl)-9,9-dimethyl-5,6,7,8-tetrahydro-5,8-methanocinnolin-8-yl)methyl)-N-ethyl-4-hydroxypicolinamide | 0.0969 |
| 156 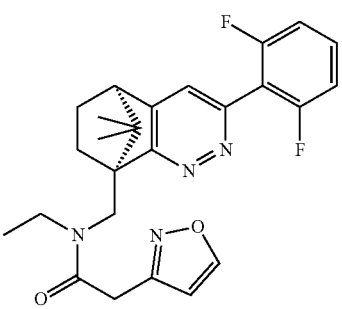 [SMILES: CCN(C[C@@]12CC[C@@H](c3cc(-c4c(F)cccc4F)nnc31)C2(C)C)C(=O)Cc1ccon1] | N-(((5R,8S)-3-(2,6-difluorophenyl)-9,9-dimethyl-5,6,7,8-tetrahydro-5,8-methanocinnolin-8-yl)methyl)-N-ethyl-2-(isoxazol-3-yl)acetamide | 0.0132 |
| 157 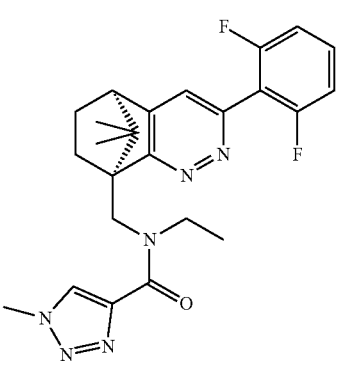 [SMILES: CCN(C[C@@]12CC[C@@H](c3cc(-c4c(F)cccc4F)nnc31)C2(C)C)C(=O)c1cn(C)nn1] | N-(((5R,8S)-3-(2,6-difluorophenyl)-9,9-dimethyl-5,6,7,8-tetrahydro-5,8-methanocinnolin-8-yl)methyl)-N-ethyl-2-(isoxazol-3-yl)acetamide | 0.0176 |

TABLE 1-continued

| Structure | | Name | IC$_{50}$ |
|---|---|---|---|
| 158 | 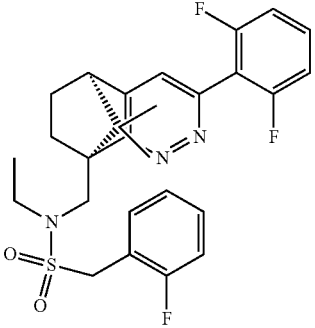 | N-(((5R,8S)-3-(2,6-difluorophenyl)-9,9-dimethyl-5,6,7,8-tetrahydro-5,8-methanocinnolin-8-yl)methyl)-N-ethyl-1-(2-fluorophenyl)methanesulfonamide | 0.0028 |
| 159 | 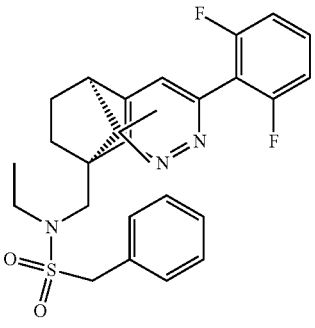 | N-(((5R,8S)-3-(2,6-difluorophenyl)-9,9-dimethyl-5,6,7,8-tetrahydro-5,8-methanocinnolin-8-yl)methyl)-N-ethyl-1-phenylmethanesulfonamide | 0.0035 |
| 160 | 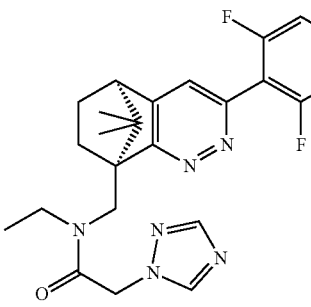 | N-(((5R,8S)-3-(2,6-difluorophenyl)-9,9-dimethyl-5,6,7,8-tetrahydro-5,8-methanocinnolin-8-yl)methyl)-N-ethyl-2-(1H-1,2,4-triazol-1-yl)acetamide | 0.012 |
| 161 | 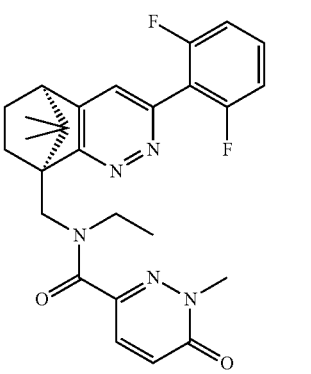 [SMILES: CCN(C[C@@]12CC[C@@H](c3cc(-c4c(F)cccc4F)nnc31)C2(C)C)C(=O)c1ccc(=O)n(C)n1] | N-(((5R,8S)-3-(2,6-difluorophenyl)-9,9-dimethyl-5,6,7,8-tetrahydro-5,8-methanocinnolin-8-yl)methyl)-N-ethyl-1-methyl-6-oxo-1,6-dihydropyridazine-3-carboxamide | 0.0164 |

TABLE 1-continued

| | Structure | Name | IC$_{50}$ |
|---|---|---|---|
| 162 | 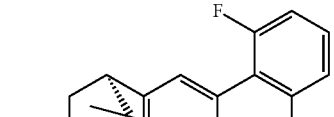 | N-(((5R,8S)-3-(2,6-difluorophenyl)-9,9-dimethyl-5,6,7,8-tetrahydro-5,8-methanocinnolin-8-yl)methyl)-N-ethyl-2-(5-oxo-4,5-dihydro-1H-1,2,4-triazol-3-yl)acetamide | 0.0193 |
| 163 | 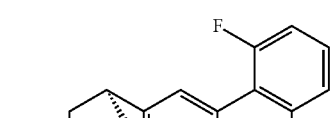 | N-(((5R,8S)-3-(2,6-difluorophenyl)-9,9-dimethyl-5,6,7,8-tetrahydro-5,8-methanocinnolin-8-yl)methyl)-N-ethyl-2-(6-oxo-1,6-dihydropyridazin-3-yl)acetamide | 0.0487 |
| 164 | 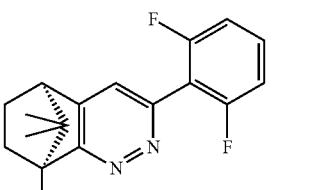 | methyl 5-(((((5R,8S)-3-(2,6-difluorophenyl)-9,9-dimethyl-5,6,7,8-tetrahydro-5,8-methanocinnolin-8-yl)methyl)(ethyl)carbamoyl)pyrazine-2-carboxylate | 0.0206 |
| 165 | 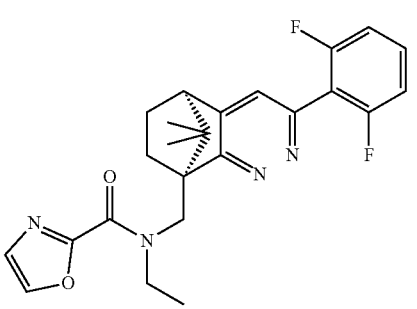 [SMILES: CCN(C[C@@]12CC[C@@H](/C(=C/C(=N)c3c(F)cccc3F)C1=N)C2(C)C)C(=O)c1ncco1] | N-(((5R,8S)-3-(2,6-difluorophenyl)-9,9-dimethyl-5,6,7,8-tetrahydro-5,8-methanocinnolin-8-yl)methyl)-N-ethyloxazole-2-carboxamide | 0.0046 |

TABLE 1-continued

| | Structure | Name | IC$_{50}$ |
|---|---|---|---|
| 166 | 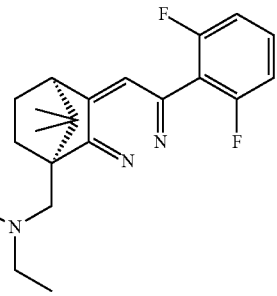 | N-(((5R,8S)-3-(2,6-difluorophenyl)-9,9-dimethyl-5,6,7,8-tetrahydro-5,8-methanocinnolin-8-yl)methyl)-N-ethyl-5-methyloxazole-4-carboxamide | 0.0089 |
| 167 | 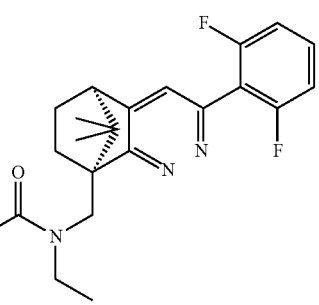 | N-(((5R,8S)-3-(2,6-difluorophenyl)-9,9-dimethyl-5,6,7,8-tetrahydro-5,8-methanocinnolin-8-yl)methyl)-N-ethyl-2-methyloxazole-5-carboxamide | 0.012 |
| 168 | 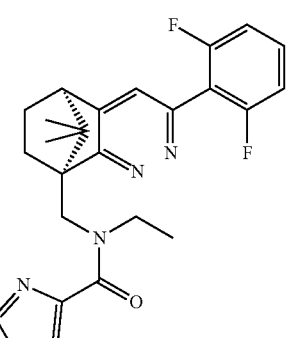 | 2-amino-N-(((5R,8S)-3-(2,6-difluorophenyl)-9,9-dimethyl-5,6,7,8-tetrahydro-5,8-methanocinnolin-8-yl)methyl)-N-ethyloxazole-4-carboxamide | 0.0294 |
| 169 | 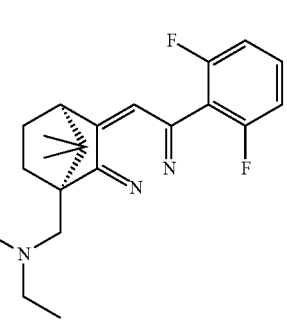 | N-(((5R,8S)-3-(2,6-difluorophenyl)-9,9-dimethyl-5,6,7,8-tetrahydro-5,8-methanocinnolin-8-yl)methyl)-N-ethyl-4-methyl-1H-imidazole-2-carboxamide | 0.0175 |
| 170 | 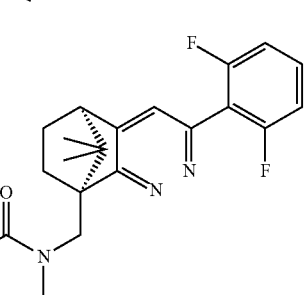 | N-(((5R,8S)-3-(2,6-difluorophenyl)-9,9-dimethyl-5,6,7,8-tetrahydro-5,8-methanocinnolin-8-yl)methyl)-2-(1,1-dioxidothiomorpholino)-N-ethylacetamide | 0.0619 |

TABLE 1-continued

| | Structure | Name | IC$_{50}$ |
|---|---|---|---|
| 171 | 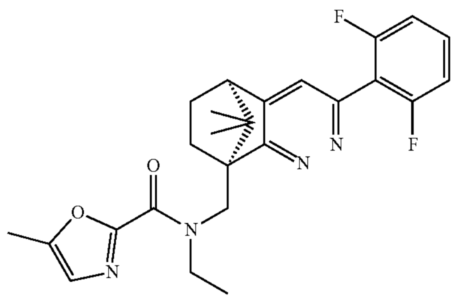 [SMILES: CCN(C[C@@]12CC[C@@H](/C(=C/C(=N)c3c(F)cccc3F)C1=N)C2(C)C)C(=O)c1ncc(C)o1] | N-(((5R,8S)-3-(2,6-difluorophenyl)-9,9-dimethyl-5,6,7,8-tetrahydro-5,8-methanocinnolin-8-yl)methyl)-N-ethyl-5-methyloxazole-2-carboxamide | 0.0077 |
| 172 | 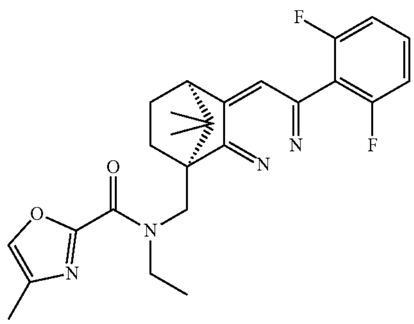 [SMILES: CCN(C[C@@]12CC[C@@H](/C(=C/C(=N)c3c(F)cccc3F)C1=N)C2(C)C)C(=O)c1nc(C)co1] | N-(((5R,8S)-3-(2,6-difluorophenyl)-9,9-dimethyl-5,6,7,8-tetrahydro-5,8-methanocinnolin-8-yl)methyl)-N-ethyl-4-methyloxazole-2-carboxamide | 0.0079 |
| 173 | 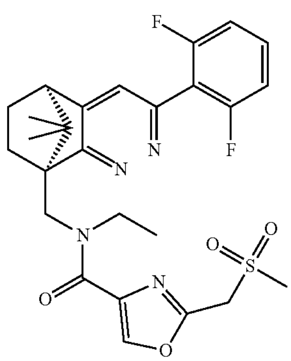 [SMILES: CCN(C[C@@]12CC[C@@H](/C(=C/C(=N)c3c(F)cccc3F)C1=N)C2(C)C)C(=O)c1coc(CS(C)(=O)=O)n1] | N-(((5R,8S)-3-(2,6-difluorophenyl)-9,9-dimethyl-5,6,7,8-tetrahydro-5,8-methanocinnolin-8-yl)methyl)-N-ethyl-2-((methylsulfonyl)methyl)oxazole-4-carboxamide | 0.0175 |
| 175 | 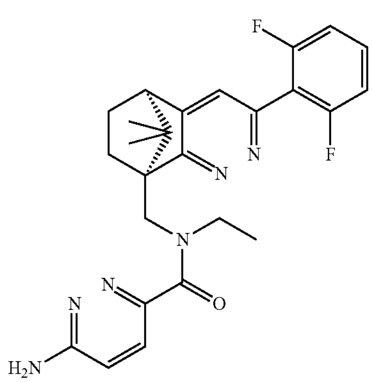 [SMILES: CCN(C[C@@]12CC[C@@H](/C(=C/C(=N)c3c(F)cccc3F)C1=N)C2(C)C)C(=O)C(=N)/C=C\C(=N)N] | 6-amino-N-(((5R,8S)-3-(2,6-difluorophenyl)-9,9-dimethyl-5,6,7,8-tetrahydro-5,8-methanocinnolin-8-yl)methyl)-N-ethylpyridazine-3-carboxamide | 0.0357 |

TABLE 1-continued

| | Structure | Name | IC$_{50}$ |
|---|---|---|---|
| 175 | 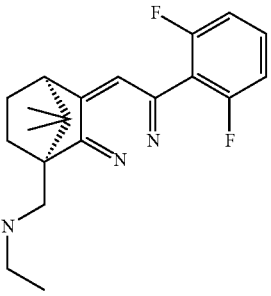 | N-(((5R,8S)-3-(2,6-difluorophenyl)-9,9-dimethyl-5,6,7,8-tetrahydro-5,8-methanocinnolin-8-yl)methyl)-N-ethyl-2,5-dimethyloxazole-4-carboxamide | 0.0148 |
| 176 | 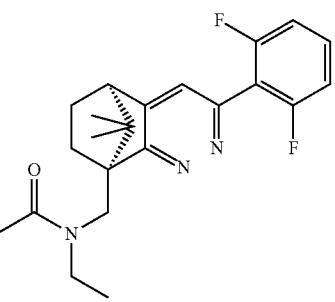 | N-(((5R,8S)-3-(2,6-difluorophenyl)-9,9-dimethyl-5,6,7,8-tetrahydro-5,8-methanocinnolin-8-yl)methyl)-N-ethyl-2-(methylsulfonamido)oxazole-4-carboxamide | 0.0437 |
| 177 | 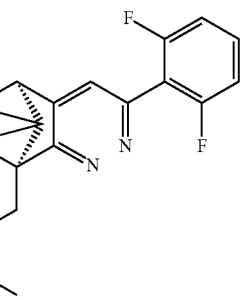 | N-(((5R,8S)-3-(2,6-difluorophenyl)-9,9-dimethyl-5,6,7,8-tetrahydro-5,8-methanocinnolin-8-yl)methyl)-N-ethyl-4-methylisoxazole-3-carboxamide | 0.0063 |
| 178 | 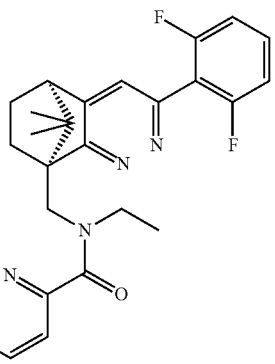 | 6-(cyanomethyl)-N-(((5R,8S)-3-(2,6-difluorophenyl)-9,9-dimethyl-5,6,7,8-tetrahydro-5,8-methanocinnolin-8-yl)methyl)-N-ethylpyridazine-3-carboxamide | 0.0937 |
| 179 | 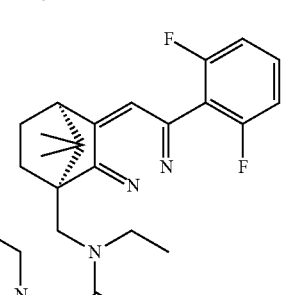 | N-(((5R,8S)-3-(2,6-difluorophenyl)-9,9-dimethyl-5,6,7,8-tetrahydro-5,8-methanocinnolin-8-yl)methyl)-N-ethyl-2-(4-hydroxypiperidin-1-yl)acetamide | 0.306 |

TABLE 1-continued

| | Structure | Name | IC$_{50}$ |
|---|---|---|---|
| 180 | 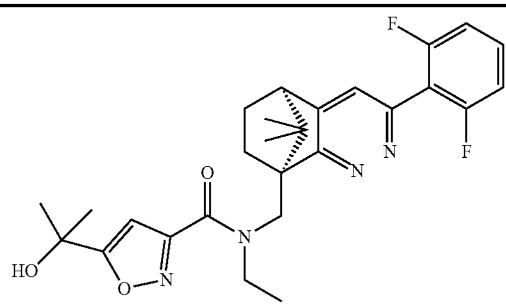 | N-(((5R,8S)-3-(2,6-difluorophenyl)-9,9-dimethyl-5,6,7,8-tetrahydro-5,8-methanocinnolin-8-yl)methyl)-N-ethyl-5-(2-hydroxypropan-2-yl)isoxazole-3-carboxamide | 0.0269 |
| 181 | 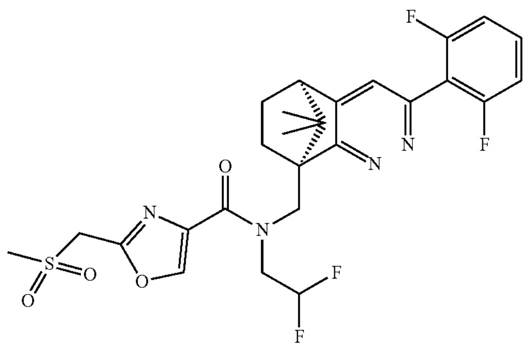 [SMILES: CC1(C)[C@H]2CC[C@]1(CN(CC(F)F)C(=O)c1coc(CS(C)(=O)=O)n1)C(=N)/C2=C\C(=N)c1c(F)cccc1F] | N-(2,2-difluoroethyl)-N-[[(1S,8R)-5-(2,6-difluorophenyl)-11,11-dimethyl-3,4-diazatricyclo[6.2.1.02,7]undeca-2(7),3,5-trien-1-yl]methyl]-2-(methylsulfonylmethyl)oxazole-4-carboxamide | 0.045 |
| 182 | 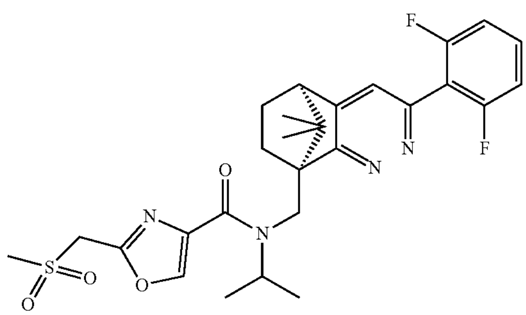 [SMILES: CC(C)N(C[C@@]12CC[C@@H](/C(=C/C(=N)c3c(F)cccc3F)C1=N)C2(C)C)C(=O)c1coc(CS(C)(=O)=O)n1] | N-[[(1S,8R)-5-(2,6-difluorophenyl)-11,11-dimethyl-3,4-diazatricyclo[6.2.1.02,7]undeca-2(7),3,5-trien-1-yl]methyl]-N-isopropyl-2-(methylsulfonylmethyl)oxazole-4-carboxamide | 0.082 |
| 183 | 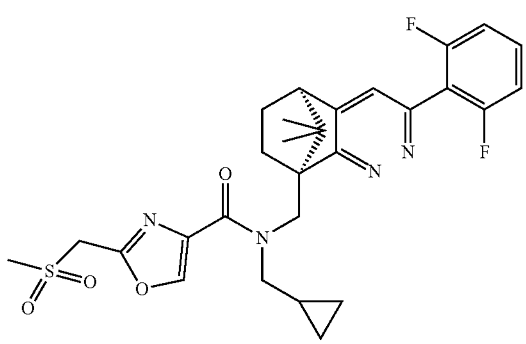 [SMILES: CC1(C)[C@H]2CC[C@]1(CN(CC1CC1)C(=O)c1coc(CS(C)(=O)=O)n1)C(=N)/C2=C\C(=N)c1c(F)cccc1F] | N-(cyclopropylmethyl)-N-[[(1S,8R)-5-(2,6-difluorophenyl)-11,11-dimethyl-3,4-diazatricyclo[6.2.1.02,7]undeca-2(7),3,5-trien-1-yl]methyl]-2-(methylsulfonylmethyl)oxazole-4-carboxamide | 0.057 |
| 184 | 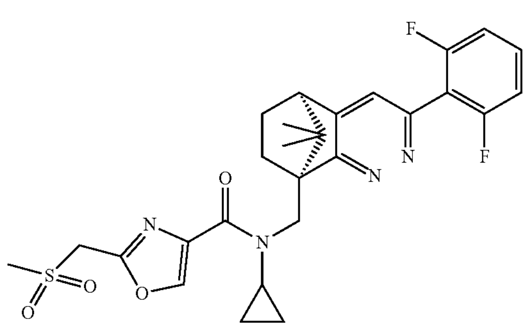 [SMILES: CC1(C)[C@H]2CC[C@]1(CN(C(=O)c1coc(CS(C)(=O)=O)n1)C1CC1)C(=N)/C2=C\C(=N)c1c(F)cccc1F] | N-cyclopropyl-N-[[(1S,8R)-5-(2,6-difluorophenyl)-11,11-dimethyl-3,4-diazatricyclo[6.2.1.02,7]undeca-2(7),3,5-trien-1-yl]methyl]-2-(methylsulfonylmethyl)oxazole-4-carboxamide | 0.075 |

TABLE 1-continued

| | Structure | Name | IC$_{50}$ |
|---|---|---|---|
| 184 | 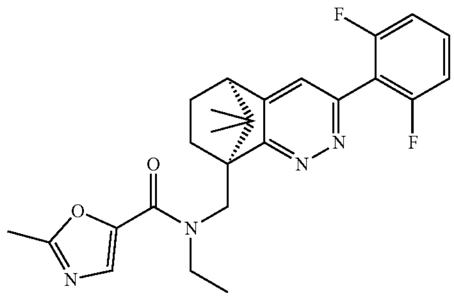 [SMILES: CCN(C[C@@]12CC[C@@H](c3cc(-c4c(F)cccc4F)nnc31)C2(C)C)C(=O)c1cnc(C)o1] | N-[[(1S,8R)-5-(2,6-difluorophenyl)-11,11-dimethyl-3,4-diazatricyclo[6.2.1.02,7]undeca-2,4,6-trien-1-yl]methyl]-N-ethyl-5-methyl-oxazole-2-carboxamide | 0.0036 |
| 185 | 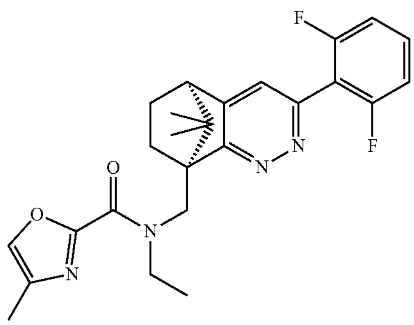 [SMILES: CCN(C[C@@]12CC[C@@H](c3cc(-c4c(F)cccc4F)nnc31)C2(C)C)C(=O)c1nc(C)co1] | N-[[(1S,8R)-5-(2,6-difluorophenyl)-11,11-dimethyl-3,4-diazatricyclo[6.2.1.02,7]undeca-2,4,6-trien-1-yl]methyl]-N-ethyl-4-methyl-oxazole-2-carboxamide | 0.055 |
| 186 | 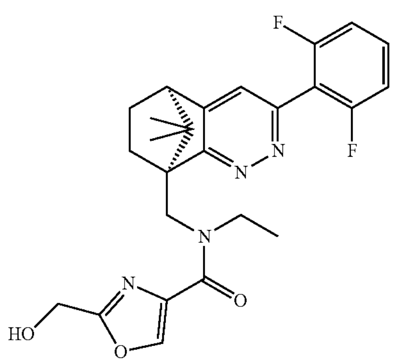 [SMILES: CCN(C[C@@]12CC[C@@H](c3cc(-c4c(F)cccc4F)nnc31)C2(C)C)C(=O)c1coc(CO)n1] | N-[[(1S,8R)-5-(2,6-difluorophenyl)-11,11-dimethyl-3,4-diazatricyclo[6.2.1.02,7]undeca-2,4,6-trien-1-yl]methyl]-N-ethyl-2-(hydroxymethyl)oxazole-4-carboxamide | 0.0056 |
| 187 | 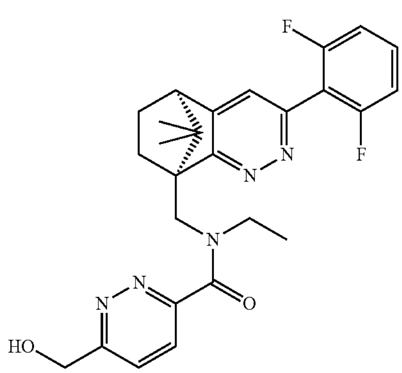 [SMILES: CCN(C[C@@]12CC[C@@H](c3cc(-c4c(F)cccc4F)nnc31)C2(C)C)C(=O)c1ccc(CO)nn1] | N-[[(1S,8R)-5-(2,6-difluorophenyl)-11,11-dimethyl-3,4-diazatricyclo[6.2.1.02,7]undeca-2,4,6-trien-1-yl]methyl]-N-ethyl-6-(hydroxymethyl)pyridazine-3-carboxamide | 0.026 |

TABLE 1-continued

| | Structure | Name | IC$_{50}$ |
|---|---|---|---|
| 188 | 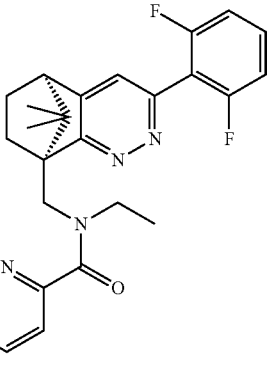 | N-[[(1S,8R)-5-(2,6-difluorophenyl)-11,11-dimethyl-3,4-diazatricyclo[6.2.1.02,7]undeca-2,4,6-trien-1-yl]methyl]-N-ethyl-6-(methylsulfonylmethyl)pyridazine-3-carboxamide | 0.0045 |
| 189 | 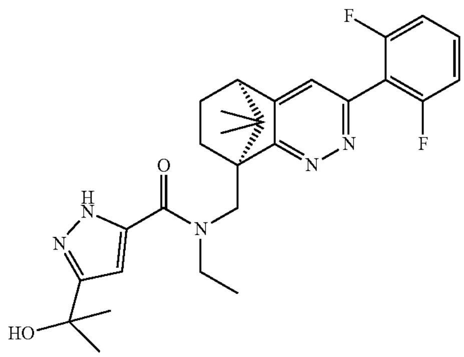 [SMILES: CCN(C[C@@]12CC[C@@H](c3cc(-c4c(F)cccc4F)nnc31)C2(C)C)C(=O)c1cc(C(C)(C)O)n[nH]1] | N-[[(1S,8R)-5-(2,6-difluorophenyl)-11,11-dimethyl-3,4-diazatricyclo[6.2.1.02,7]undeca-2,4,6-trien-1-yl]methyl]-N-ethyl-3-(1-hydroxy-1-methyl-ethyl)-1H-pyrazole-5-carboxamide | 0.038 |
| 190 | 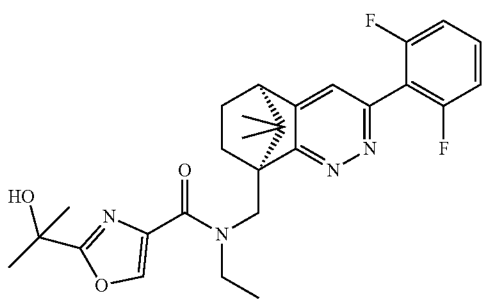 [SMILES: CCN(C[C@@]12CC[C@@H](c3cc(-c4c(F)cccc4F)nnc31)C2(C)C)C(=O)c1coc(C(C)(C)O)n1] | N-[[(1S,8R)-5-(2,6-difluorophenyl)-11,11-dimethyl-3,4-diazatricyclo[6.2.1.02,7]undeca-2,4,6-trien-1-yl]methyl]-N-ethyl-2-(1-hydroxy-1-methyl-ethyl)oxazole-4-carboxamide | 0.035 |
| 191 | 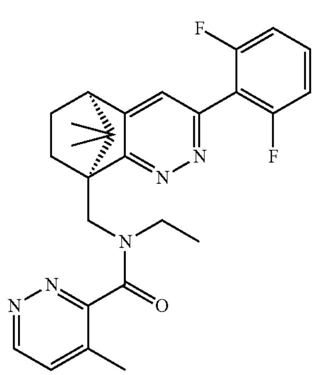 [SMILES: CCN(C[C@@]12CC[C@@H](c3cc(-c4c(F)cccc4F)nnc31)C2(C)C)C(=O)c1nnccc1C] | N-[[(1S,8R)-5-(2,6-difluorophenyl)-11,11-dimethyl-3,4-diazatricyclo[6.2.1.02,7]undeca-2,4,6-trien-1-yl]methyl]-N-ethyl-4-methyl-pyridazine-3-carboxamide | 0.011 |

TABLE 1-continued

| | Structure | Name | IC$_{50}$ |
|---|---|---|---|
| 192 | 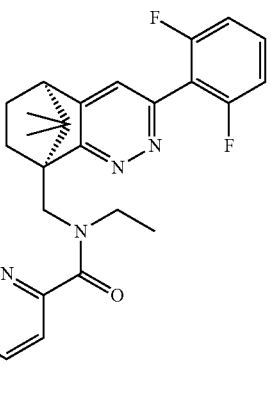 | N-[[(1S,8R)-5-(2,6-difluorophenyl)-11,11-dimethyl-3,4-diazatricyclo[6.2.1.02,7]undeca-2,4,6-trien-1-yl]methyl]-N-ethyl-6-(1-hydroxy-1-methyl-ethyl)pyridazine-3-carboxamide | 0.14 |
| 193 | 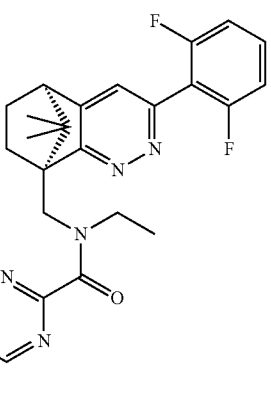 | N-[[(1S,8R)-5-(2,6-difluorophenyl)-11,11-dimethyl-3,4-diazatricyclo[6.2.1.02,7]undeca-2,4,6-trien-1-yl]methyl]-N-ethyl-5-(1-hydroxy-1-methyl-ethyl)pyrimidine-2-carboxamide | 0.0084 |
| 194 | 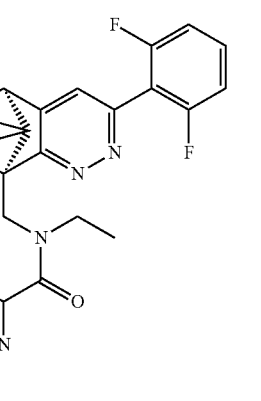 | N-[[(1S,8R)-5-(2,6-difluorophenyl)-11,11-dimethyl-3,4-diazatricyclo[6.2.1.02,7]undeca-2,4,6-trien-1-yl]methyl]-N-ethyl-5-hydroxy-pyrimidine-2-carboxamide | 0.0020 |
| 195 | 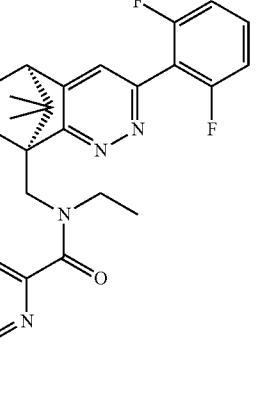 | 5-cyano-N-[[(1S,8R)-5-(2,6-difluorophenyl)-11,11-dimethyl-3,4-diazatricyclo[6.2.1.02,7]undeca-2,4,6-trien-1-yl]methyl]-N-ethyl-pyrimidine-2-carboxamide | 0.021 |

TABLE 1-continued

| | Structure | Name | IC$_{50}$ |
|---|---|---|---|
| 196 | 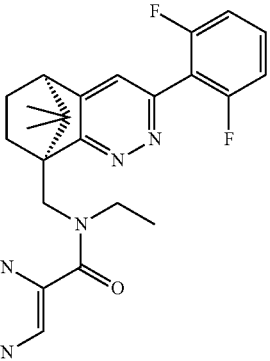 | N-[[(1S,8R)-5-(2,6-difluorophenyl)-11,11-dimethyl-3,4-diazatricyclo[6.2.1.02,7]undeca-2,4,6-trien-1-yl]methyl]-N-ethyl-6-(hydroxymethyl)pyrazine-2-carboxamide | 0.062 |
| 197 | 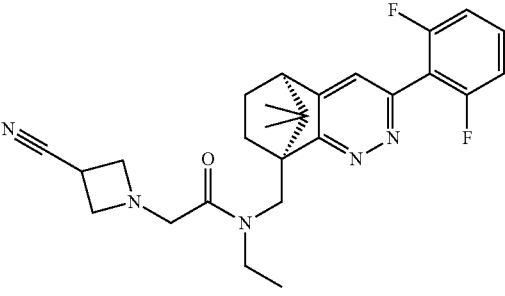 [SMILES: CCN(C[C@@]12CC[C@@H](c3cc(-c4c(F)cccc4F)nnc31)C2(C)C)C(=O)CN1CC(C#N)C1] | 2-(3-cyanoazetidin-1-yl)-N-[[(1S,8R)-5-(2,6-difluorophenyl)-11,11-dimethyl-3,4-diazatricyclo[6.2.1.02,7]undeca-2,4,6-trien-1-yl]methyl]-N-ethyl-acetamide | 0.016 |
| 198 | 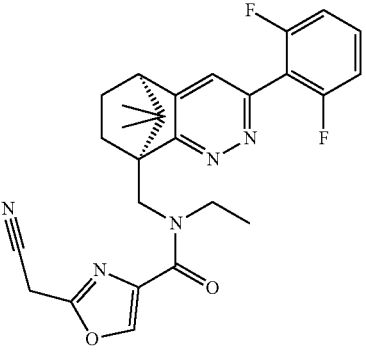 [SMILES: CCN(C[C@@]12CC[C@@H](c3cc(-c4c(F)cccc4F)nnc31)C2(C)C)C(=O)c1coc(CC#N)n1] | 2-(cyanomethyl)-N-[[(1S,8R)-5-(2,6-difluorophenyl)-11,11-dimethyl-3,4-diazatricyclo[6.2.1.02,7]undeca-2,4,6-trien-1-yl]methyl]-N-ethyl-oxazole-4-carboxamide | 0.042 |
| 199 | 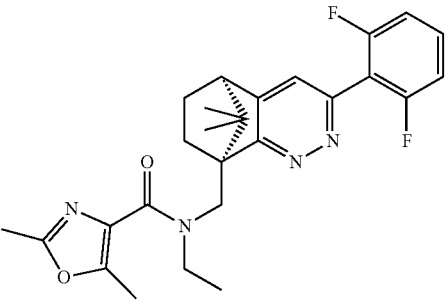 [SMILES: CCN(C[C@@]12CC[C@@H](c3cc(-c4c(F)cccc4F)nnc31)C2(C)C)C(=O)c1nc(C)oc1C] | N-[1-[5-(2,6-difluorophenyl)-11,11-dimethyl-3,4-diazatricyclo[6.2.1.02,7]undeca-2,4,6-trien-1-yl]ethyl]-N-ethyl-2,5-dimethyl-oxazole-4-carboxamide | 0.039 |

TABLE 1-continued

| | Structure | Name | IC$_{50}$ |
|---|---|---|---|
| 200 | 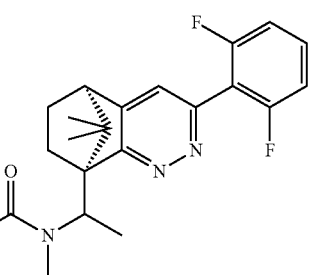 | N-[1-[5-(2,6-difluorophenyl)-11,11-dimethyl-3,4-diazatricyclo[6.2.1.02,7]undeca-2,4,6-trien-1-yl]ethyl]-N-ethyl-oxazole-2-carboxamide | 0.020 |
| 201 | 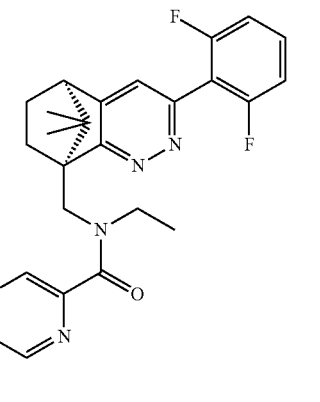 | N-[[(1S,8R)-5-(2,6-difluorophenyl)-11,11-dimethyl-3,4-diazatricyclo[6.2.1.02,7]undeca-2,4,6-trien-1-yl]methyl]-N-ethyl-5-(1-hydroxy-1-methyl-ethyl)pyrazine-2-carboxamide | 0.013 |
| 202 | 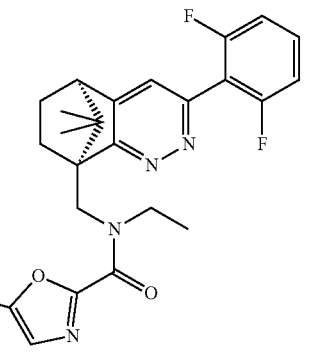 | N-[[(1S,8R)-5-(2,6-difluorophenyl)-11,11-dimethyl-3,4-diazatricyclo[6.2.1.02,7]undeca-2,4,6-trien-1-yl]methyl]-N-ethyl-5-(1-hydroxy-1-methyl-ethyl)oxazole-2-carboxamide | 0.0054 |
| 203 | 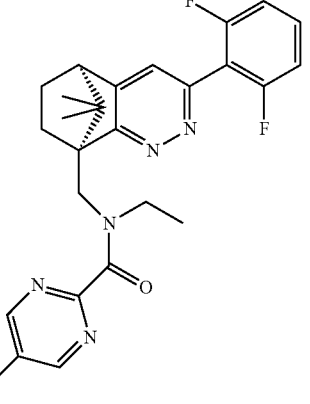 | N-[[(1S,8R)-5-(2,6-difluorophenyl)-11,11-dimethyl-3,4-diazatricyclo[6.2.1.02,7]undeca-2,4,6-trien-1-yl]methyl]-N-ethyl-5-(methylsulfonylmethyl)pyrimidine-2-carboxamide | 0.013 |

TABLE 1-continued

| | Structure | Name | IC$_{50}$ |
|---|---|---|---|
| 204 | 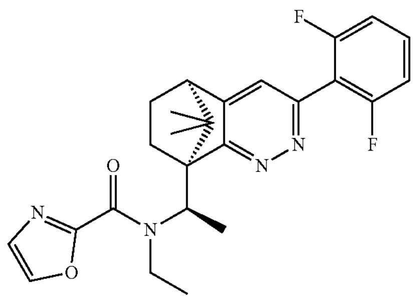 [SMILES: CCN(C(=O)c1ncco1)[C@H](C)[C@@]12CC[C@@H](c3cc(-c4c(F)cccc4F)nnc31)C2(C)C] | N-[1-[5-(2,6-difluorophenyl)-11,11-dimethyl-3,4-diazatricyclo[6.2.1.02,7]undeca-2,4,6-trien-1-yl]ethyl]-N-ethyl-oxazole-2-carboxamide | 0.014 |
| 205 | 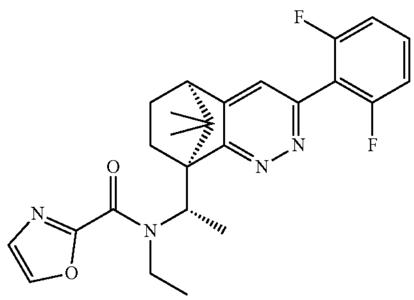 [SMILES: CCN(C(=O)c1ncco1)[C@@H](C)[C@@]12CC[C@@H](c3cc(-c4c(F)cccc4F)nnc31)C2(C)C] | N-[1-[5-(2,6-difluorophenyl)-11,11-dimethyl-3,4-diazatricyclo[6.2.1.02,7]undeca-2,4,6-trien-1-yl]ethyl]-N-ethyl-oxazole-2-carboxamide | 0.30 |
| 206 | 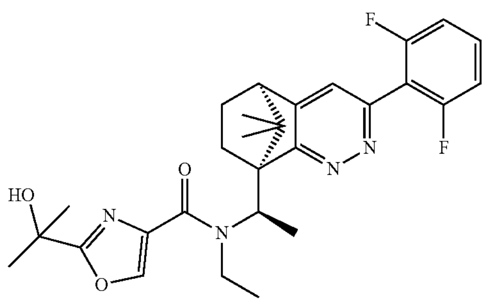 [SMILES: CCN(C(=O)c1coc(C(C)(C)O)n1)[C@H](C)[C@@]12CC[C@@H](c3cc(-c4c(F)cccc4F)nnc31)C2(C)C] | N-[1-[5-(2,6-difluorophenyl)-11,11-dimethyl-3,4-diazatricyclo[6.2.1.02,7]undeca-2,4,6-trien-1-yl]ethyl]-N-ethyl-2-(1-hydroxy-1-methyl-ethyl)oxazole-4-carboxamide | 0.0068 |
| 207 | 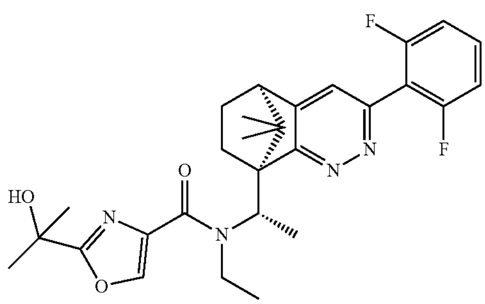 [SMILES: CCN(C(=O)c1coc(C(C)(C)O)n1)[C@@H](C)[C@@]12CC[C@@H](c3cc(-c4c(F)cccc4F)nnc31)C2(C)C] | N-[1-[5-(2,6-difluorophenyl)-11,11-dimethyl-3,4-diazatricyclo[6.2.1.02,7]undeca-2,4,6-trien-1-yl]ethyl]-N-ethyl-2-(1-hydroxy-1-methyl-ethyl)oxazole-4-carboxamide | 0.0016 |
| 208 | 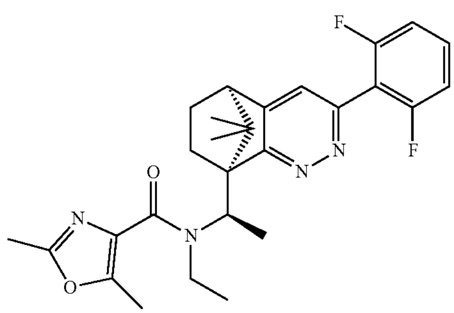 [SMILES: CCN(C(=O)c1nc(C)oc1C)[C@H](C)[C@@]12CC[C@@H](c3cc(-c4c(F)cccc4F)nnc31)C2(C)C] | N-[1-[5-(2,6-difluorophenyl)-11,11-dimethyl-3,4-diazatricyclo[6.2.1.02,7]undeca-2,4,6-trien-1-yl]ethyl]-N-ethyl-2,5-dimethyl-oxazole-4-carboxamide | 0.0035 |

TABLE 1-continued

| | Structure | Name | IC$_{50}$ |
|---|---|---|---|
| 209 | 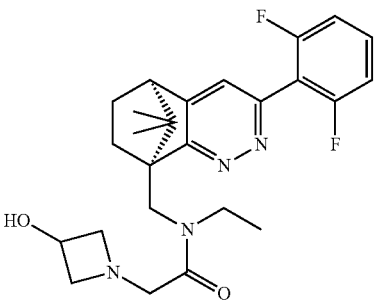 [SMILES: CCN(C[C@@]12CC[C@@H](c3cc(-c4c(F)cccc4F)nnc31)C2(C)C)C(=O)CN1CC(O)C1] | N-[[(1S,8R)-5-(2,6-difluorophenyl)-11,11-dimethyl-3,4-diazatricyclo[6.2.1.02,7]undeca-2,4,6-trien-1-yl]methyl]-N-ethyl-2-(3-hydroxyazetidin-1-yl)acetamide | 0.015 |
| 210 | 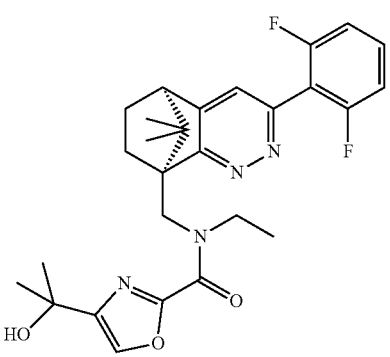 [SMILES: CCN(C[C@@]12CC[C@@H](c3cc(-c4c(F)cccc4F)nnc31)C2(C)C)C(=O)c1nc(C(C)(C)O)co1] | N-[[(1S,8R)-5-(2,6-difluorophenyl)-11,11-dimethyl-3,4-diazatricyclo[6.2.1.02,7]undeca-2,4,6-trien-1-yl]methyl]-N-ethyl-4-(1-hydroxy-1-methyl-ethyl)oxazole-2-carboxamide | 0.0043 |
| 211 | 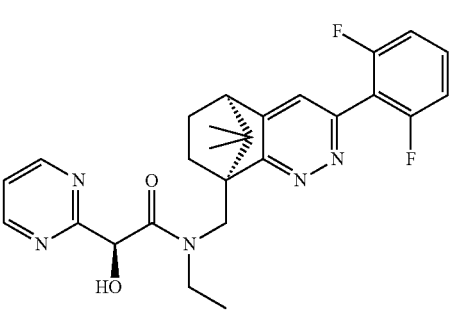 [SMILES: CCN(C[C@@]12CC[C@@H](c3cc(-c4c(F)cccc4F)nnc31)C2(C)C)C(=O)[C@@H](O)c1ncccn1] | N-[[5-(2,6-difluorophenyl)-11,11-dimethyl-3,4-diazatricyclo[6.2.1.02,7]undeca-2,4,6-trien-1-yl]methyl]-N-ethyl-2-hydroxy-2-pyrimidin-2-yl-acetamide | 0.15 |
| 212 | 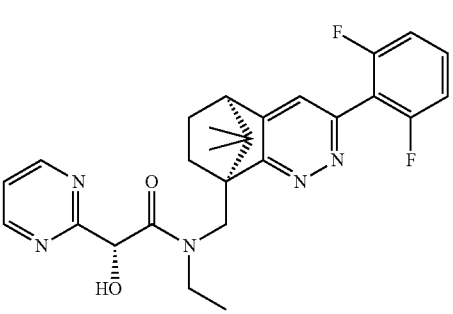 [SMILES: CCN(C[C@@]12CC[C@@H](c3cc(-c4c(F)cccc4F)nnc31)C2(C)C)C(=O)[C@H](O)c1ncccn1] | N-[[5-(2,6-difluorophenyl)-11,11-dimethyl-3,4-diazatricyclo[6.2.1.02,7]undeca-2,4,6-trien-1-yl]methyl]-N-ethyl-2-hydroxy-2-pyrimidin-2-yl-acetamide | 0.025 |
| 213 | 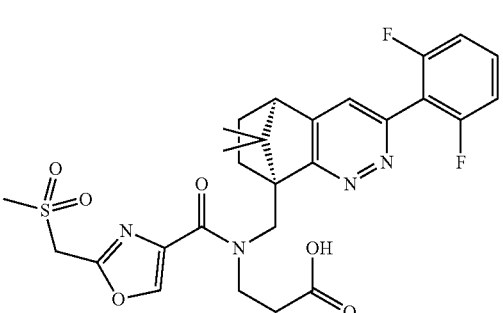 | 3-[[(1S,8R)-5-(2,6-difluorophenyl)-11,11-dimethyl-3,4-diazatricyclo[6.2.1.02,7]undeca-2(7),3,5-trien-1-yl]methyl-[2-(methylsulfonylmethyl)oxazole-4-carbonyl]amino]propanoic acid | |

TABLE 1-continued

| | Structure | Name | IC$_{50}$ |
|---|---|---|---|
| 214 | 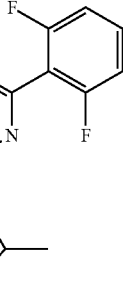 | N-[[(1S,8R)-5-(2,6-difluorophenyl)-11,11-dimethyl-3,4-diazatricyclo[6.2.1.0 2,7]undeca-2(7),3,5-trien-1-yl]methyl]-2-(methylsulfonylmethyl)-N-[2-(5-methyl-4H-1,2,4-triazol-3-yl)ethyl]oxazole-4-carboxamide | |
| 215 | 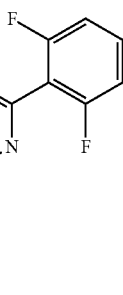 | N-[[(1S,8R)-5-(2,6-difluorophenyl)-11,11-dimethyl-3,4-diazatricyclo[6.2.1.0 2,7]undeca-2(7),3,5-trien-1-yl]methyl]-N-[3-(methylamino)-3-oxo-propyl]-2-(methylsulfonylmethyl)oxazole-4-carboxamide | |
| 216 | 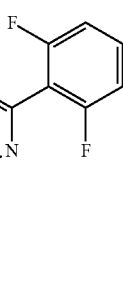 | N-(3-amino-3-oxo-propyl)-N-[[(1S,8R)-5-(2,6-difluorophenyl)-11,11-dimethyl-3,4-diazatricyclo[6.2.1.0 2,7]undeca-2(7),3,5-trien-1-yl]methyl]-2-(methylsulfonylmethyl)oxazole-4-carboxamide | |
| 217 | 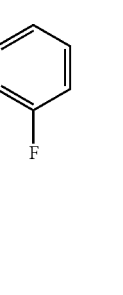 | N-[[(1S,8R)-5-(2,6-difluorophenyl)-11,11-dimethyl-3,4-diazatricyclo[6.2.1.0 2,7]undeca-2(7),3,5-trien-1-yl]methyl]-N-ethyl-3-methyl-1,2,4-oxadiazole-5-carboxamide | |
| 218 | 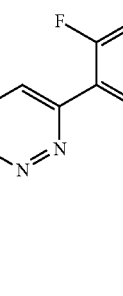 | N-[[(1S,8R)-5-(2,6-difluorophenyl)-11,11-dimethyl-3,4-diazatricyclo[6.2.1.0 2,7]undeca-2(7),3,5-trien-1-yl]methyl]-N-ethyl-2-(2-methylsulfonylethyl)triazole-4-carboxamide | |

TABLE 1-continued

| | Structure | Name | IC₅₀ |
|---|---|---|---|
| 219 | | N-[[(1S,8R)-5-(2,6-difluorophenyl)-11,11-dimethyl-3,4-diazatricyclo[6.2.1.02,7]undeca-2(7),3,5-trien-1-yl]methyl]-N-ethyl-1-(2-methylsulfonylethyl)triazole-4-carboxamide | |
| 220 | | N-[[(1S,8R)-5-(2,6-difluorophenyl)-11,11-dimethyl-3,4-diazatricyclo[6.2.1.02,7]undeca-2(7),3,5-trien-1-yl]methyl]-N-ethyl-5-methyl-1,2,4-oxadiazole-3-carboxamide | |

Proton NMR data for selected compounds is shown below, with the compound numbers below corresponding to the numbering in Table 1:

Compound 1: ¹H NMR (400 MHz, CDCl3) 7.42-7.35 (2H, m), 7.03 (2H, dd, J=8.0, 8.0 Hz), 6.56 (1H, s), 4.47 (1H, d, J=14.3 Hz), 4.21-3.91 (3H, m), 2.97 (1H, d, J=4.0 Hz), 2.36-2.34 (6H, m), 1.37-1.23 (7H, m), 0.70 (3H, s).

Compound 2: ¹H NMR (300 MHz, CDCl3) δ 7.30-7.45 (m, 7H), 7.00-7.09 (m, 2H), 6.18 (br. s. 1H), 5.17 (s, 2H), 3.35-3.50 (m, 1H), 2.95 (d, J=4.5 Hz, 1H), 2.34-2.47 (m, 1H), 1.59 (s, 3H), 1.30-1.57 (m, 2H), 0.65 (s, 3H).

Compound 9: ¹H NMR (400 MHz, CDCl3) δ 8.01 (s, 1H), 7.42-7.32 (m, 2H), 7.03 (dd, J=8.0, 8.0 Hz, 2H), 4.54-4.46 (m, 2H), 4.20-4.09 (m, 1H), 3.90 (d, J=14.3 Hz, 1H), 2.94 (d, J=4.1 Hz, 1H), 2.47 (s, 3H), 2.42-2.18 (m, 2H), 1.55 (s, 3H), 1.32-1.26 (m, 6H), 0.70 (s, 2H).

Compound 28: ¹H NMR (d₆-DMSO, 400 MHz): δ 13.20 (br. s, 1H), 7.69 (s, 1H), 7.63-7.60 (m, 1H), 7.60 (d, J=9.8 Hz, 1H), 7.32-7.24 (m, 2H), 6.97 (d, J=9.8 Hz, 1H), 4.36 (d, J=14.4 Hz, 1H), 3.98 (d, J=14.1 Hz, 1H), 3.37 (s, 3H), 3.07 (d, J=3.2 Hz, 1H), 2.31-2.19 (m, 2H), 1.39-1.27 (m, 1H), 1.21-1.10 (m, 1H), 1.16 (s, 3H), 0.64 (s, 3H).

Compound 29: ¹H NMR (CDCl₃, 400 MHz): δ 8.70 (dd, J=7.0, 1.5 Hz, 1H), 8.59 (d, J=2.3 Hz, 1H), 8.36 (s, 1H), 7.45-7.37 (m, 1H), 7.37 (s, 1H), 7.09-7.01 (m, 2H), 6.90 (dd, J=7.0, 4.1 Hz, 1H), 4.69 (d, J=14.3 Hz, 1H), 4.21-4.10 (m, 1H), 4.10-4.01 (m, 1H), 3.97 (d, J=14.3 Hz, 1H), 2.98 (d, J=3.7 Hz, 1H), 2.61-2.45 (m, 1H), 2.37-2.22 (m, 1H), 1.56-1.46 (m, 1H), 1.31 (s, 3H), 1.29-1.21 (m, 1H), 1.22 (t, J=6.8 Hz, 3H), 0.75 (s, 3H).

Compound 38: ¹H NMR (400 MHz, DMSO) δ 11.33-11.30 (m, 1H), 8.52 (s, 1H), 8.20 (s, 1H), 7.67 (s, 1H), 7.64-7.54 (m, 1H), 7.26 (dd, J=8.1, 8.1 Hz, 2H), 4.33 (d, J=14.4 Hz, 1H), 3.92 (d, J=14.4 Hz, 1H), 3.85-3.69 (m, 2H), 3.28 (s, 3H), 3.05 (d, J=3.5 Hz, 1H), 2.31-2.17 (m, 2H), 1.32-1.20 (m, 6H), 1.18-1.12 (m, 6H), 0.62 (s, 3H).

Compound 39: ¹H NMR (400 MHz, DMSO) δ 8.17 (1H, s), 7.79 (1H, s), 7.66-7.53 (2H, m), 7.26 (2H, dd, J=8.1, 8.1 Hz), 6.83 (2H, s), 4.32 (1H, d, J=14.5 Hz), 3.97-3.77 (3H, m), 3.05-3.00 (1H, m), 2.31-2.20 (2H, m), 1.29-1.22 (2H, m), 1.18-1.09 (6H, m), 0.60 (3H, s).

Compound 41: ¹H NMR (d₆-DMSO, 400 MHz): δ 13.21 (br. s, 1H), 7.72 (s, 1H), 7.65-7.59 (m, 1H), 7.59 (d, J=9.8 Hz, 1H), 7.34-7.25 (m, 2H), 6.98 (d, J=9.9 Hz, 1H), 6.36 (tt, J=55.3, 3.2 Hz, 1H), 4.82-4.65 (m, 1H), 4.65-4.50 (m, 1H), 4.47 (d, J=14.8 Hz, 1H), 4.31 (d, J=2.2 Hz, 1H), 3.98 (d, J=14.6 Hz, 1H), 3.11-3.07 (m, 1H), 2.25 (d, J=9.5 Hz, 1H), 1.33-1.25 (m, 1H), 1.17 (s, 3H), 1.16-1.10 (m, 1H), 0.61 (s, 3H).

Compound 49: ¹H NMR (CDCl₃, 400 MHz): δ 7.45-7.36 (m, 1H), 7.39 (s, 1H), 7.07-7.00 (m, 2H), 5.14 (d, J=7.0 Hz, 1H), 5.00 (d, J=7.0 Hz, 1H), 4.78 (d, J=7.0 Hz, 1H), 4.72 (d, J=7.0 Hz, 1H), 4.20-3.99 (m, 2H), 3.96-3.83 (m, 1H), 3.74-3.60 (m, 1H), 3.49 (s, 1H), 3.00 (d, J=3.0 Hz, 1H), 2.36-2.21 (m, 2H), 1.56-1.45 (m, 1H), 1.39 (t, J=6.7 Hz, 3H), 1.29-1.21 (m, 1H), 1.22 (s, 3H), 0.75 (s, 3H).

Compound 112: ¹H NMR (d₆-DMSO, 400 MHz): δ 7.70 (s, 1H), 7.65-7.56 (m, 1H), 7.33-7.25 (m, 2H), 6.61 (s, 1H), 5.74 (t, J=5.9 Hz, 1H), 4.62 (d, J=5.6 Hz, 2H), 4.33 (d, J=14.4 Hz, 1H), 3.94 (d, J=14.4 Hz, 1H), 3.95-3.82 (m, 1H), 3.81-3.68 (m, 1H), 3.07 (d, J=3.2 Hz, 1H), 2.26 (d, J=8.8 Hz, 1H), 2.26-2.10 (m, 1H), 1.33-1.24 (m, 1H), 1.22 (t, J=6.9 Hz, 3H), 1.19 (s, 3H), 1.18-1.11 (m, 1H), 0.63 (s, 3H).

Compound 114: ¹H NMR (d₆-DMSO, 400 MHz): δ 14.28 (br. s, 1H), 7.69 (s, 1H), 7.65-7.56 (m, 1H), 7.33-7.25 (m, 2H), 5.62 br. (s, 1H), 4.59 (d, J=4.3 Hz, 2H), 4.34 (d, J=14.4 Hz, 1H), 4.08-3.98 (m, 1H), 3.93 (d, J=14.4 Hz, 1H), 3.90-3.78 (m, 1H), 3.09-3.06 (m, 1H), 2.26 (d, J=8.8 Hz, 1H), 2.20-2.08 (m, 1H), 1.30-1.17 (m, 4H), 1.19 (s, 3H), 1.17-1.11 (m, 1H), 0.64 (s, 3H).

Compound 121: ¹H NMR (400 MHz, DMSO-d₆) δ 7.67 (t, J=1.1 Hz, 1H), 7.65-7.56 (m, 1H), 7.50-7.42 (m, 1H), 7.36-7.20 (m, 5H), 4.65-4.53 (m, 2H), 3.67-3.51 (m, 4H), 3.05 (d, J=4.0 Hz, 1H), 2.38-2.21 (m, 2H), 1.20 (t, J=7.0 Hz, 5H), 1.08 (s, 3H), 0.49 (s, 3H).

Compound 124: $^1$H NMR (400 MHz, DMSO-d$_6$) δ 7.97-7.90 (m, 1H), 7.81-7.73 (m, 1H), 7.69 (q, J=1.4 Hz, 1H), 7.65-7.42 (m, 3H), 7.34-7.24 (m, 2H), 4.02-3.81 (m, 2H), 3.81-3.56 (m, 3H), 3.12-3.07 (m, 1H), 2.40-2.22 (m, 2H), 1.36-1.27 (m, 1H), 1.17 (d, J=16.0 Hz, 4H), 1.08-0.94 (m, 3H), 0.60 (d, J=5.2 Hz, 3H).

Compound 145: $^1$H NMR (400 MHz, DMSO-d$_6$) δ 8.61 (d, J=6.0 Hz, 2H), 7.68 (s, 1H), 7.61 (t, J=8.5 Hz, 1H), 7.51 (d, J=6.0 Hz, 2H), 7.36-7.20 (m, 2H), 4.63 (d, J=11.6 Hz, 2H), 3.76-3.50 (m, 4H), 3.06 (d, J=4.0 Hz, 1H), 2.45-2.10 (m, 3H), 1.22 (t, J=7.0 Hz, 4H), 1.17-1.09 (m, 1H), 1.09 (s, 2H), 0.51 (s, 3H).

Compound 154: $^1$H NMR (d$_6$-DMSO, 400 MHz): δ 12.32 (br. s, 1H), 7.89 (s, 1H), 7.67 (s, 1H), 7.65-7.56 (m, 1H), 7.38-7.25 (m, 2H), 7.24 (br. s, 1H), 4.18 (d, J=14.3 Hz, 1H), 3.90-3.86 (m, 1H), 3.80 (d, J=16.2 Hz, 1H), 3.71 (d, J=14.4 Hz, 1H), 3.66 (d, J=16.2 Hz, 1H), 3.63-3.55 (m, 1H), 3.04 (d, J=3.4 Hz, 1H), 2.26-2.13 (m, 2H), 1.30 (t, J=7.0 Hz, 3H), 1.26-1.12 (m, 2H), 1.10 (s, 3H), 0.56 (s, 3H).

Compound 162: $^1$H NMR (d$_6$-DMSO, 400 MHz): δ 11.17 (br. s, 2H), 7.68 (s, 1H), 7.65-7.56 (m, 1H), 7.34-7.24 (m, 2H), 4.18 (d, J=14.4 Hz, 1H), 3.94-3.83 (m, 1H), 3.79-3.63 (m, 3H), 3.56 (d, J=16.6 Hz, 1H), 3.05 (d, J=3.4 Hz, 1H), 2.24-2.15 (m, 2H), 1.27 (t, J=7.0 Hz, 3H), 1.21-1.12 (m, 2H), 1.11 (s, 3H), 0.57 (s, 3H).

Compound 163: $^1$H NMR (d$_6$-DMSO, 400 MHz): δ 12.82 (br. s, 1H), 7.67 (s, 1H), 7.63-7.56 (m, 1H), 7.33 (d, J=9.7 Hz, 1H), 7.32-7.25 (m, 2H), 6.82 (d, J=9.7 Hz, 1H), 4.19 (d, J=14.5 Hz, 1H), 3.98-3.86 (m, 1H), 3.83 (d, J=16.1 Hz, 1H), 3.83-3.75 (m, 1H), 3.74 (s, 1H), 3.70 (d, J=1.3 Hz, 1H), 3.07 (d, J=3.8 Hz, 1H), 2.25-2.13 (m, 2H), 1.28 (t, J=7.0 Hz, 3H), 1.22-1.11 (m, 2H), 1.09 (s, 3H), 0.56 (s, 3H).

Compound 164: $^1$H NMR (d$_6$-DMSO, 400 MHz,): δ 8.34 (s, 0.6H), 8.31 (s, 0.4H), 7.72 (s, 1H), 7.65-6.57 (m, 1H), 7.49 (s, 0.6H), 7.46 (s, 0.4H), 7.33-7.27 (m, 2H), 5.42-5.38 (m, 0.4H), 5.00-4.95 (m, 0.6H), 4.39-4.19 (m, 1.4H), 3.90-3.85 (m, 0.6H), 3.05-3.04 (d, J=3.6 Hz, 0.4H), 3.01-3.00 (d, J=4.0 Hz, 0.6H), 2.18-2.15 (m, 1.4H), 2.01-1.98 (m, 0.6H), 1.72-1.70 (d, J=6.8 Hz, 1.8H), 1.68-1.66 (d, J=7.2 Hz, 1.2H), 1.29 (t, J=7.2 Hz, 1.8H), 1.18 (s, 1.2H), 1.13 (t, J=6.8 Hz, 1.2H), 1.31-1.03 (m, 2H), 0.77 (s, 1.8H), 0.70 (s, 1.2H), 0.58 (s, 1.8H).

Compound 181: $^1$H NMR (d$_6$-DMSO, 400 MHz,): δ 8.80 (d, J=15.9 Hz, 1H), 7.71 (s, 1H), 7.61 (ddd, J=15.0, 8.5, 6.6 Hz, 1H), 7.30 (t, J=8.1 Hz, 2H), 6.44 (t, J=55.7 Hz, 1H), 5.00 (d, J=16.1 Hz, 3H), 4.79 (dd, J=24.4, 14.9 Hz, 1H), 4.65-3.76 (m, 2H), 3.19-3.01 (m, 4H), 2.31-1.93 (m, 2H), 1.27 (q, J=8.4, 7.4 Hz, 1H), 1.15 (d, J=18.6 Hz, 3H), 0.84 (s, 1H), 0.55 (d, J=50.0 Hz, 3H).

Compound 182: $^1$H NMR (d$_6$-DMSO, 400 MHz,): δ 8.62 (s, 1H), 7.67 (s, 1H), 7.66-7.54 (m, 1H), 7.29 (t, J=8.1 Hz, 2H), 4.97 (s, 2H), 4.65 (s, 1H), 4.17 (s, 1H), 4.07 (d, J=15.0 Hz, 1H), 3.16 (s, 3H), 3.01 (s, 1H), 2.22 (d, J=9.0 Hz, 2H), 1.44 (d, J=6.7 Hz, 4H), 1.33 (s, 3H), 1.17 (d, J=6.9 Hz, 3H), 0.82 (s, 1H), 0.61 (s, 2H), 0.44 (s, 1H).

Compound 183: $^1$H NMR (d$_6$-DMSO, 400 MHz,): δ 8.67 (s, 1H), 7.69 (s, 1H), 7.65-7.55 (m, 1H), 7.29 (t, J=8.1 Hz, 2H), 4.97 (s, 2H), 4.44 (d, J=14.4 Hz, 1H), 4.21 (dd, J=14.7, 6.4 Hz, 1H), 4.07 (d, J=14.4 Hz, 1H), 3.83 (dd, J=14.9, 7.2 Hz, 1H), 3.16 (s, 3H), 3.06 (s, 1H), 2.30-2.13 (m, 2H), 1.26-1.07 (m, 5H), 0.84-0.08 (m, 8H).

Compound 184: $^1$H NMR (d$_6$-DMSO, 400 MHz, 27/28 H): δ 8.67 (s, 1H), 7.66 (d, J=11.3 Hz, 1H), 7.64-7.53 (m, 1H), 7.29 (t, J=8.1 Hz, 2H), 4.95 (s, 2H), 4.23 (s, 2H), 3.15 (s, 3H), 3.07-3.00 (m, 1H), 2.42 (d, J=10.6 Hz, 1H), 2.29 (d, J=25.8 Hz, 1H), 1.40 (td, J=9.0, 4.5 Hz, 1H), 1.15 (s, 4H), 0.89-0.57 (m, 7H).

Example 5 In Vitro RORc Ligand Binding Assay

This assay was used to determine a compound's potency in inhibiting activity of RORc by determining, Ki$_{app}$, IC$_{50}$, or percent inhibition values. Consumables used in this Example are shown in Table 2 below.

TABLE 2

| Consumable | Supplier and product code |
|---|---|
| GFB Unifilter plates | Perkin Elmer 6005177 |
| 3-[(3-Cholamidopropyl)dimethylammonio]-1-propanesulfonate (CHAPS) | Sigma C5070 |
| 96-well polypropylene U-bottom assay plate | Nunc 267245 |
| HEPES buffer, 1M | Sigma H3375 |
| Magnesium chloride (MgCl$_2$) | Sigma M8266 |
| D,L-Dithiothreitol (DTT) | Sigma D0632 |
| Sodium chloride (NaCl) | Sigma 71382 |
| Bovine serum albumin (BSA) | Sigma A7030 [lyophilized powder, ≥98% (agarose gel electrophoresis), Essentially fatty acid free, essentially globulin free] |
| 25-hydroxycholesterol | Sigma H1015 |
| 25-[26,27-$^3$H]hydroxycholesterol | Perkin Elmer NET674250UC American Radiolabeled Chemicals ART0766 |
| RORc ligand binding domain | Genentech (e.g., PUR 28048), expressed in *E. coli* |
| Plate seals | Perkin Elmer 6005185 |
| Microscint 0 | Perkin Elmer 6013611 |

Table 2

Filter Plate Preparation

On day of the assay, 100 uL of 0.05% CHAPS (in deionized H$_2$O) was added to all wells of the GFB Unifilter plate and allowed soak for 1 h. A wash buffer of 50 mM HEPES (pH 7.4), 150 mM NaCl, and 5 mM MgCl$_2$ was prepared to wash the filter plate. To prepare an assay buffer, BSA was added to the wash buffer to reach 0.01% and DTT was added to reach 1 mM.

Compounds

For IC$_{50}$ mode, 10 mM compound stocks were serially diluted in DMSO with DMSO to give 20× required final concentration in DMSO (15 uL compound+30 uL DMSO). The 20× compound stocks were diluted in DMSO with Assay Buffer 4-fold to reach 5× the final test concentration in 25% DMSO (10 uL compound+30 uL Assay Buffer). Solutions were mixed by aspiration several times with a pipette set on 50 uL volume. For the assay, 10 uL of 5× compound stock solutions in 25% DMSO were added to the assay plate in duplicate.

For two point screening, 10 mM stock compound solutions were diluted in DMSO to obtain 200 uM (20× the high test concentration) and then diluted 10-fold further to reach 20 uM (20× the low test concentration). The 20× stocks were diluted 4-fold with Assay Buffer (10 uL compound+30 uL Assay Buffer) to reach 5× the test concentrations (50 uM and 5 uM) and 10 uL were added to two assay plates for the duplicate wells. With each concentration tested on 2 plates, each set of 80 compounds used 4 assay plates (1 uM and 10 uM, with n=2).

Nonspecific Binding (NSB) Samples, Total Binding (TB) Samples and No Receptor (No R) Samples 25-hydroxycholesterol (1 uM) was used to determine the level of NSB signal is prepared in DMSO as for compounds above, then diluted in Assay Buffer to give a final concentration of 5 uM. For 25-hydroxycholesterol in 25% DMSO/75% Assay Buffer; 10 uL per well was used for NSB samples. Wells for Total Binding and No Receptor sample determination contained 10 uL of 25% DMSO/75% Assay Buffer per well.

Radioligand (25-[$^3$H]hydroxycholesterol) Preparation

25-[$^3$H]hydroxycholesterol was diluted in Assay Buffer to obtain 15 nM and vortex to mix. Add 20 uL to all wells to reach 6 nM final concentration in the assay.

Receptor Preparation

The optimal concentration for RORc receptor was found to be 0.6 ug/mL. Stock receptor solution was diluted in assay buffer to obtain 1.5 ug/mL in Assay Buffer. 20 uL was added to all wells. For No Receptor samples, 20 uL Assay Buffer was substituted for receptor solution.

Sample Addition to Plates and Incubation

Assay plates were 96-well polypropylene V-bottom plates. 10 uL of 5× compound in 25% DMSO/75% Assay Buffer was added to Test wells. 10 uL of 25% DMSO/75% Assay Buffer was added to Total Binding or No Receptor wells. 10 uL of 5 uM 25-hydroxycholesterol in 25% DMSO/75% Assay Buffer was added to NSB wells. 20 uL of 15 nM 25-[$^3$H]hydroxycholesterol prepared in Assay Buffer was added to all wells. 20 uL of 1.5 ug/mL RORc receptor was added to wells (or 40 uL Assay Buffer to No R wells). Following addition to the wells, the plates were incubated 3 h at 25° C.

Filtration

Using a Packard Filtermate Harvester, the filter plate were washed 4 times following transfer of the incubated samples. Plates were dry-filtered completely (2 h at 50° C. or overnight at room temperature). 50 uL Microscint 0 was added to all wells and read on Topcount protocol Inverted.

Final Concentrations

Final concentrations were as follows: 50 mM HEPES buffer (pH 7.4); 150 mM NaCl; 1 mM DTT; 5 mM MgCl$_2$, 0.01% BSA; 5% DMSO; 0.6 ug/mL RORc receptor; 6 nM 25-[$^3$H]hydroxycholesterol. For NSB wells, 1 uM 25-hydroxycholesterol was also present.

Example 4: RORc Coactivator Peptide Binding Assay

Assays were carried out in 16-microL reaction volumes in black 384 Plus F Proxiplates (PerkinElmer 6008269). All assay components except test ligand were mixed in coregulator buffer D (Invitrogen PV4420) containing 5 mM DTT and added to the plate at twice their final concentrations in a volume of 8 microL. Test ligands at 2× the final concentration were then added to the wells in 8 □L of coregulator buffer D containing 5 mM DTT and 4% DMSO. Final incubations contained 1× coregulator buffer D, 5 mM DTT, test ligand, 2% DMSO, 50 nM biotinyl-CPSSHSSLTERKH-KILHRLLQEGSPS (American Peptide Company; Vista, Calif.), 2 nM Europium anti-GST (Cisbio 61GSTKLB), 12.5 nM streptavidin-D2 (Cisbio 610SADAB), 50 mM KF, and 10 nM of bacterially-expressed human RORc ligand binding domain protein containing an N-terminal 6×His-GST-tag and residues 262-507 of Accession NP_005051. Ten test ligand concentrations were tested in duplicate. After the reaction plates were incubated for 3 h in the dark at room temperature (22-23° C.), the plate was read on an EnVision plate reader (PerkinElmer) following the Europium/D2 HTRF protocol (ex 320, em 615 and 665, 100 □s lag time, 100 flashes, 500 μs window). The time-resolved FRET signal at 665 nm was divided by that at 615 nm to generate the signal ratio of each well. The signal ratio of wells containing RORc and peptide but no test ligand were averaged and set to 0% Effect while the signal ratios of the blank wells containing coactivator peptide but no RORc were averaged and set to −100% Effect. RORc exhibits a basal (constitutive) signal in this assay and test ligands can increase or decrease the signal ratio relative to this basal signal level. RORc agonists increase the signal ratio in this assay and result in a positive % Effect value. Inverse agonists decrease the signal ratio, and result in a negative % Effect value. The $EC_{50}$ value is the concentration of test compound that provides half-maximal effect (increased or decreased assay signal) and is calculated by Genedata Screener® software (Genedata; Basel, Switzerland) using the following equation:

$$\% \text{ Effect} = S_0 + \{(S_{inf} - S_0)/[1+(10^{\log EC_{50}}/10^c)^n]\}$$

where $S_0$ equals the activity level at zero concentration of test compound, $S_{inf}$ is the activity level at infinite concentration of test compound, $EC_{50}$ is the concentration at which the activity reaches 50% of the maximal effect, c is the concentration in logarithmic units corresponding to the values on the x-axis of the dose-response curve plot, and n is the Hill coefficient (the slope of the curve at the $EC_{50}$).

Example 6: Arthritis Mouse Model 8 to 10-week old male DBA/1 (DBA/1OlaHsd, Harlan Laboratories) mice are housed in a specific pathogen free (SPF) animal facility. Arthritis is induced by two injections of collagen subcutaneously in the base of the tail. The initial injection (on day 0) uses bovine type II collagen (2 mg/ml from Chondrex, Redmond, Wash.) emulsified in equal volume of CFA containing 4 mg/ml of M. tuberculosis (Chondrex). The CII booster injection on Day 29 is emulsified in incomplete Freund's adjuvant (IFA). Each animal receives 0.1 ml of emulsion by subcutaneous/intradermal injection in the tail 2 to 3 cm from the body of the mouse. The booster injection site is in the vicinity of but different from the initial injection site and closer to the body of the animal. OR-1050 was formulated in HRC-6 as above. On weekdays, the animals receive two doses (a.m. and p.m.) of HRC-6 or 50 mg/kg OR-1050 p.o. (2.5 mls/kg). On weekends, a single dose of 100 mg/kg is administered (5 mls/kg).

The mice are observed daily for clinical symptoms of CIA based on the following qualitative scale. Each paw was examined individually and scored. Grade 0, normal; grade 1, mild but definite redness and swelling of the ankle or wrist, or apparent redness and swelling limited to individual digits, regardless of the number of affected digits; grade 2, moderate redness and swelling of ankle or wrist; grade 3, severe redness and swelling of the entire paw including digits; grade 4, maximally inflamed limb with involvement of multiple joints. To estimate cumulative disease severity for each animal, an area under the curve score is calculated for each animal by totaling the sum of the daily hind paw measurements betweens days 24 and 48.

Example 7: Muscular Sclerosis Mouse Model I

Experiments are conducted on female mice aged 4-6 weeks belong to the C57BL/6 strain weighing 17-20 g. Experimental autoimmune encephalomyelitis (EAE) is actively induced using 95% pure synthetic myelin oligodendrocyte glycoprotein peptide 35-55 ($MOG_{35-55}$) (Invitrogen). Each mouse is anesthetized and receives 200 ug of $MOG_{35-55}$ peptide and 15 ug of Saponin extract from Quilija bark emulsified in 100 uL of phosphate-buffered saline. A 25 uL volume is injected subcutaneously over four flank areas. Mice are also intraperitoneally injected with 200 ng of pertussis toxin in 200 uL of PBS. A second, identical injection of pertussis toxin is given after 48 h.

A compound of the invention is administered at selected doses. Control animals receive 25 uL of DMSO. Daily treatment extends from day 26 to day 36 post-immunization. Clinical scores are obtained daily from day 0 post-immunization until day 60. Clinical signs are scored using the following protocol: 0, no detectable signs; 0.5, distal tail limpness, hunched appearance and quiet demeanor; 1, completely limp tail; 1.5, limp tail and hindlimb weakness (unsteady gait and poor grip with hind limbs); 2, unilateral partial hind limb paralysis; 2.5, bilateral hind limb paralysis; 3, complete bilateral hindlimb paralysis; 3.5, complete hindlimb paralysis and unilateral forelimb paralysis; 4, total paralysis of hind limbs and forelimbs (Eugster et al., Eur J Immunol 2001, 31, 2302-2312).

Inflammation and demyelination may be assessed by histology on sections from the CNS of EAE mice. Mice are sacrificed after 30 or 60 days and whole spinal cords are removed and placed in 0.32 M sucrose solution at 4° C. overnight. Tissues are prepared and sectioned. Luxol fast blue stain is used to observe areas of demyelination. Haematoxylin and eosin staining is used to highlight areas of inflammation by darkly staining the nuclei of mononuclear cells. Immune cells stained with H&E are counted in a blinded manner under a light microscope. Sections are separated into gray and white matter and each sector is counted manually before being combined to give a total for the section. T cells are immunolabeled with anti-CD3+ monoclonal antibody. After washing, sections are incubated with goat anti-rat HRP secondary antibody. Sections are then washed and counterstained with methyl green. Splenocytes isolated from mice at 30 and 60 days post-immunization are treated with lysis buffer to remove red blood cells. Cells are then re-suspended in PBS and counted. Cells at a density of about $3 \times 10^6$ cells/mL are incubated overnight with 20 ug/mL of MOG peptide. Supernatants from stimulated cells are assayed for IFNgamma protein levels using an appropriate mouse IFN-gamma immunoassay system.

Example 8: Muscular Sclerosis Mouse Model II

In this model, female rodents are anesthetized with isoflurane and injected with Freund's Incomplete Adjuvant containing 1 mg/mL neuronal antigen (e.g. myelin basic protein, myelin oligodendrocyte glycoprotein, proteolipid protein) and 4 mg/mL mycobacterium tuberculosis at two sites on the back on day 0 of this study. A compound of interest is then dosed daily in a sub-cutaneous, intraperitoneally, or oral manner from day 0 until the end of study at an efficacious dose. Daily observations of degree of paralysis are taken as measures of efficacy.

Example 9: Psoriasis Mouse Model I

The severe, combined immunodeficient (SCID) mouse model can be used to evaluate the efficacy of compounds for treating psoriasis in humans (Boehncke, Ernst Schering Res Found Workshop 2005, 50, 213-34; and Bhagavathula et al., J Pharmacol Expt'l Therapeutics 2008, 324(3), 938-947). Briefly, SCID mice are used as tissue recipients. One biopsy for each normal or psoriatic volunteer (human) is transplanted onto the dorsal surface of a recipient mouse. Treatment is initiated 1 to 2 weeks after transplantation. Animals with the human skin transplants are divided into treatment groups. Animals are treated twice daily for 14 days. At the end of treatment, animals are photographed and then euthanized. The transplanted human tissue along with the surrounding mouse skin is surgically removed and fixed in 10% formalin and samples obtained for microscopy. Epidermal thickness is measured. Tissue sections are stained with an antibody to the proliferation-associated antigen Ki-67 and with an anti-human CD3.sup.+ monoclonal antibody to detect human T lymphocytes in the transplanted tissue. Sections are also probed with antibodies to c-myc and beta-catenin. A positive response to treatment is reflected by a reduction in the average epiderma thickness of the psoriatic skin transplants. A positive response is also associated with reduced expression of Ki-67 in keratinocytes.

Example 10: Psoriasis Mouse Model II

Using the Imidquimod model of skin inflammation (Fits et al, Journal of Immunology, 2009, 182: 5836-5845), 10-12 week old BALB/c, Il17c+/+ or Il17c−/−, or Il17re+/+ or Il17re−/− mice were administered 50 mg Aldara cream (5% Imidquimod in Graceway, 3M) in the shaved back and right ear daily for 5 days. Clinical scoring and ear thickness measurements were performed daily. Scoring was based upon the manifestation of psoriatic symptoms, such as erythema, scaling and thickness: 0, No disease. 1, Very mild erythema with very mild thickening and scaling involving a small area. 2, Mild erythema with mild thickening and scaling involving a small area. 3, Moderate erythema with moderate thickening and scaling (irregular and patchy) involving a small area (<25%). 4, Severe erythema with marked thickening and scaling (irregular and patchy) involving a moderate area (25-50%). 5, Severe erythema with marked thickening and scaling (irregular and patchy) involving a large area (>50%). Ear and back tissue were harvested on day 5 for histological evaluation. Efficacy of compounds is compared in the imiquimod (IMQ) mouse model of psoriasis. Balb/c mice (10 males/group) received daily topical IMQ (5% cream) on shaved back and right ear for 5 days as described above. Animals received oral dose of a representative compound or DMF (45 or 90 mg-eq MMF/kg twice daily) or vehicle from Day −5 to Day +5. Erythema score is the primary outcome measure.

Example 11: Irritable Bowel Disease Mouse Model I

Effectiveness in treatment of inflammatory bowel disease may be evaluated as described by Jurjus et al., J Pharmaocol Toxicol Methods 2004, 50, 81-92; Villegas et al., Int'l Immunopharmacol 2003, 3, 1731-1741; and Murakami et al., Biochemical Pharmacol 2003, 66, 1253-1261. Briefly, female ICR mice are divided into treatment groups which are given either water (control), 5% DSS in tap water is given at the beginning of the experiment to induce colitis, or various concentrations of test compound. After administering test compound for 1 week, 5% DSS in tap water is also administered to the groups receiving test compound for 1 week. At the end of the experiment, all mice are sacrificed and the large intestine is removed. Colonic mucosa samples are obtained and homogenized. Proinflammatory mediators (e.g., IL-1alpha, IL-1beta, TNFalpha, PGE2, and PGF2alpha.) and protein concentrations are quantified. Each excised large intestine is histologically examined and the damage to the colon scored.

Example 12: Chronic Obstructive Pulmonary Disease Mouse Model

The cigarette smoke model of Martorana et al., Am J Respir Crit Care Med 2005, 172, 848-835; and Cavarra et al., Am J Respir Crit Care Med 2001, 164, 886-890 can be used for assessing efficacy in treating emphysema. Briefly, six-week old C57B1/6J male mice are exposed either to room air or to the smoke of five cigarettes for 20 minutes. For the acute study, mice are divided into three groups of 40 animals each. These groups are then divided into four subgroups of 10 mice each as follows: (1) no treatment/air-exposed; (2) no treatment/smoke-exposed; (3) a first dose of test compound plus smoke-exposed; and (4) a second dose of test compound. In the first group, trolox equivalent antioxidant capacity is assessed at the end of the exposure in bronchoalveolar lavage fluid. In the second group, cytokines and chemokines are determined in bronchoalveolar lavage fluid using a commercial cytokine panel at 4 hours; and in the third group bronchoalveolar lavage fluid cell count is assessed at 24 hours.

In a chronic study, the mice are exposed to either room air or to the smoke of three cigarettes/day, for 5 days/week, for 7 months. Five groups of animals are used: (1) no treatment/ air-exposed; (2) a first dose of a test compound plus air-exposed; (3) no treatment/smoke-exposed; (4) a second dose of the test compound plus smoke-exposed; and (5) the first dose of the test compound plus smoke exposed. Seven months after chronic exposure to room air or cigarette smoke, 5 to 12 animals from each group are sacrificed and the lungs fixed intratracheally with formalin. Lung volume is measured by water displacement. Lungs are stained. Assessment of emphysema includes mean linear intercept and internal surface area. The volume density of macrophages, marked immunohistochemically with anti-mouse Mac-3 monoclonal antibodies is determined by point counting. A mouse is considered to have goblet cell metaplasia when at least one or more midsize bronchi/lung showed a positive periodic acid-Schiff staining for the determination of desmosine, fresh lungs are homogenized, processed, and analyzed by high-pressure liquid chromatography.

Example 13: Asthma Mouse Model

A single inhaled allergen challenge can induce an acute increase in airway responsiveness in some individuals and animal models. However, repeated allergen inhalations have demonstrated more pronounced, consistent, and prolonged increases in airway responsiveness. This mouse model of long-term repeated inhalations of allergen has been used to study the long term effect of allergic diseases in the lung, and to delineate the cells, mechanisms, molecules, and mediators involved in the induction of airway hyperresponsiveness of lung in humans.

Crystalline OVA is obtained from Pierce Chem. Co. (Rockford, Ill.) aluminum potassium sulfate (alum) from Sigma Chem. Co. (St. Louis, Mo.), pyrogen-free distilled water from Baxter, Healthcare Corporation (Deerfield, Ill.), 0.9% sodium chloride (normal saline) from Lymphomed (Deerfield, Ill.) and Trappsol™. HPB-L100 (aqueous hydroxypropylbeta cyclodextrin; 45 wt/vol % aqueous solution) from Cyclodextrin Technologies Development, Inc. (Gainesville, Fla.). The OVA (500 ug/ml in normal saline) is mixed with equal volumes of 10% (wt/vol) alum in distilled water. The mixture (pH 6.5 using 10 N NaOH) after incubation for 60 minutes at room temperature is centrifuged at 750 g for 5 minutes; the pellet resuspended to the original volume in distilled water and used within one hour. The selective 5-lipoxtgenase inhibitor, Zileuton (N-[1-benzo[b] thien-2-ylethyl]-N-hydroxyurea; J. Pharmacol Exp Ther. 1991; 256: 929-937) is dissolved in Trappsol™. Histatek, Inc. (Seattle, Wash.) to provide the mast cell degranulation inhibitor, f-Met-Leu-Phe-Phe ("HK-X").

Female BALB/c Once (6-8 wk of age) receive an i.p. injection of 0.2 ml (100 ug) of OVA with alum (J. Exp Med. 1996; 184: 1483-1494). Mice are anesthetized with 0.2 ml i.p. of ketamine (0.44 mg/ml)/xylazine (6.3 mg/ml) in normal saline before receiving an intranasal (i.n.) dose of 100 ug OVA in 0.05 ml normal saline and an i.n. dose of 50 ug OVA in 0.05 ml normal saline separately on different days. Two control groups are used: the first group receives normal saline with alum i.p. and normal saline without alum i.n.; and the second group receives OVA with alum i.p., OVA without alum i.n., and normal saline, alone.

The trachea and left lung (the right lung may be used for bronchoalveolar lavage ("BAL") as described below) are obtained and fixed in 10% neutral formaldehyde solution at room temperature for about 15 h. After being embedded in paraffin, the tissues are cut into 5-um sections and processed with the different staining or immunolabling further. Discombe's eosinophil staining is used for counting the cell numbers with the counterstain of methylene blue. The eosinophil number per unit airway area (2,200 $um^2$) is determined by morphometry (J. Pathol. 1992; 166: 395-404; Am Rev Respir Dis. 1993; 147:448-456). Fibrosis is identified with the Masson's trichrome staining. Airway mucus iss identified by the following staining method: methylene blue, hematoxylin and eosin, mucicarmine, alcian blue, and alcian blue/periodic acid-Schiff (PAS) reaction (Troyer, H., "Carbohydrates" in Principles and Techniques of Histochemistry, Little, Brown and Company, Boston, Mass., 1980: 89-121; Sheehan, D. C., et al., "Carbohydrates" in Theory and Practice of Histotechnology, Battle Press, Columbus, Ohio, 1980: 159-179) Mucin is stained with mucicarmine solution; metanil yellow counterstain is employed. Acidic mucin and sulfated mucosubstances are stained with alcian blue, pH 2.5; nuclear fast red counterstain is used. Neutral and acidic mucosubstances are identified by alcian blue, pH 2.5, and PAS reaction. The degree of mucus plugging of the airways (0.5-0.8 mm in diameter) is also assessed by morphometry. The percent occlusion of airway diameter by mucus iss classified on a semiquantitative scale from 0 to 4+. The histologic and morphometric analyses may be performed by individuals blinded to the protocol design.

On day 28, 24 hours after the last i.n. administration of either normal saline or OVA, pulmonary mechanics to intravenous infusion of methacholine may be determined in mice in vivo by a plethysmographic method as previously described (10, 1958; 192: 364-368; J. Appl. Physiol. 1988; 64: 2318-2323; J. Exp. Med. 1996; 184: 1483-1494).

After tying off the left lung at the mainstem bronchus, the right lung may be lavaged three times with 0.4 ml of normal saline. Bronchoalveolar lavage (BAL) fluid cells from a 0.05-ml aliquot of the pooled sample are counted using a hemocytometer and the remaining fluid centrifuged at 4° C. for 10 minutes at 200 g. The supernatant may be stored at 70.degree. C. until eicosanoid analysis is performed. After resuspension of the cell pellet in normal saline containing 10% bovine serum albumin ("BSA"), BAL cell smears are made on glass slides. To stain eosinophils, dried slides are stained with Discombe's diluting fluid (0.05% aqueous eosin and 5% acetone (vol/vol) in distilled water; J. Exp. Med. 1970; 131: 1271-1287) for 5-8 minutes, rinsed with water for 0.5 minutes, and counterstained with 0.07% methylene blue for 2 minutes.

While the present invention has been described with reference to the specific embodiments thereof, it should be

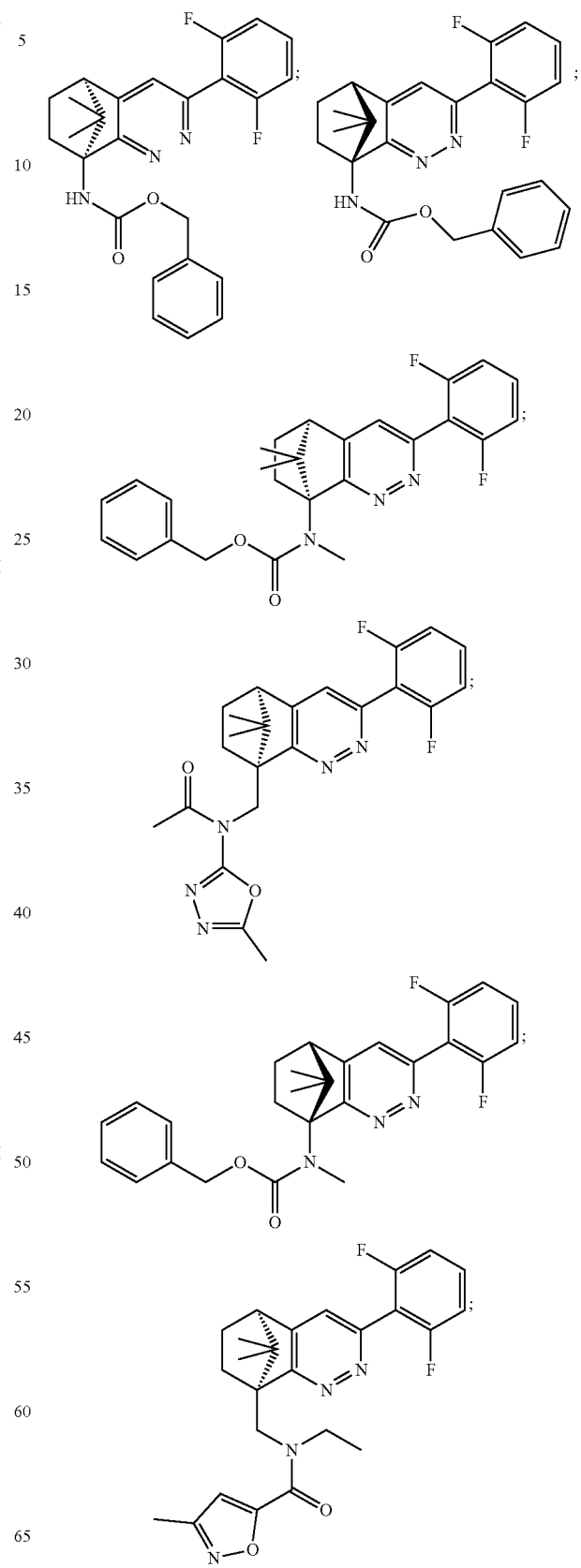

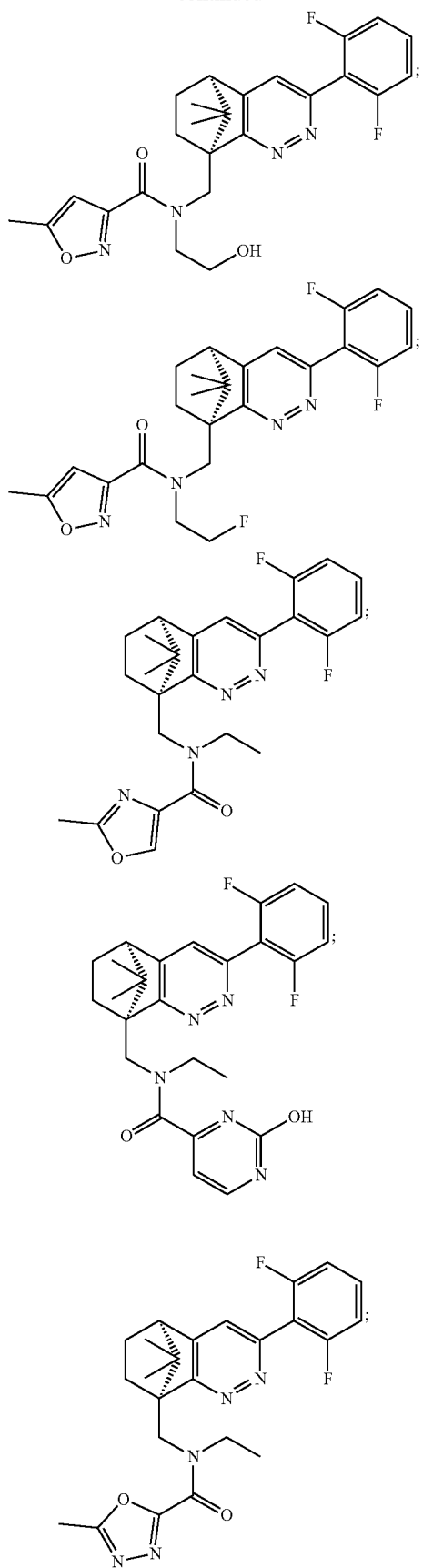
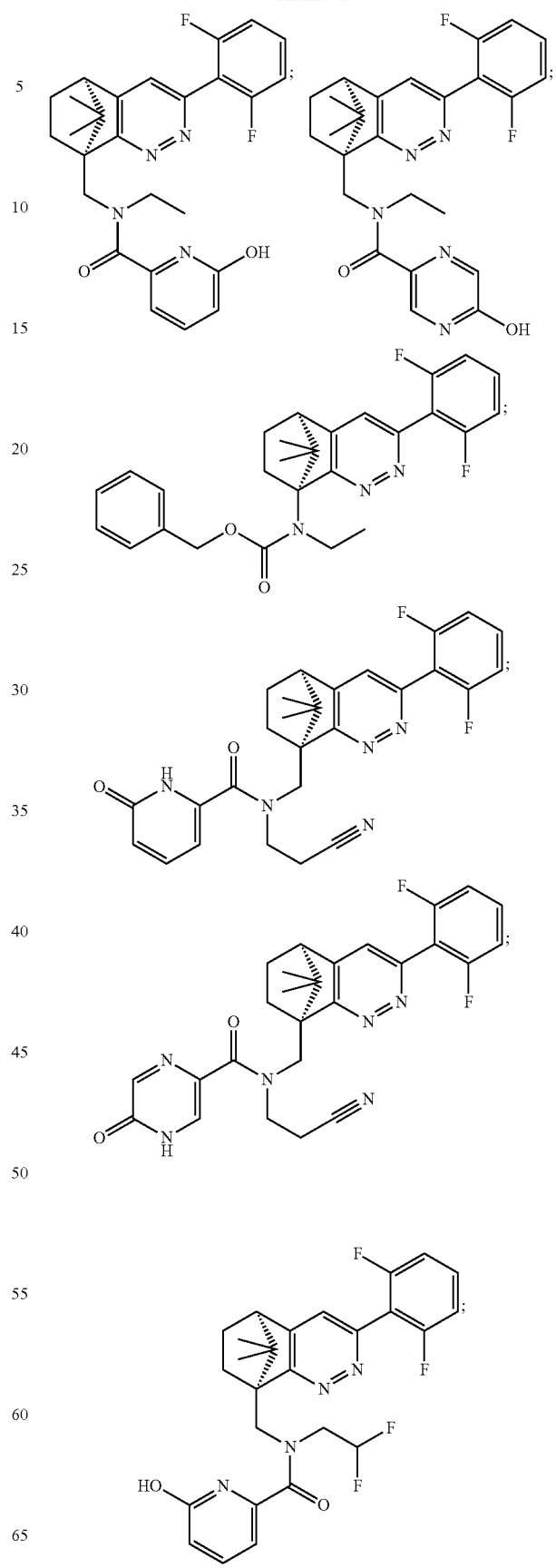

141
-continued
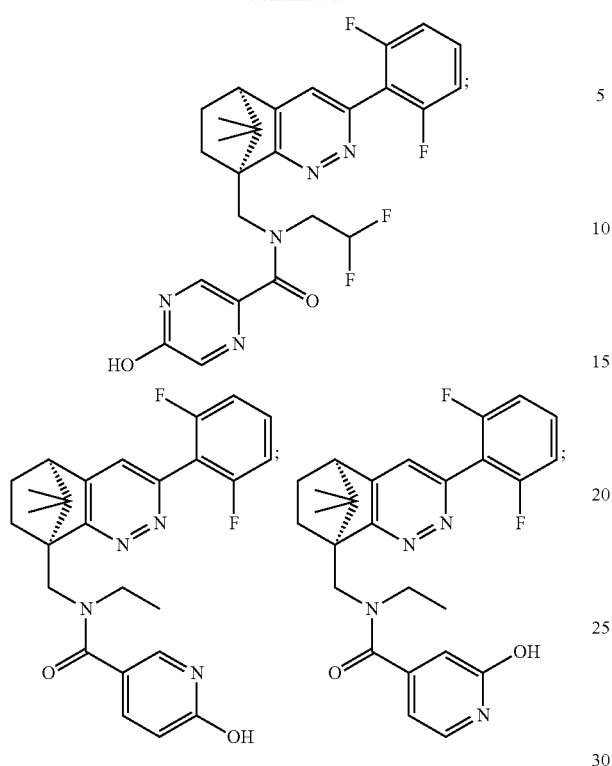
142
-continued
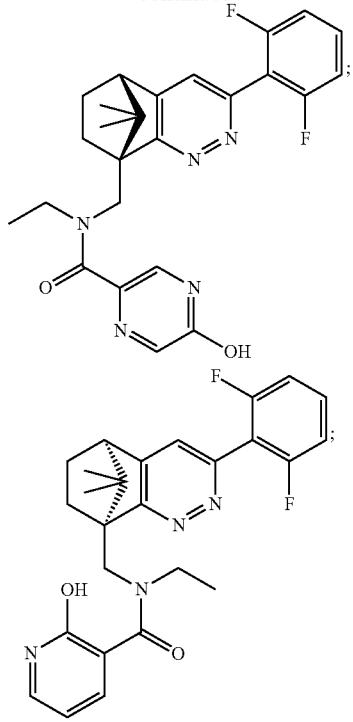
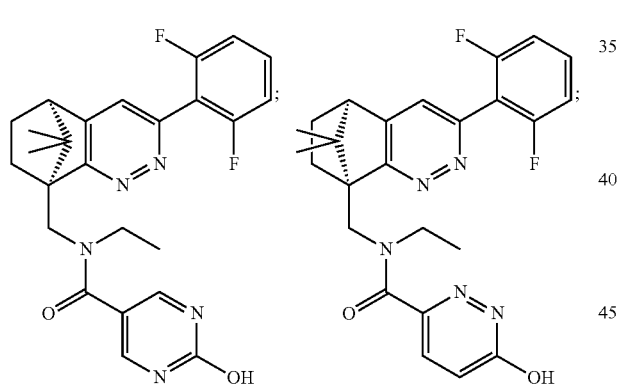
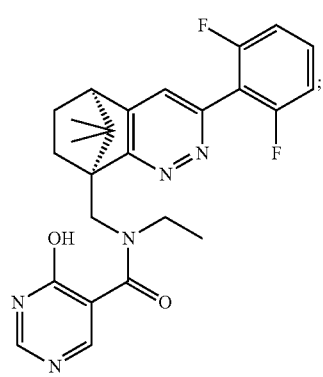
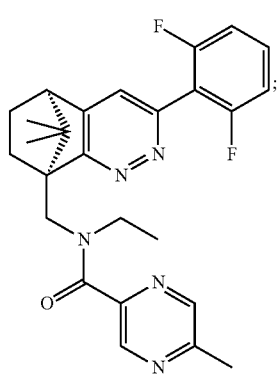
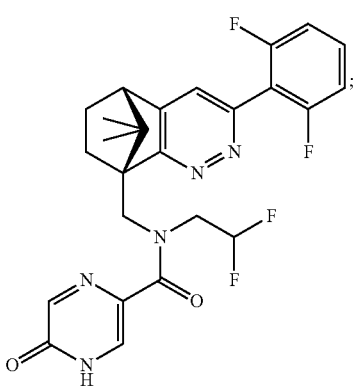

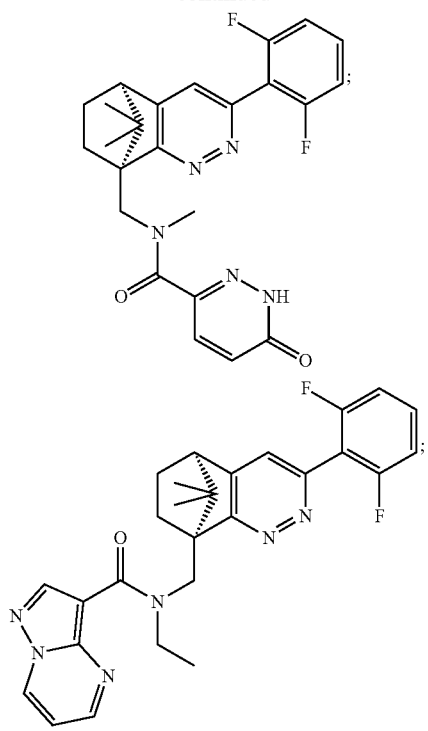
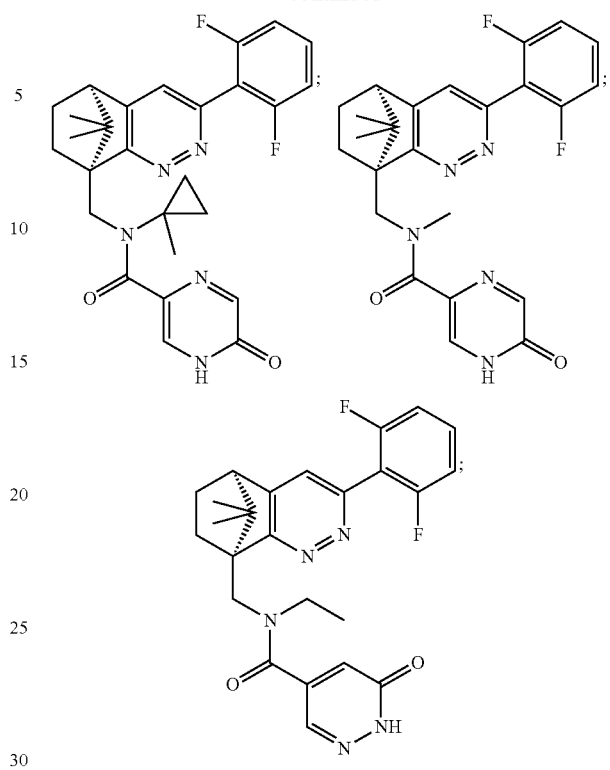
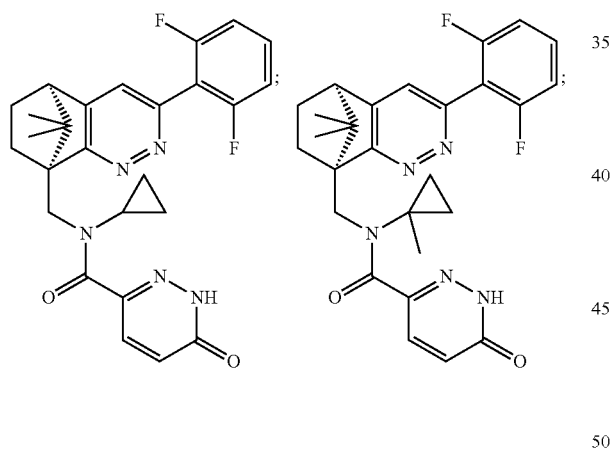
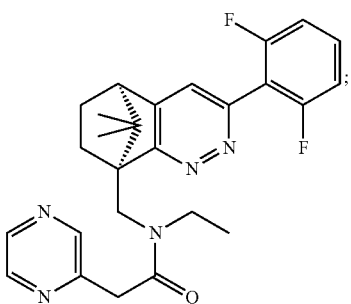
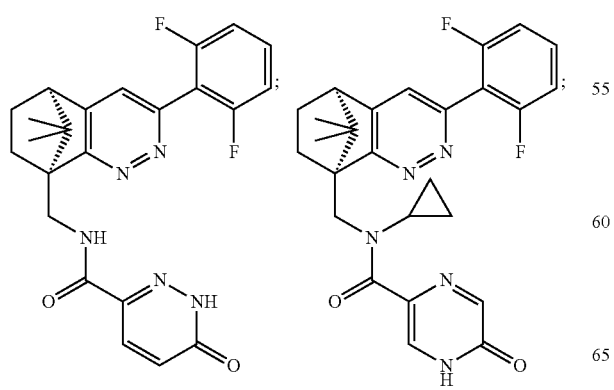
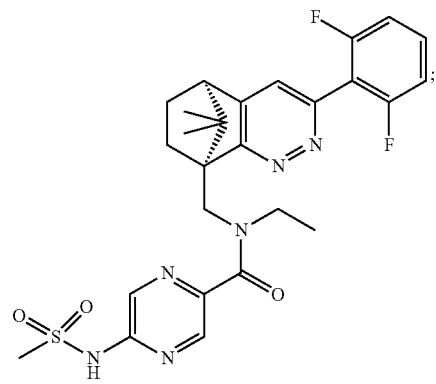

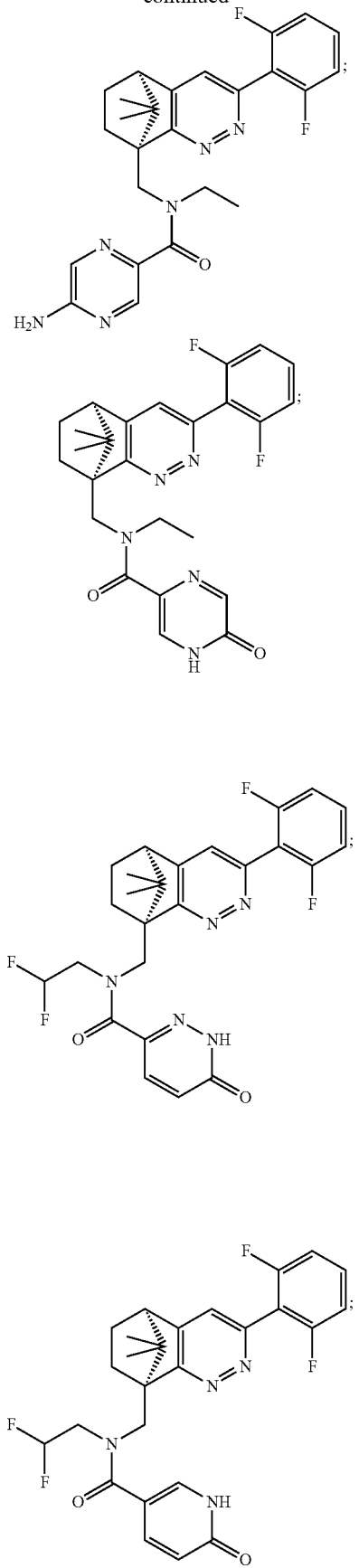
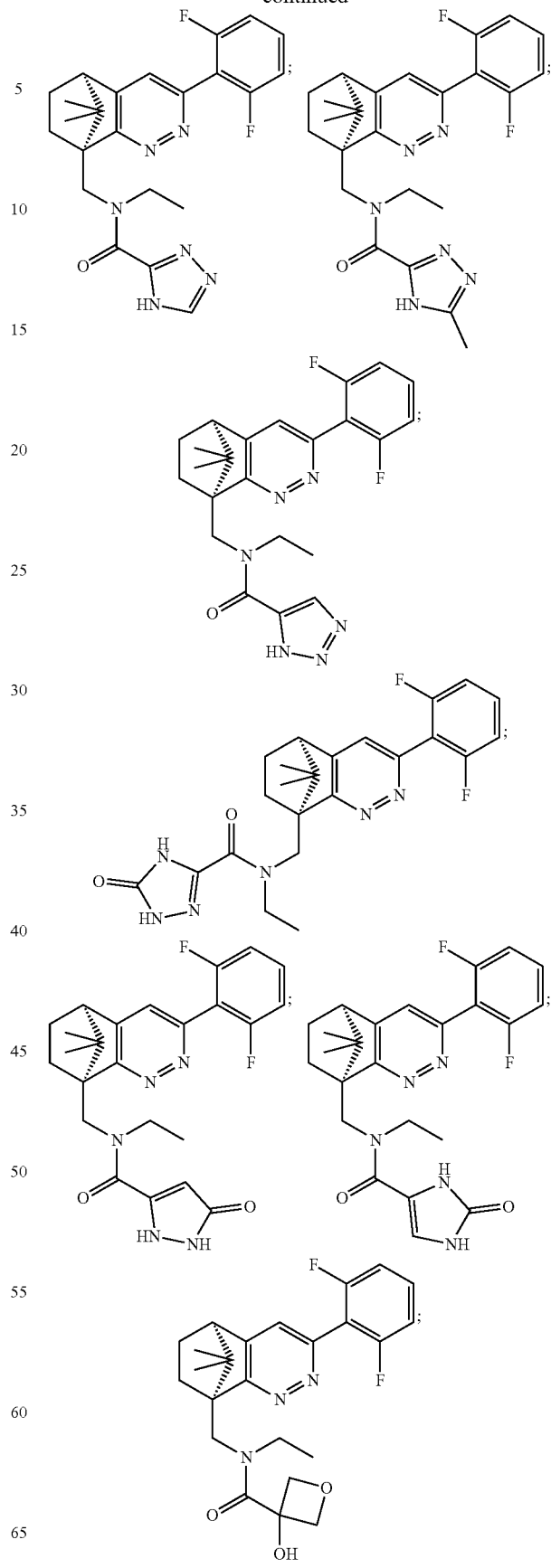

147
-continued
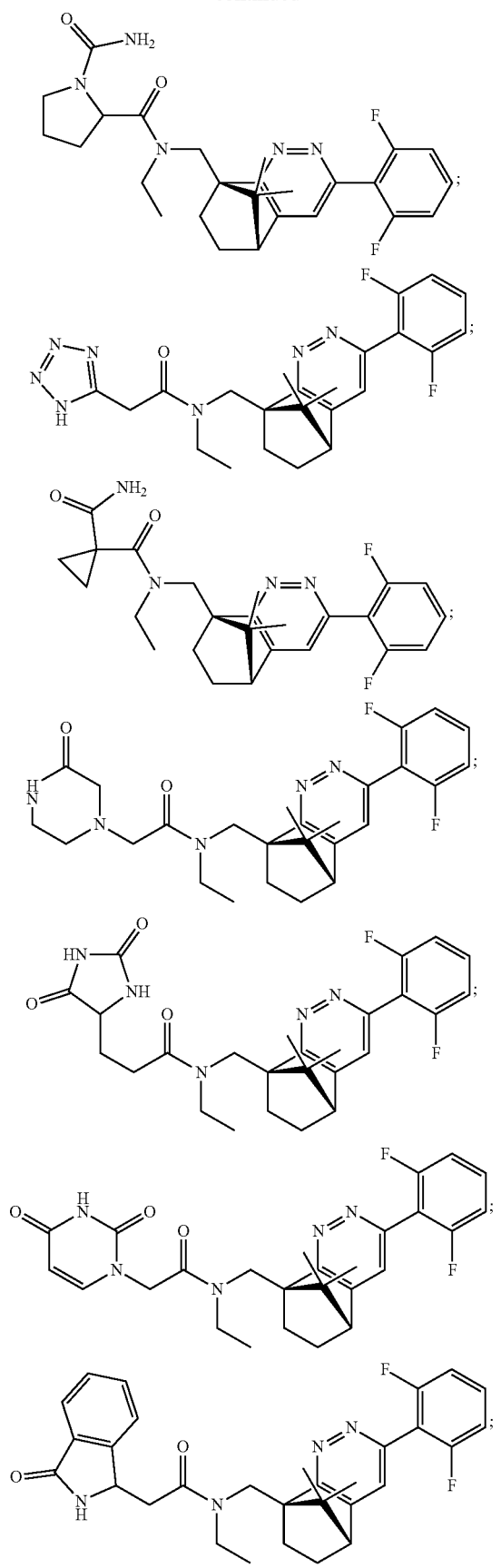
148
-continued
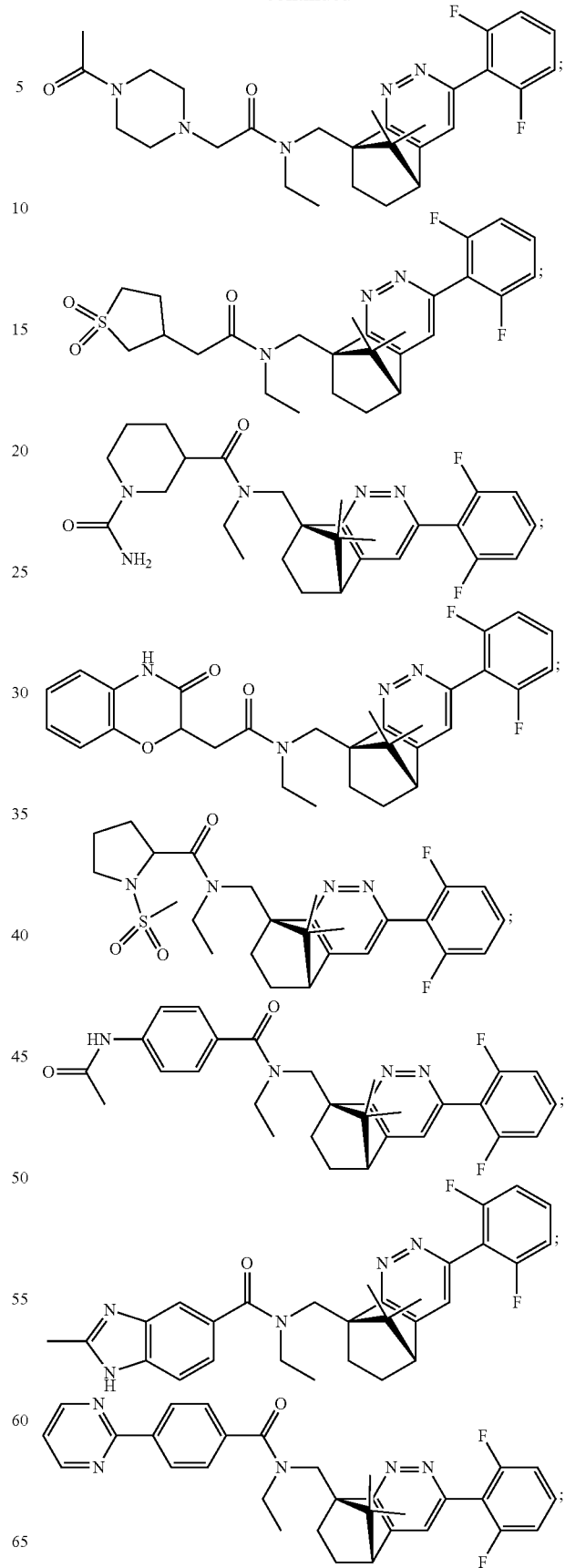

149
-continued
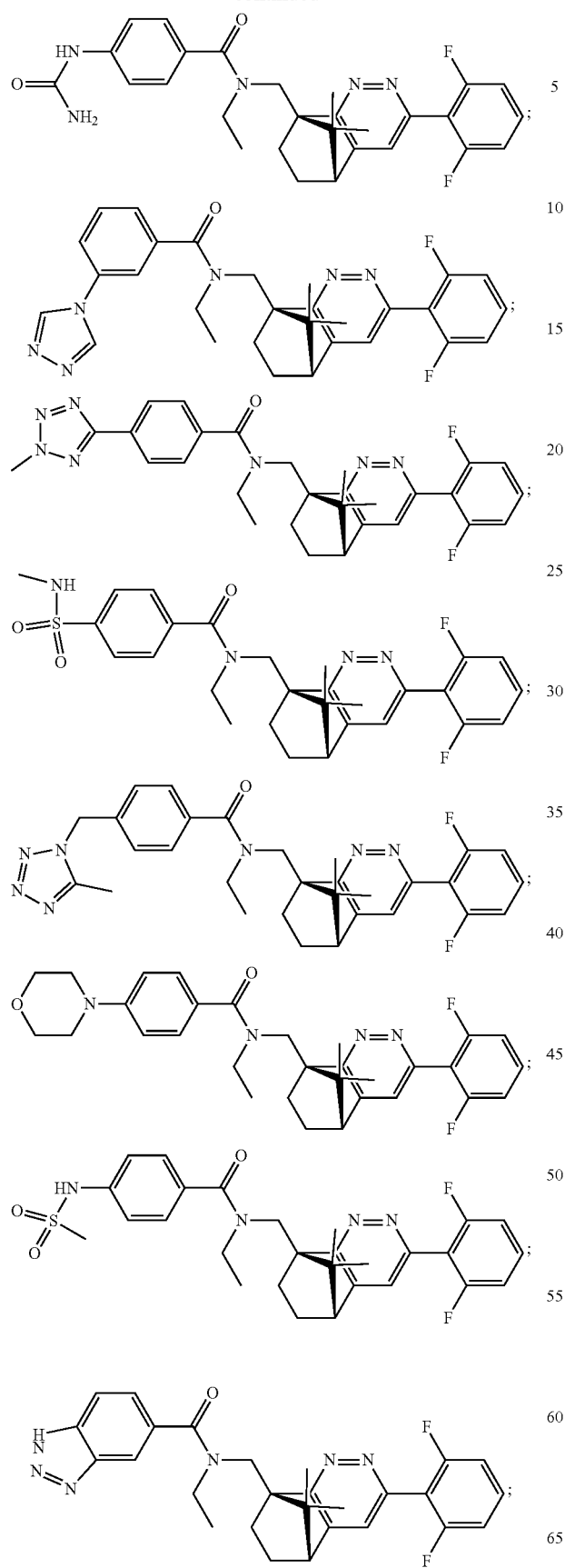
150
-continued
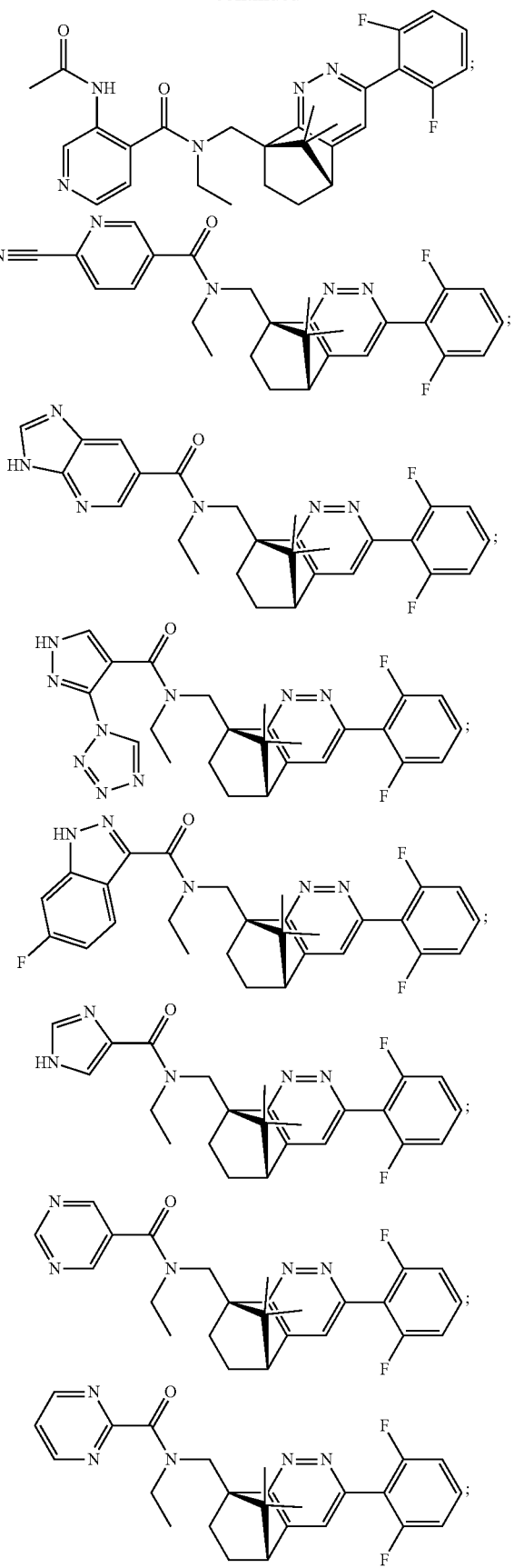

151
-continued
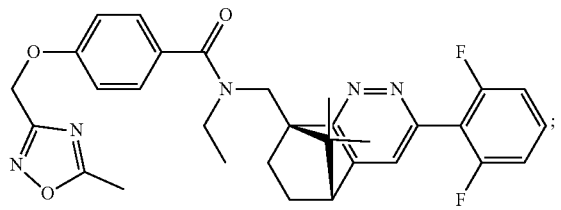
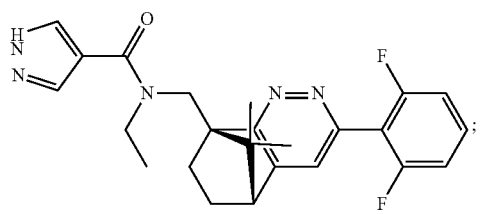
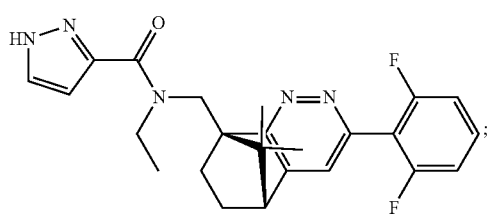
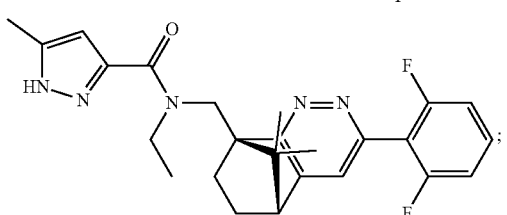
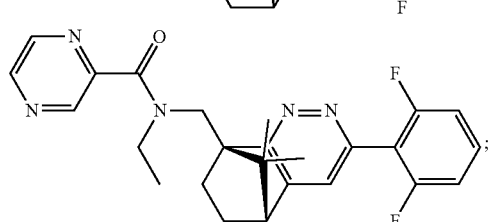
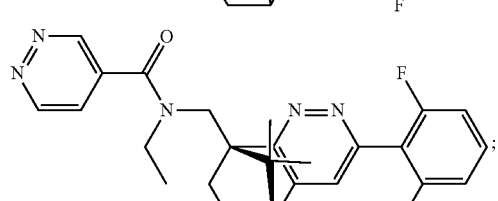
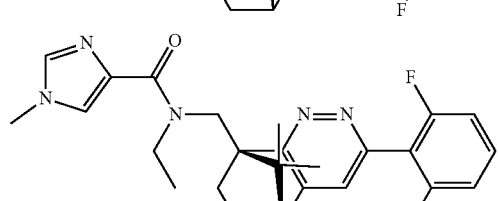
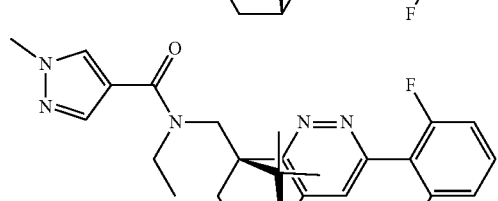
152
-continued
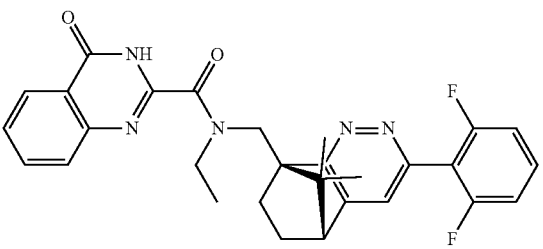
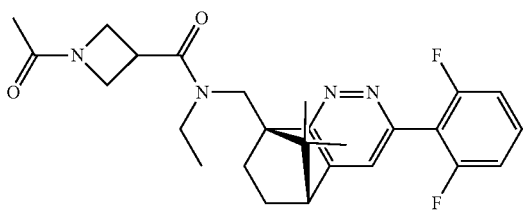
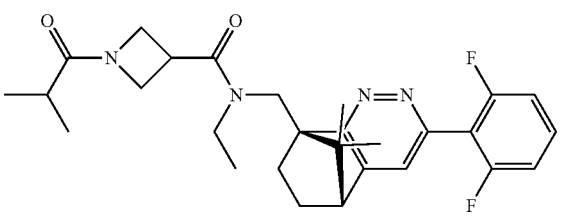
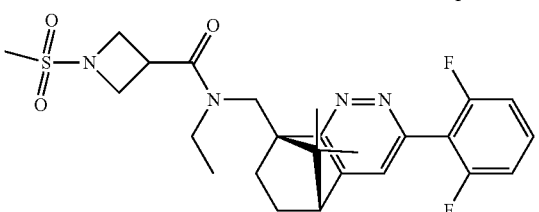
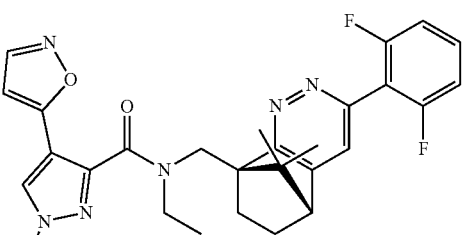
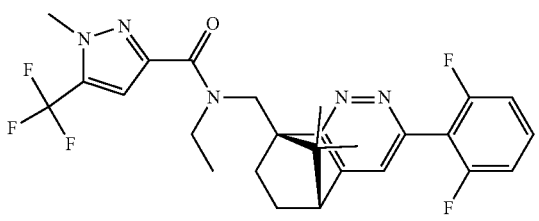
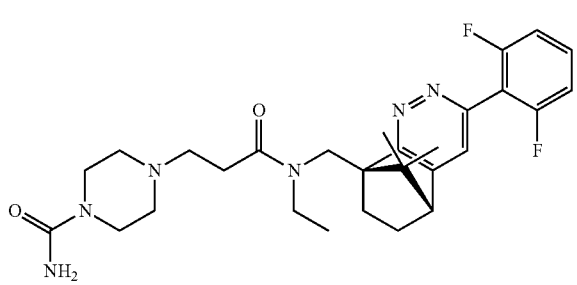

153
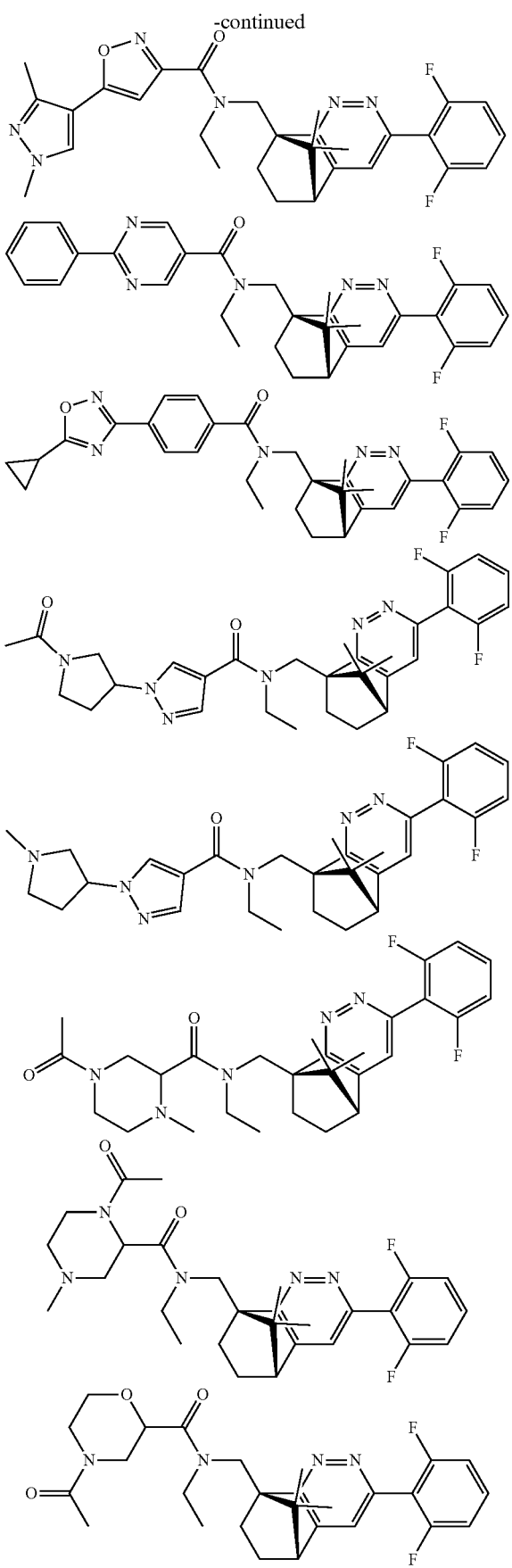
154
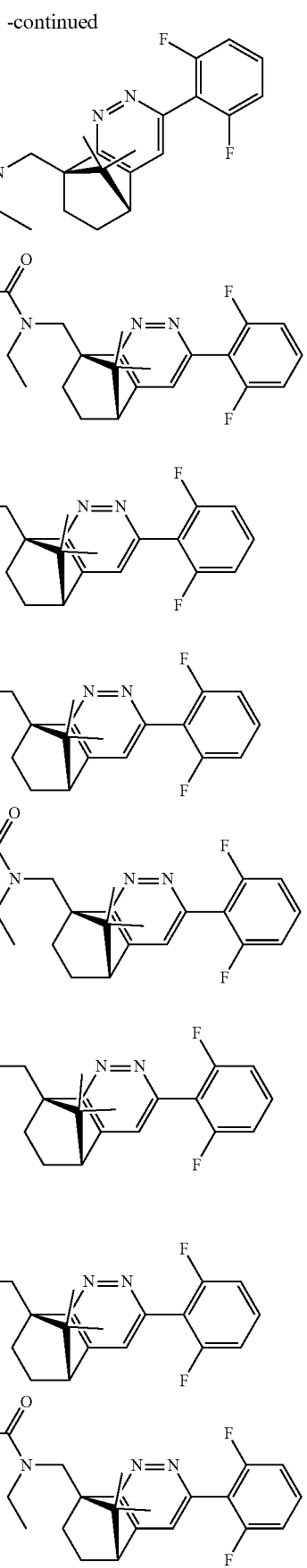

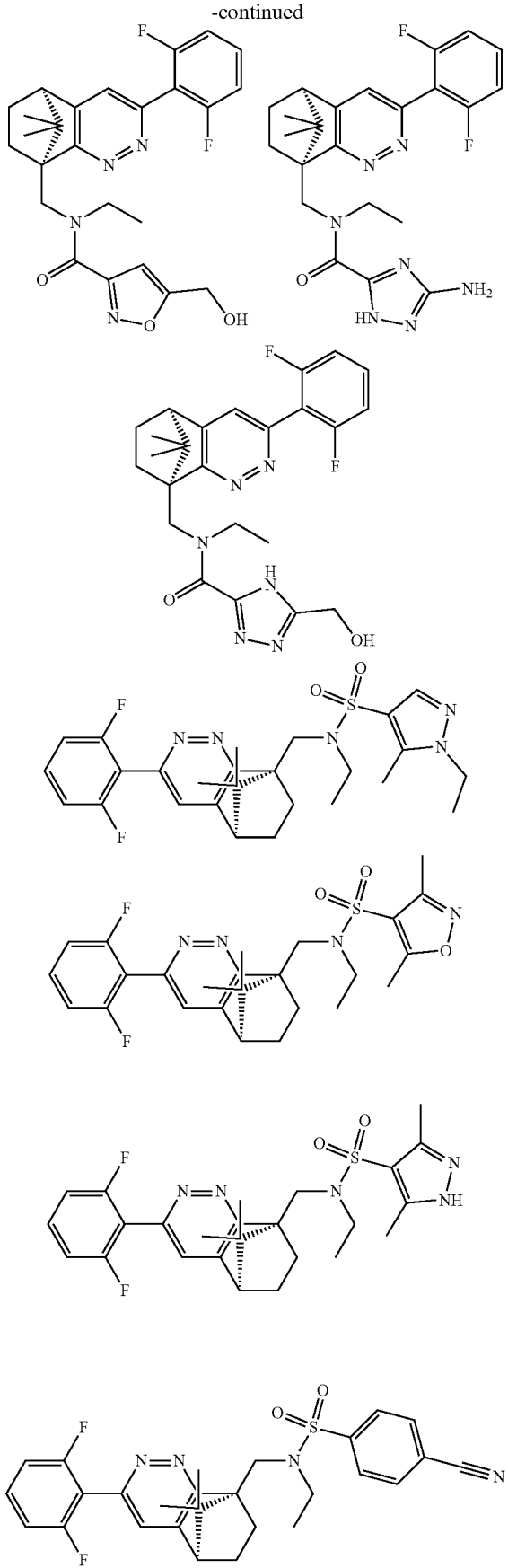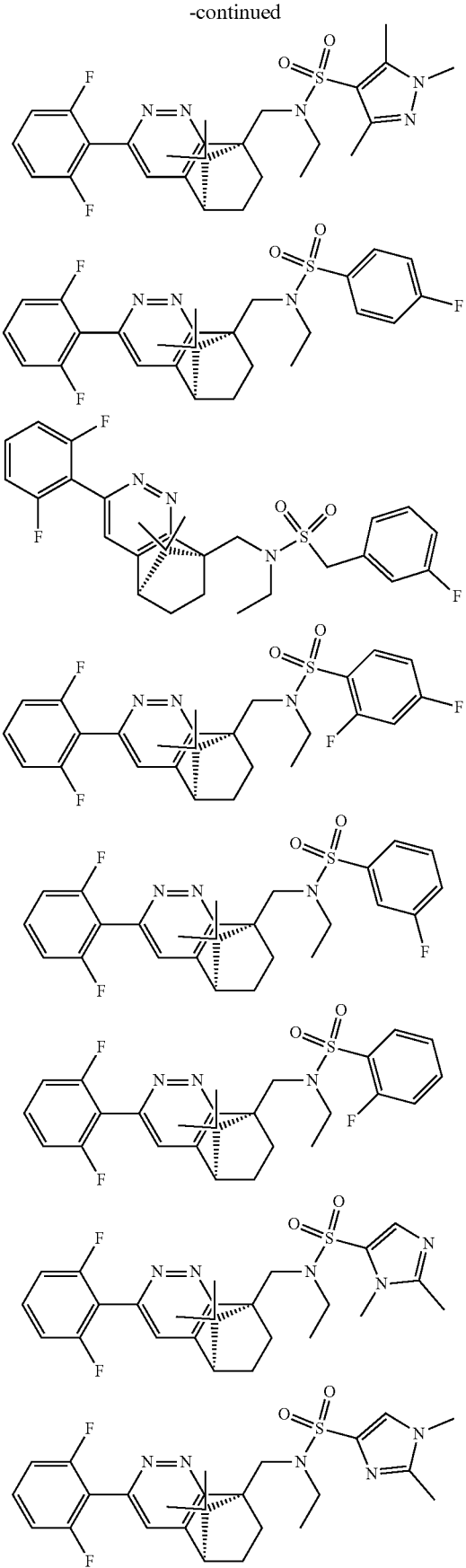

157
-continued
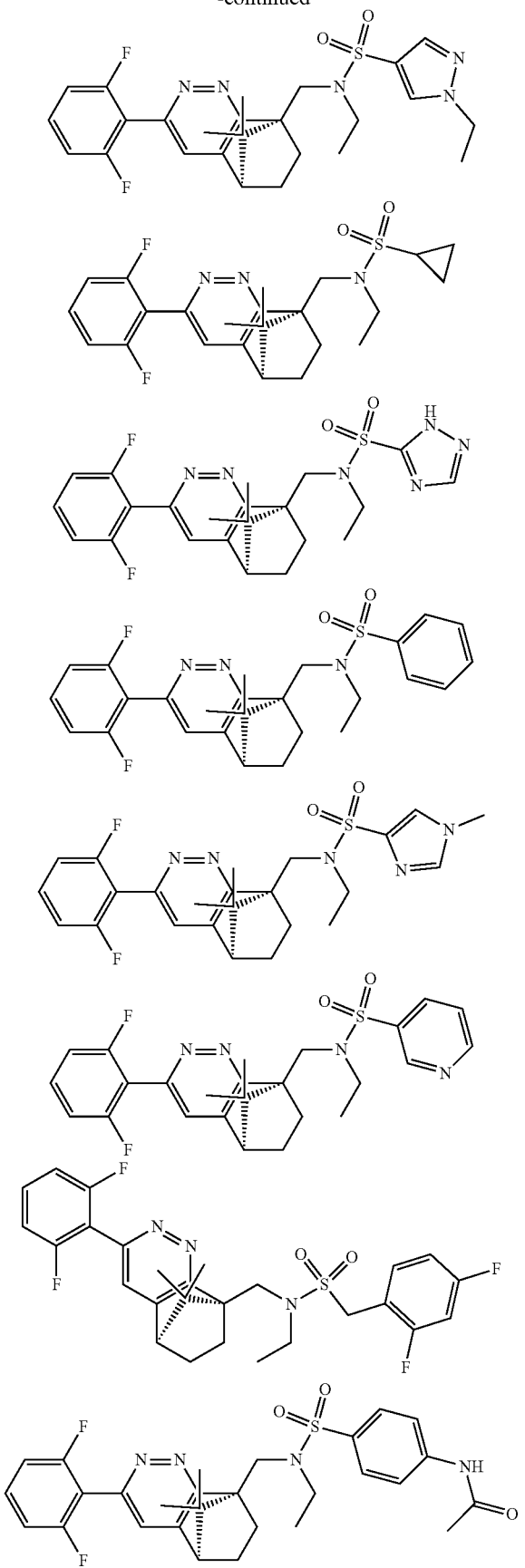
158
-continued
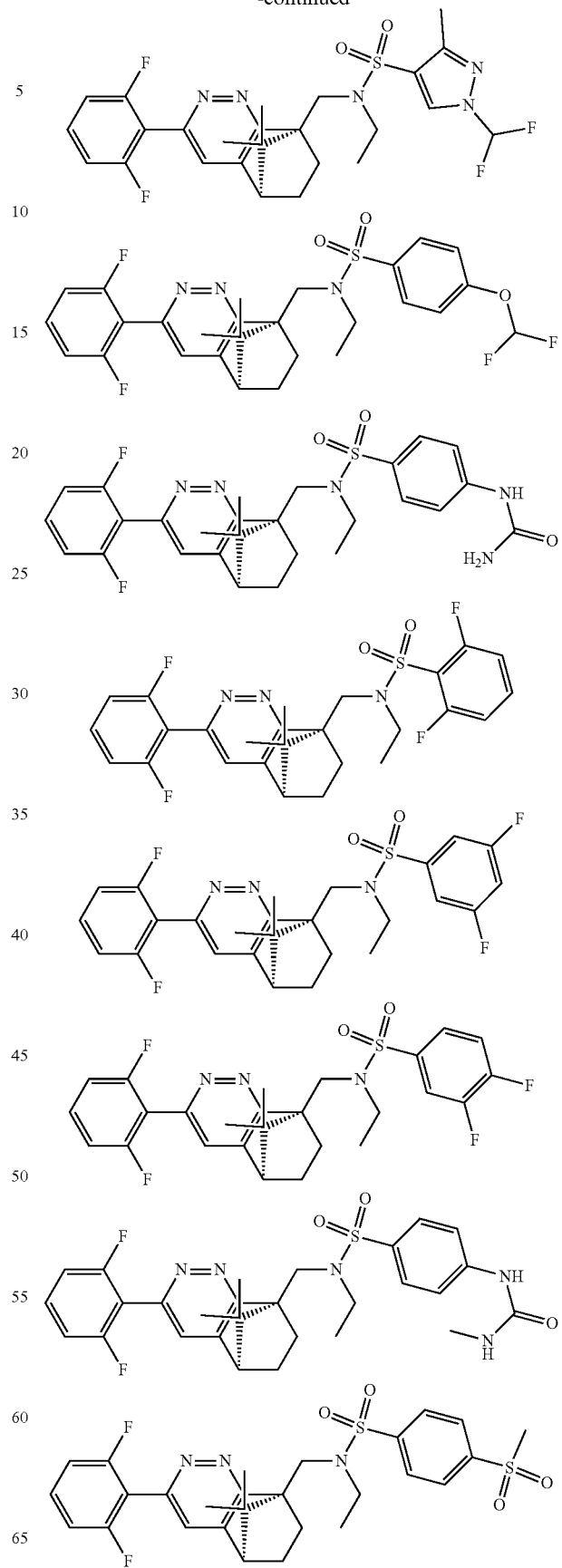

159
-continued
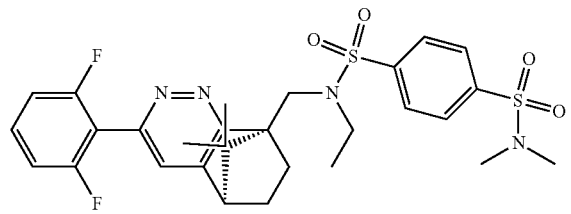
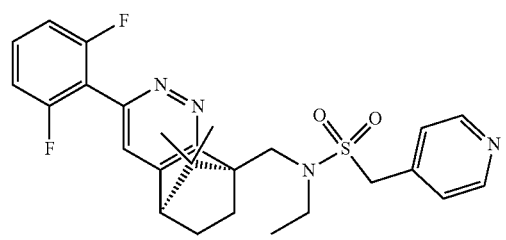
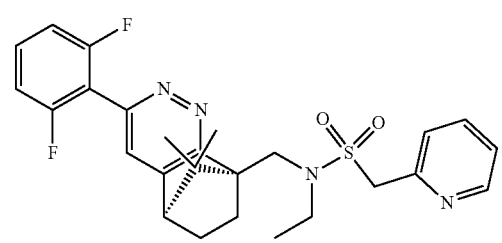
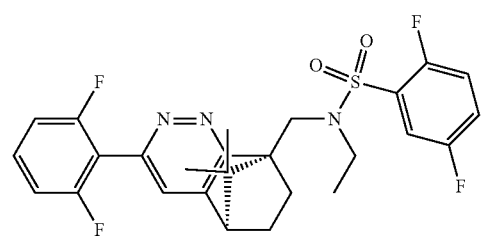
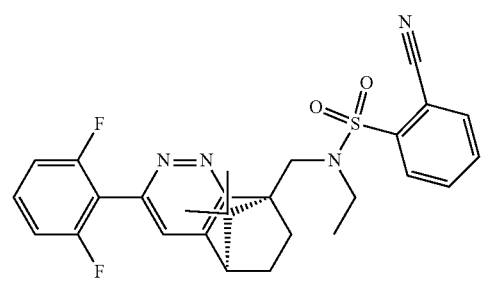
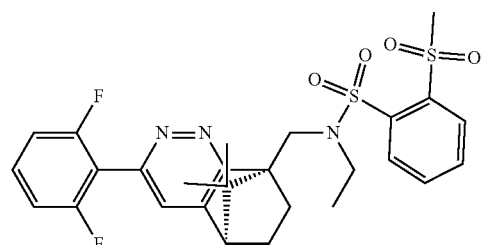
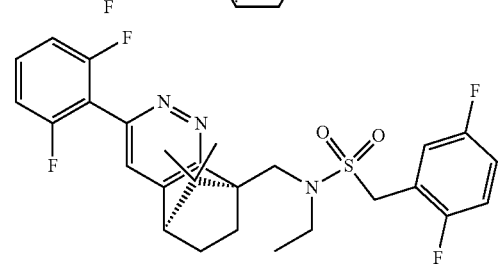
160
-continued
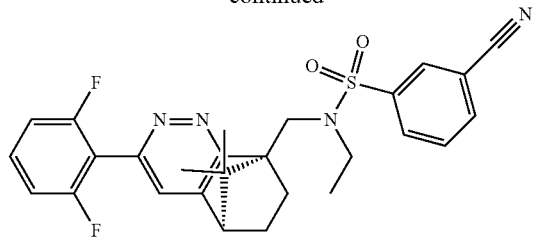
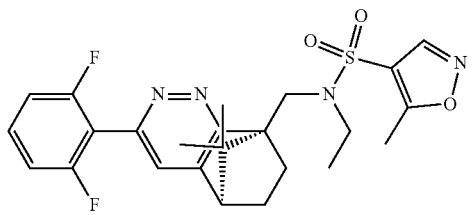
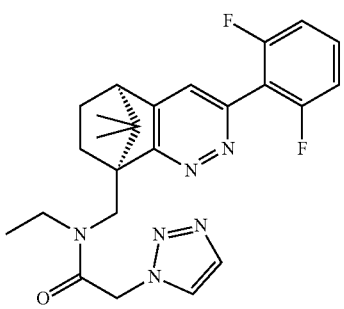
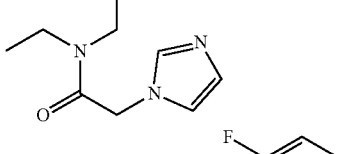
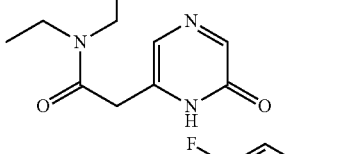
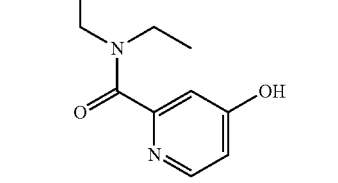

161
-continued
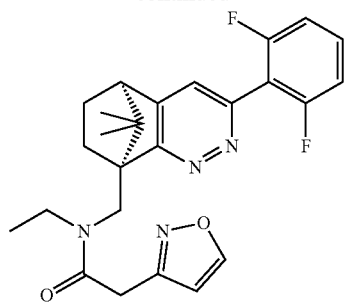
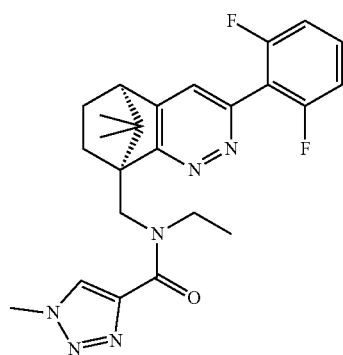
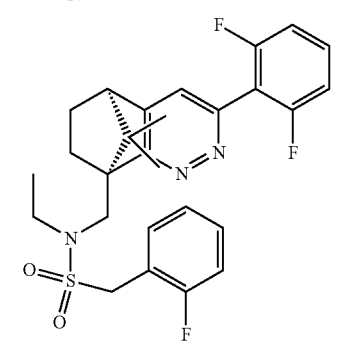
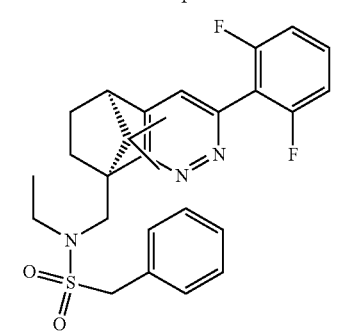
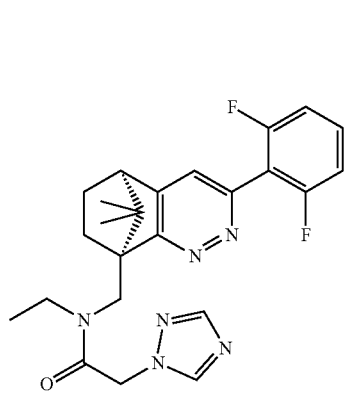
162
-continued
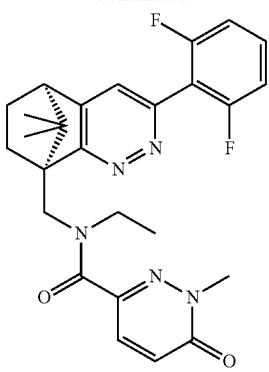
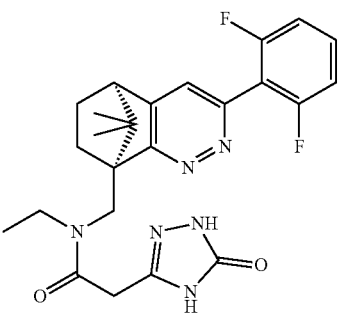
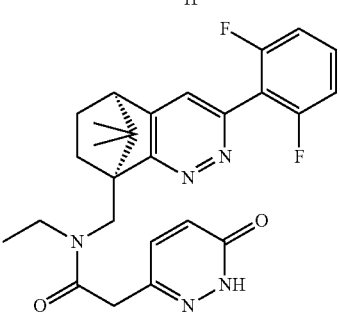
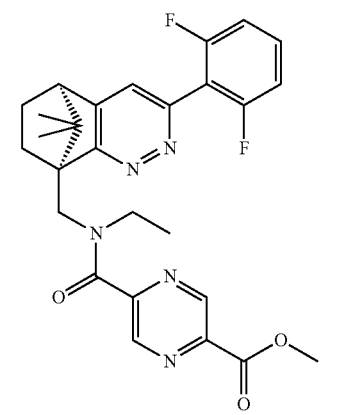
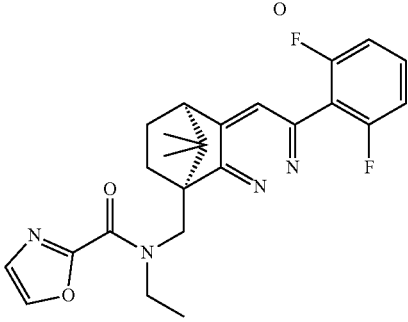

163
-continued
164
-continued
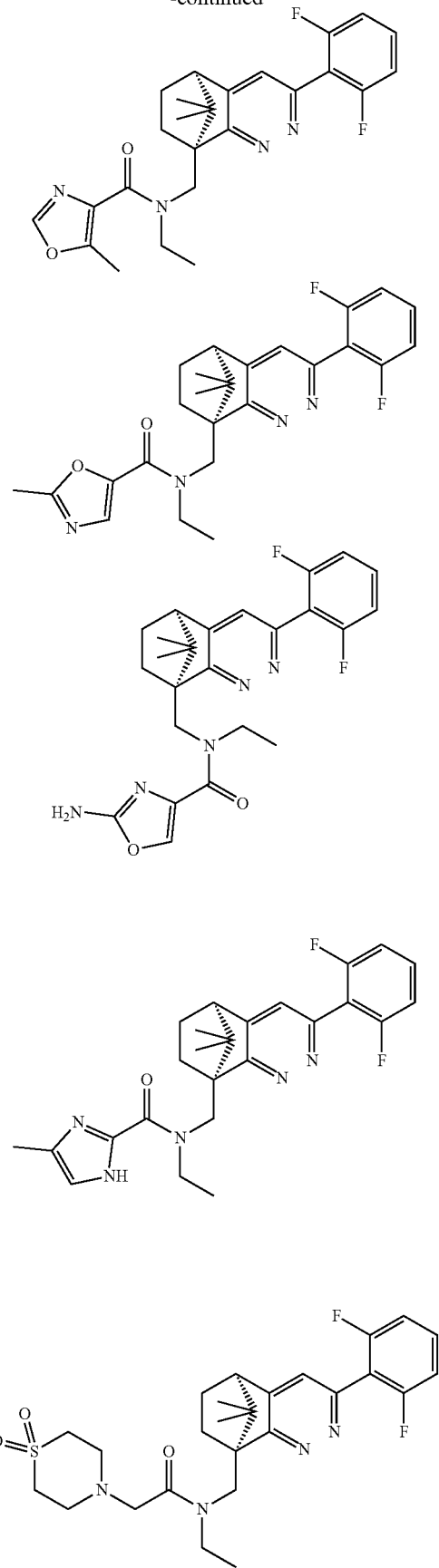
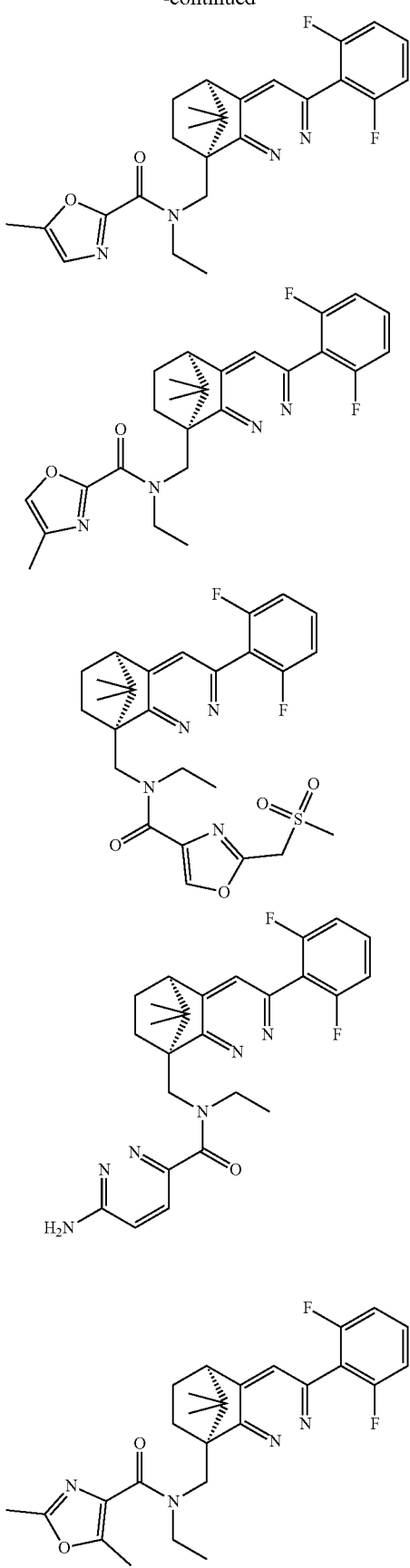

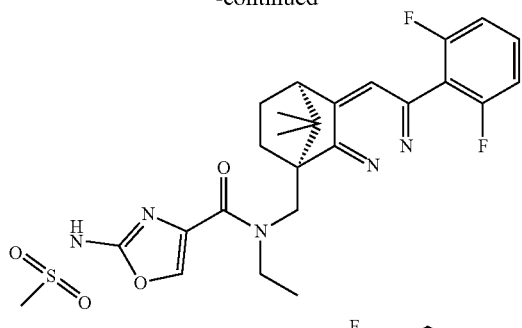
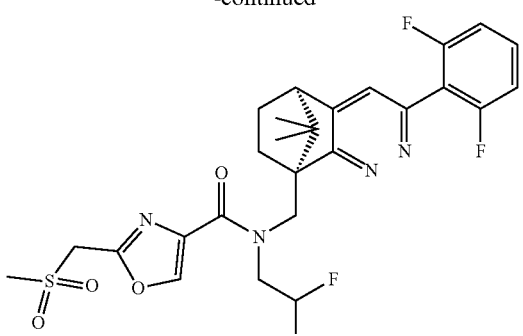
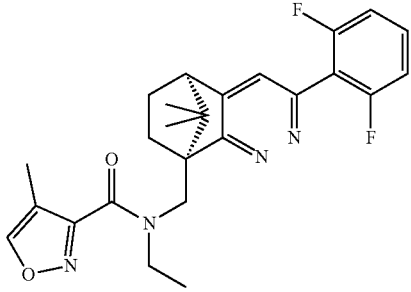
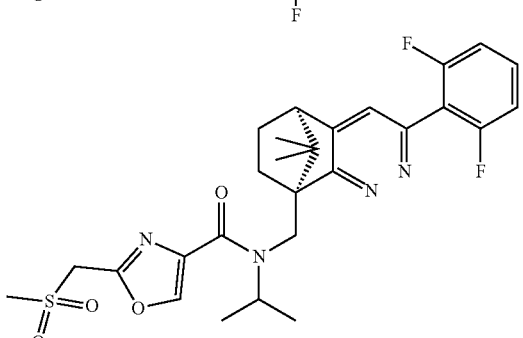
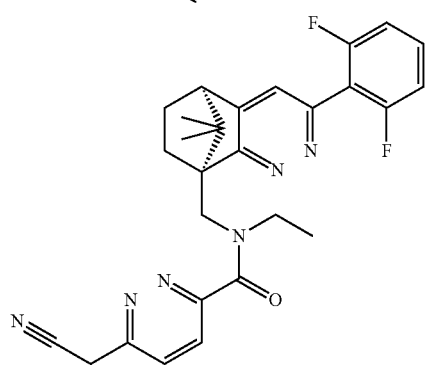
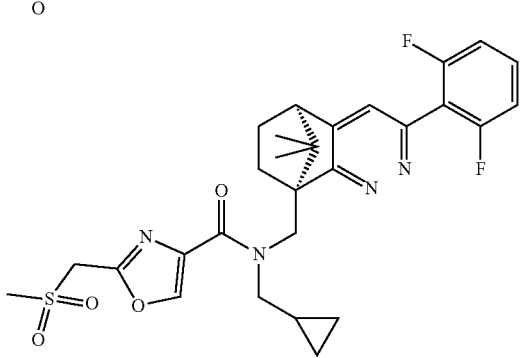
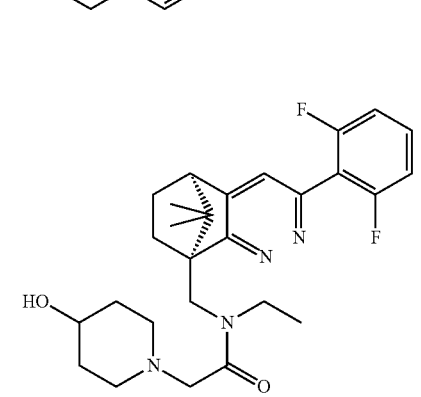
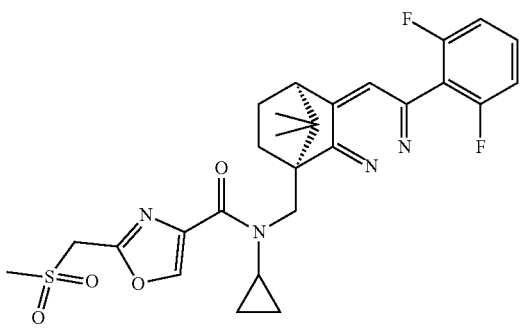
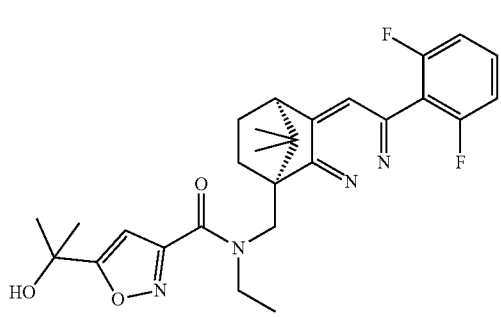
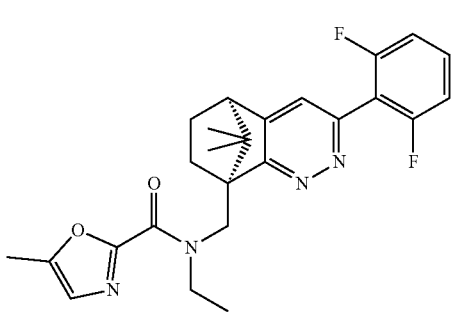

167
-continued
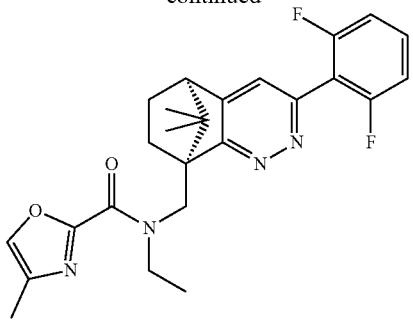
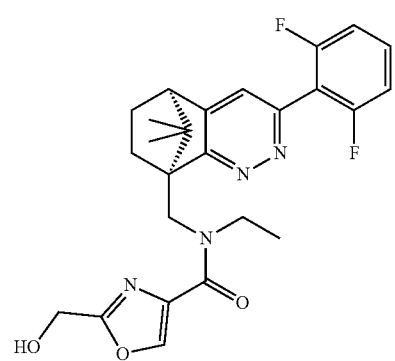
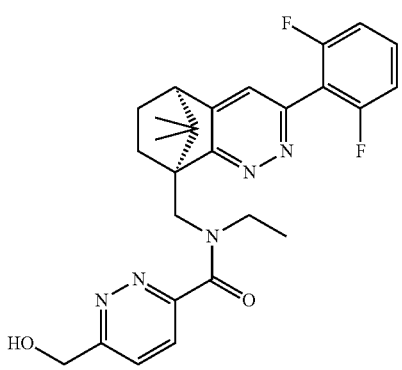
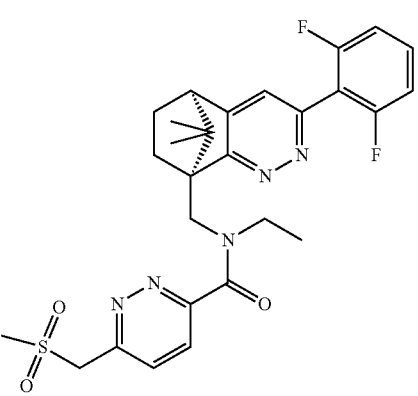
168
-continued
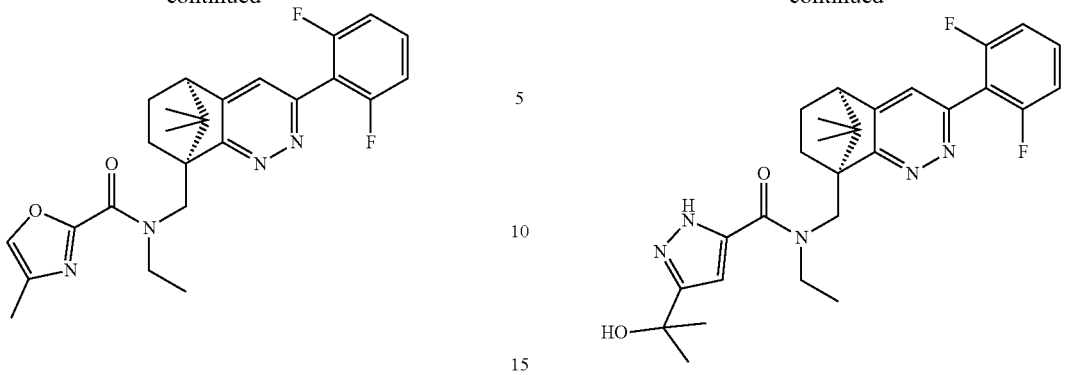
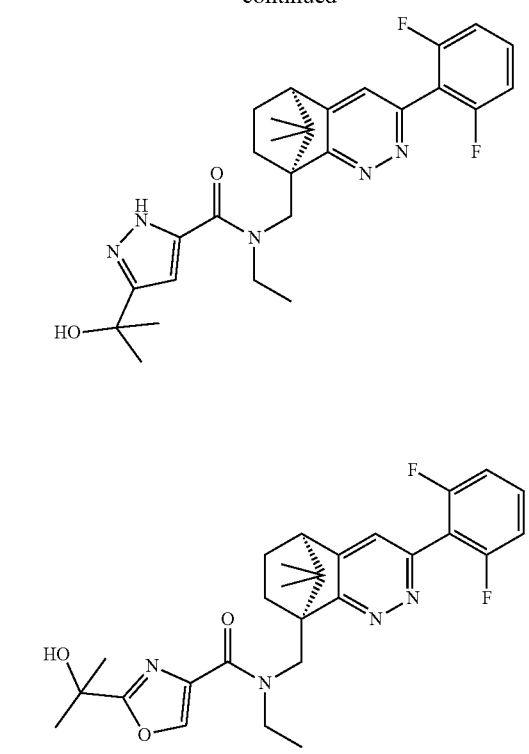
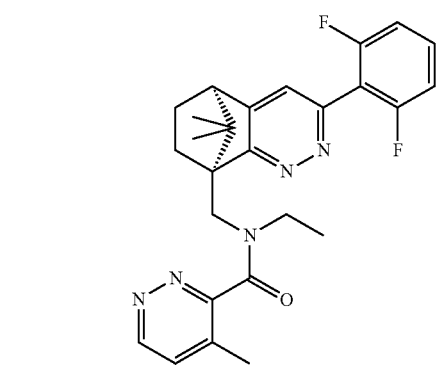
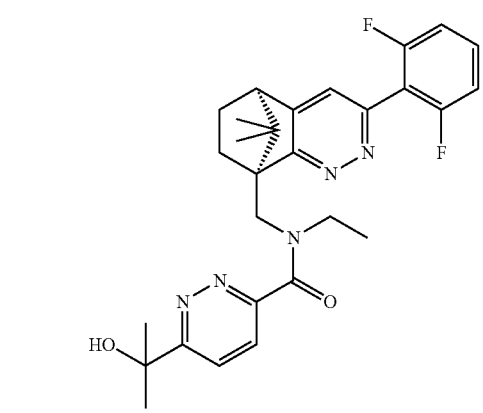

169
-continued
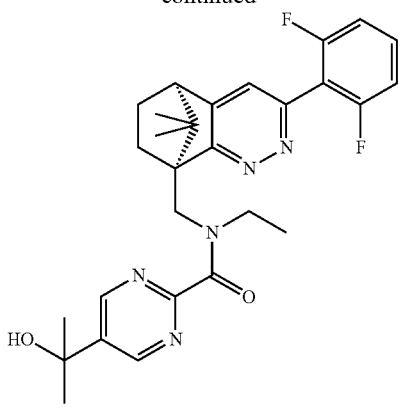
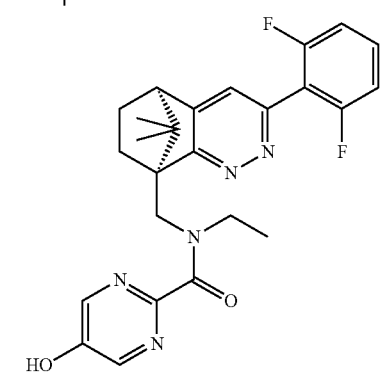
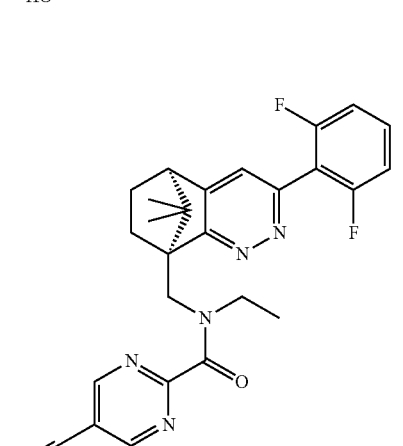
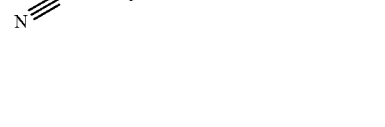
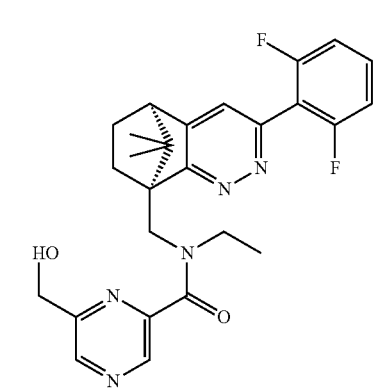
170
-continued
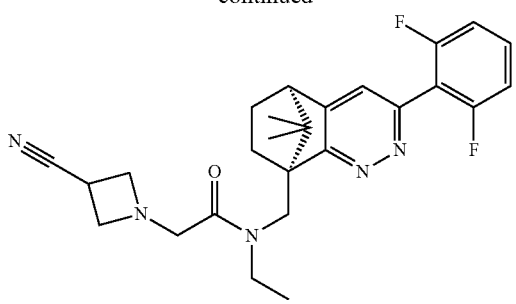
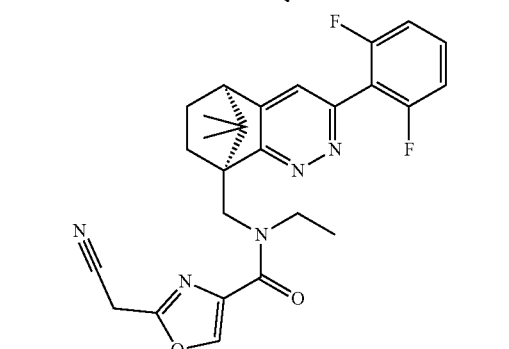
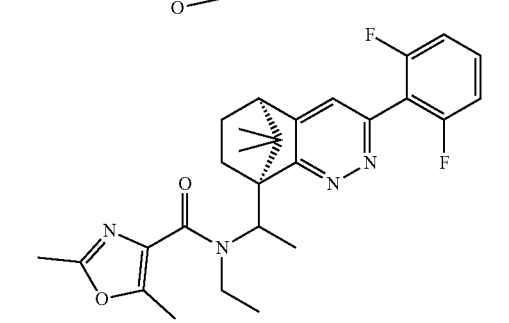
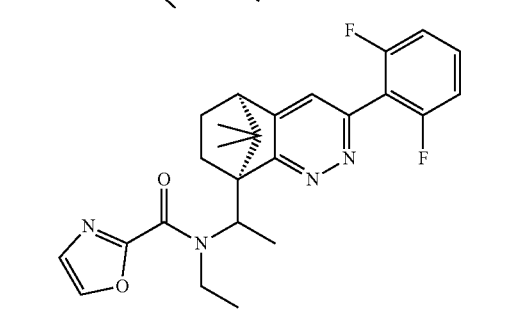
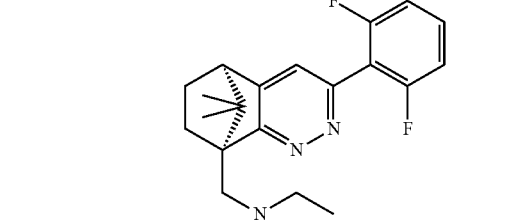

171
-continued
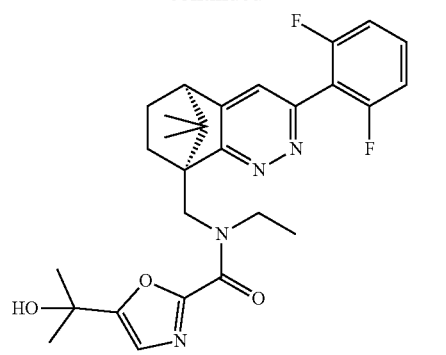
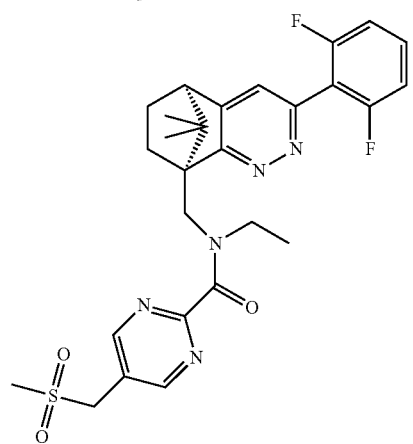
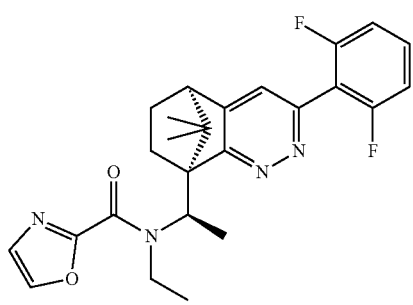
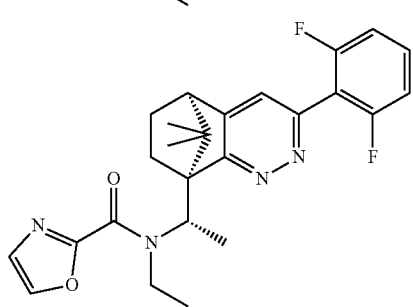
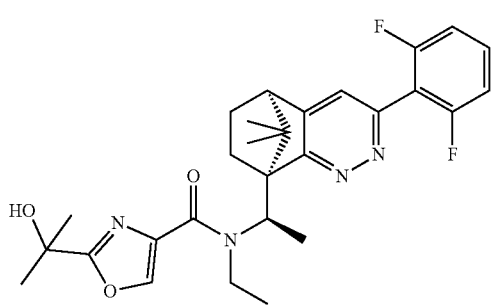
172
-continued
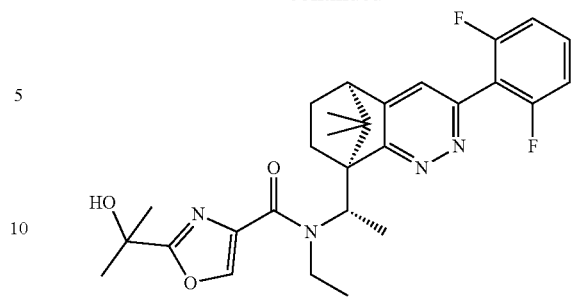
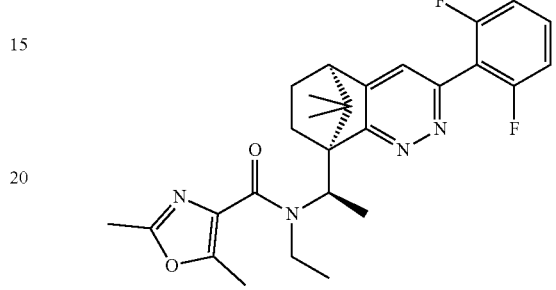
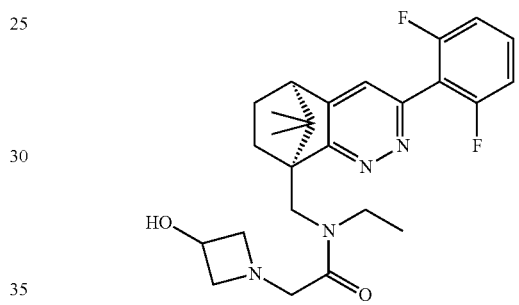
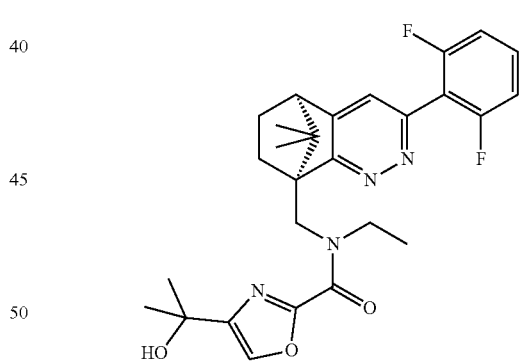
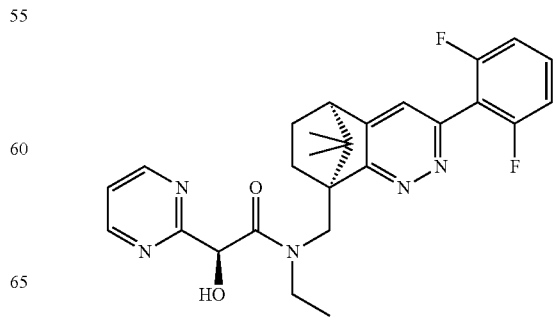

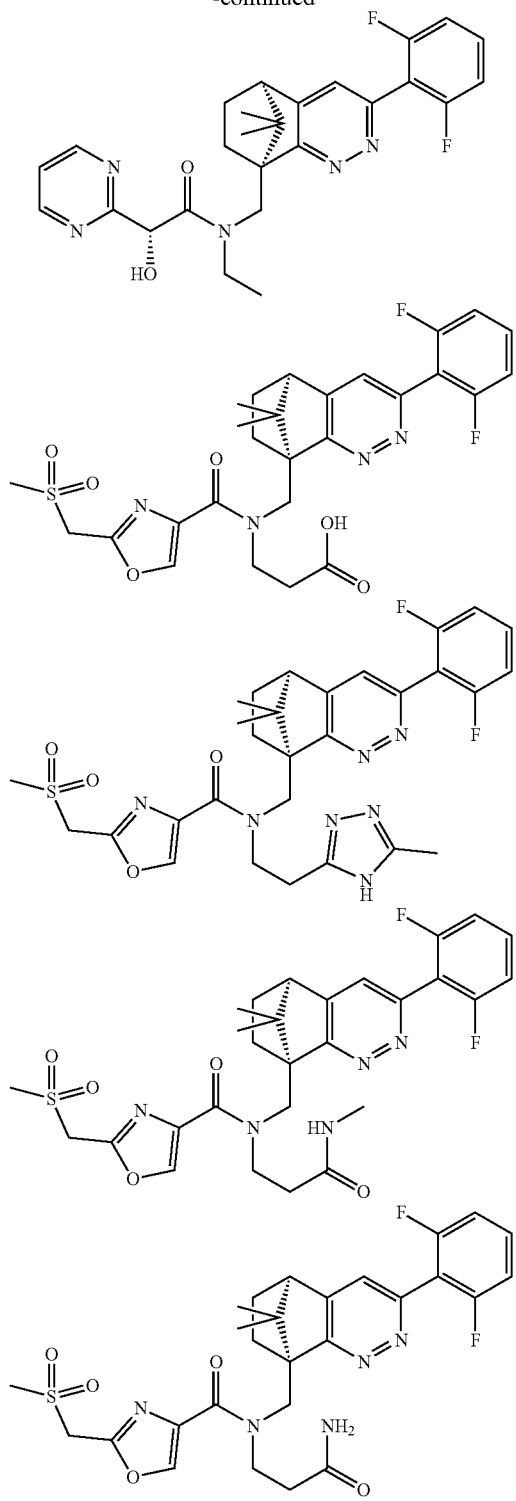
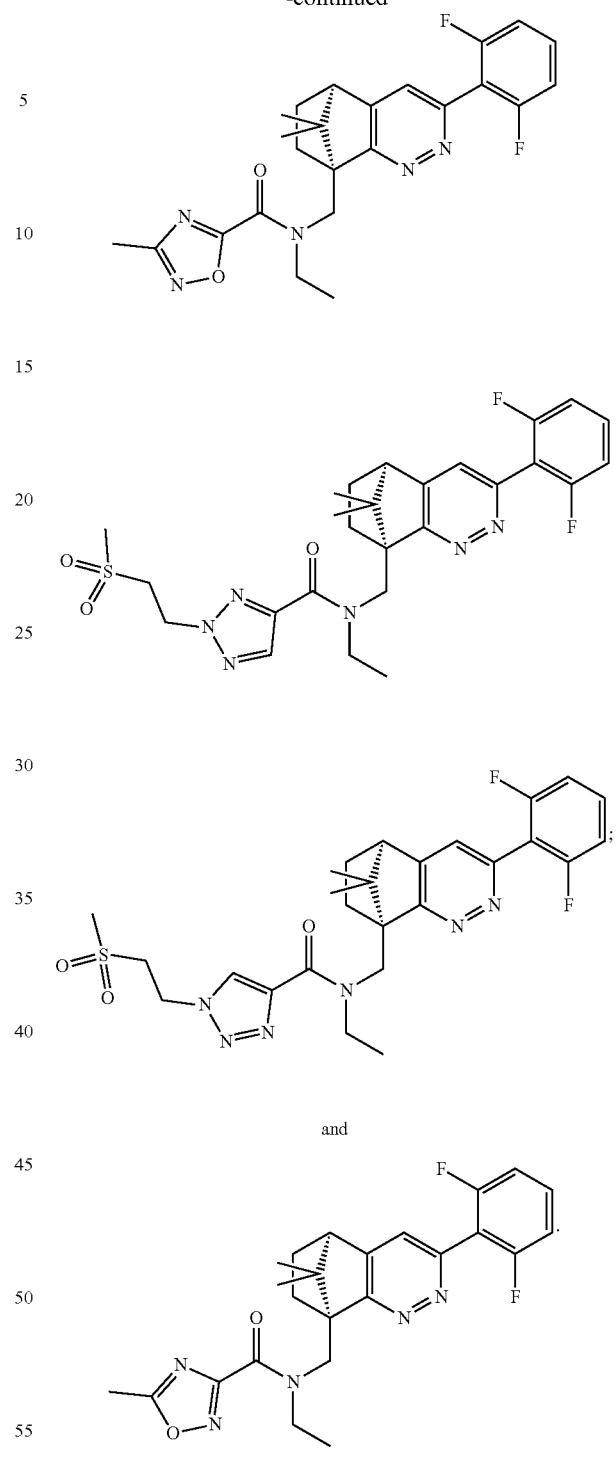

What is claimed is:
1. A compound of formula I

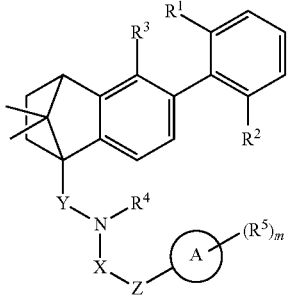

or pharmaceutically acceptable salts thereof, wherein:
A is:
  a five or six membered hetereoaryl selected from: oxazolyl; isoxazolyl; oxadiazolyl; thiazolyl; isothiazolyl; thiadiazolyl; triazolyl; pyrrolyl; pyrazolyl; imidazolyl; tetrazolyl; pyridinyl; pyrimidinyl; pyrazinyl; pyridazinyl; and triazinyl;
  a five or six membered heterocyclyl selected from: oxetanyl; azetidinyl; azepinyl; pyrrolidinyl; piperidinyl; piperazinyl; imidazolidinyl; tetrahydrofuranyl; tetrahydropyranyl; tetrahydrothienyl, 1,1-dioxo-tetrahydrothienyl; morpholinyl; thiomorpolinyl; and 1,1-dioxo-thiomorpholinyl;
  phenyl; or
  $C_{3-6}$ cycloalkyl;
X is: —C(O)— or —$SO_2$—;
Y is: methylene
Z is:
  a bond; or
  methylene;
m is: 0; 1; or 2;
$R^1$ is:
  halo;
$R^2$ is:
  halo;
$R^3$ is:
  hydrogen;
$R^4$ is:
  hydrogen;
  $C_{1-6}$alkyl; or
  halo-$C_{1-6}$alkyl;
$R^5$ is:
  $C_{1-6}$alkyl;
  $C_{1-6}$alkyloxy;
  halo-$C_{1-6}$alkyl;
  halo-$C_{1-6}$alkoxy;
  halo;
  hydroxyl;
  hydroxyl-$C_{1-6}$alkyl;
  oxo;
  cyano;
  cyano-$C_{1-6}$alkyl;
  $C_{1-6}$alkylsulfonyl;
  $C_{1-6}$alkylsulfonylamino;
  $C_{3-6}$cycloalkylsulfonyl;
  $C_{3-6}$cycloalkylsulfonylamino;
  $C_{1-6}$alkylsulfonyl;
  $C_{3-6}$cycloalkyl-$C_{1-6}$alkylsulfonylamino;
  $C_{1-6}$alkylsulfonyl-$C_{1-6}$alkyl;
  amino;
  aminocarbonyl;
  aminosulfonyl;
  $C_{1-6}$alkylcarbonyl;
  $C_{1-6}$alkylcarbonylamino;
  aminocarbonylamino;
  $C_{1-6}$alkyloxycarbonyl;
  $C_{1-6}$alkylaminosulfonyl;
  phenyl which may be unsubstituted or substituted once or twice with $R^b$;
  heteroaryl selected from: pyridinyl pyrimidinyl; pyrazinyl triazinyl; pyrazolyl; imidazolyl; oxazolyl; isoxazolyl; oxadiazolyl; and tetrazolyl; each of which may be unsubstituted or substituted once or twice with $R^a$;
  heteroaryl-$C_{1-6}$alkyl wherein the heteroaryl is selected from: pyridinyl pyrimidinyl; pyrazinyl triazinyl; pyrazolyl; imidazolyl; oxazolyl; oxadiazolyl; isoxazolyl; and tetrazolyl; each of which may be unsubstituted or substituted once or twice with $R^a$;
  heteroaryl-$C_{1-6}$alkoxy wherein the heteroaryl is selected from: pyridinyl pyrimidinyl; pyrazinyl triazinyl; pyrazolyl; imidazolyl; oxazolyl; oxadiazolyl; isoxazolyl; and tetrazolyl; each of which may be unsubstituted or substituted once or twice with $R^a$;
  heterocyclyl selected from: morpholinyl; pyrrolidinyl; oxetanyl; and azetidinyl each of which may be unsubstituted or substituted once or twice with $R^b$;
$R^a$ is:
  $C_{1-6}$alkyl;
  $C_{3-6}$cycloalkyl;
  halo-$C_{1-6}$alkyl;
  halo;
  hydroxyl;
  hydroxyl-$C_{1-6}$alkyl; or
  oxo;
$R^b$ is:
  $C_{1-6}$alkyl;
  $C_{1-6}$alkylcarbonyl;
  $C_{1-6}$alkylsulfonyl;
  halo-$C_{1-6}$alkyl;
  halo;
  hydroxyl;
  hydroxyl-$C_{1-6}$alkyl; or
  oxo; and
$R^c$ is:
  hydroxyl;
  $C_{1-6}$alkoxy; or
  amino;
provided that the compound is not N-(((5R,8S)-3-(2,6-difluorophenyl)-9,9-dimethyl-5,6,7,8-tetrahydro-5,8-methanocinnolin-8-yl)methyl)-N-ethyl-5-methylisoxazole-3-carboxamide.

2. The compound of claim 1, wherein:
a five or six membered hetereoaryl selected from: oxazolyl; isoxazolyl; oxadiazolyl; thiazolyl; isothiazolyl; thiadiazolyl; triazolyl; pyrrolyl; pyrazolyl; imidazolyl; tetrazolyl; pyridinyl; pyrimidinyl; pyrazinyl; pyridazinyl; and triazinyl; or
phenyl.

3. The compound of claim 1, wherein A is a five or six membered hetereoaryl selected from: oxazolyl; isoxazolyl; oxadiazolyl; thiazolyl; triazolyl; pyrrolyl; pyrazolyl; imidazolyl; tetrazolyl; pyridinyl; pyrimidinyl; pyrazinyl; and pyridazinyl.

4. The compound of claim 1, wherein X is —C(O)—.

5. The compound of claim 1, wherein X is —SO$_2$—.

6. The compound of claim 1, wherein Z is a bond.

7. The compound of claim 1, wherein Z is methylene.

8. The compound of claim 1, wherein m is 0 or 1.

9. The compound of claim 1, wherein R$^1$ and R$^2$ are fluoro.

10. The compound of claim 1, wherein R$^4$ is C$_{1-6}$ alkyl.

11. The compound of claim 1, wherein the compound is of formula II

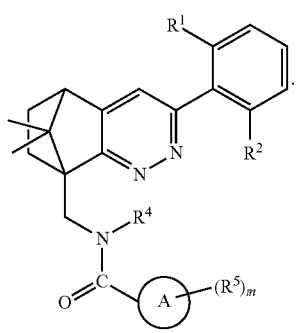

II

12. The compound of claim 1, wherein the compound is of formula III

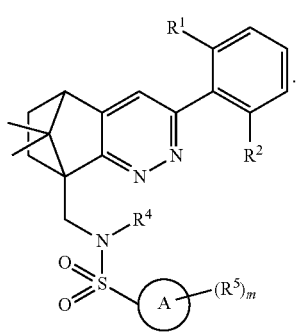

III

13. A composition comprising:
(a) a pharmaceutically acceptable carrier; and
(b) a compound of claim 1.

14. A compound selected from: